(12) United States Patent
Schipper et al.

(10) Patent No.: US 12,329,590 B2
(45) Date of Patent: Jun. 17, 2025

(54) OPTICALLY DETECTABLE MARKERS FOR TRACKING, AND METHODS FOR MANUFACTURING, ASSEMBLING, AND USING THE SAME

(71) Applicant: INTELLIJOINT SURGICAL INC., Kitchener (CA)

(72) Inventors: Joseph Arthur Schipper, Kitchener (CA); Andre Novomir Hladio, Waterloo (CA); Ryan Visee, Mississauga (CA)

(73) Assignee: Intellijoint Surgical Inc., Kitchener (CA)

( * ) Notice: Subject to any disclaimer, the term of this patent is extended or adjusted under 35 U.S.C. 154(b) by 488 days.

(21) Appl. No.: 17/851,941

(22) Filed: Jun. 28, 2022

(65) Prior Publication Data
US 2022/0323175 A1 Oct. 13, 2022

Related U.S. Application Data

(63) Continuation-in-part of application No. PCT/CA2021/051550, filed on Nov. 2, 2021.
(Continued)

(51) Int. Cl.
*A61B 90/00* (2016.01)

(52) U.S. Cl.
CPC ...... *A61B 90/39* (2016.02); *A61B 2090/3937* (2016.02)

(58) Field of Classification Search
CPC .. A61B 2017/00526; A61B 2034/2048; A61B 2034/2055; A61B 2090/3937; A61B 2090/3945; A61B 2090/3983; A61B 90/39

See application file for complete search history.

(56) References Cited

U.S. PATENT DOCUMENTS

| | | |
|---|---|---|
| 8,386,022 B2 | 2/2013 | Jutras et al. |
| 10,335,239 B2 | 7/2019 | Plassky et al. |

(Continued)

FOREIGN PATENT DOCUMENTS

| | | |
|---|---|---|
| CN | 113133830 A | 7/2021 |
| WO | 2019012520 A1 | 1/2019 |

OTHER PUBLICATIONS

Extended European Search Report dated Jul. 23, 2024, 8 Pages for Corresponding European Patent Application No. 21887944.3.
(Continued)

*Primary Examiner* — Michael T Rozanski

(57) ABSTRACT

Provided are optically detectable markers for tracking, as well as related methods. A marker comprises a mask unit and a (removable) cartridge comprising an optically detectable surface exposed through at least three faces of the mask unit. Respective materials present a measurable contrast under optical detection conditions. An optical detectable surface can be detectable using IR and a contrasting surface is not. Faces can define openings to the cartridge. The cartridge can comprise a sheet of optically detectible material foldable to fit into the mask unit. A sheet can provide multiple connected cartridges. Securing devices including any of a support unit, a clip, a magnet, an adhesive, etc., can secure a cartridge in a mask unit. A marker, or maker kit, may comprise a plurality of mask units and cartridges connected via a marker body. Some of the mask units may be on different planes in such a marker.

20 Claims, 23 Drawing Sheets

Related U.S. Application Data

(60) Provisional application No. 63/109,017, filed on Nov. 3, 2020.

(56) References Cited

U.S. PATENT DOCUMENTS

| | | |
|---|---|---|
| 2004/0138556 A1 | 7/2004 | Cosman |
| 2007/0100325 A1 | 5/2007 | Jutras et al. |
| 2009/0163930 A1 | 6/2009 | Aoude et al. |

OTHER PUBLICATIONS

International Search Report and Written Opinion mailed Jan. 4, 2022, in corresponding PCT Application No. PCT/CA2021/051550.
YouTube video; youtube.com/watch?v=7aujpCKeuYw; Paper Folding a Tetrahedron (pyramid) for the Origami-challenged; Caroline Ainslie; 5 pages.

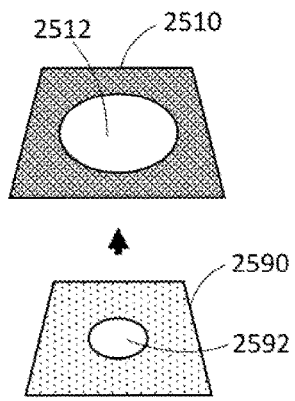
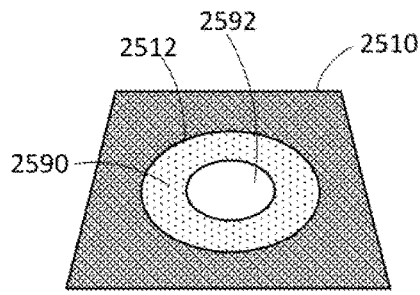
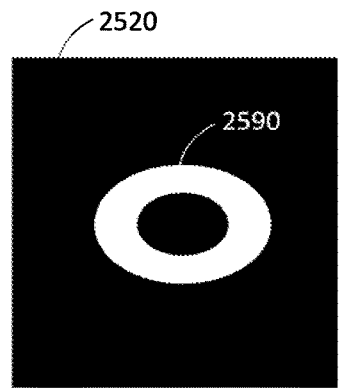
Figure 25A
Figure 25B
Figure 25C
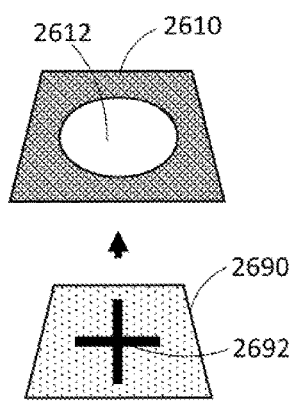
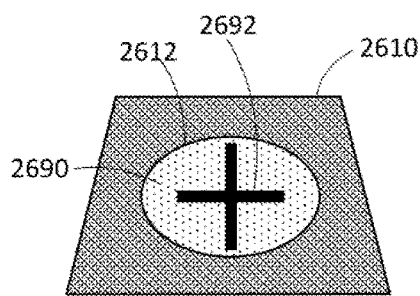
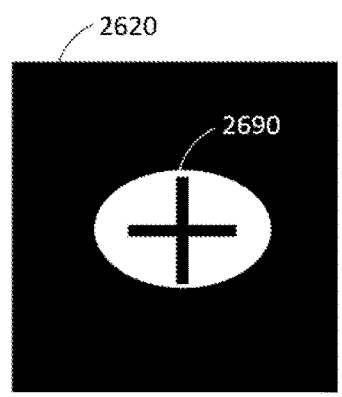
Figure 26A
Figure 26B
Figure 26C
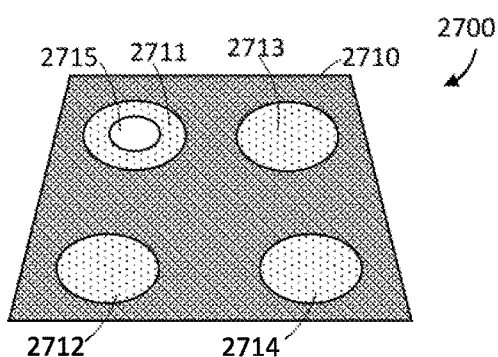
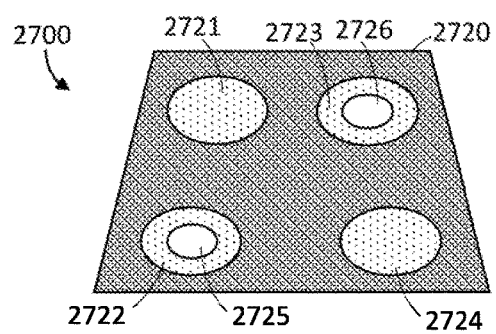
Figure 27A
Figure 27B

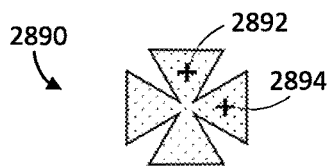
Figure 28A
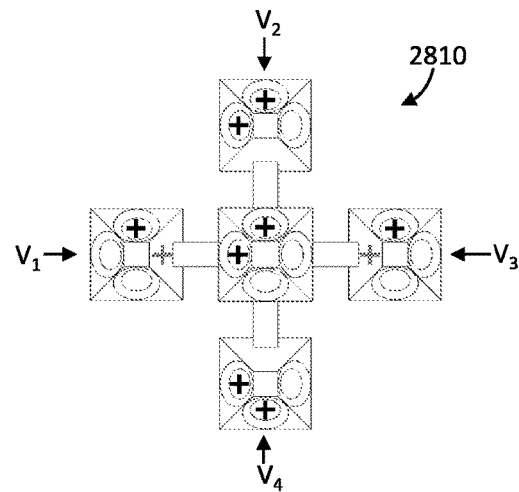
Figure 28B
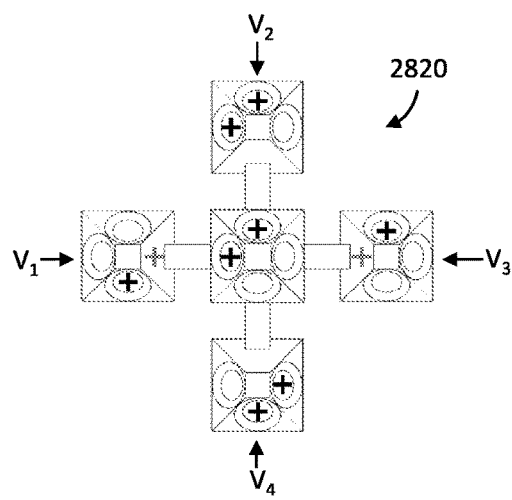
Figure 28C
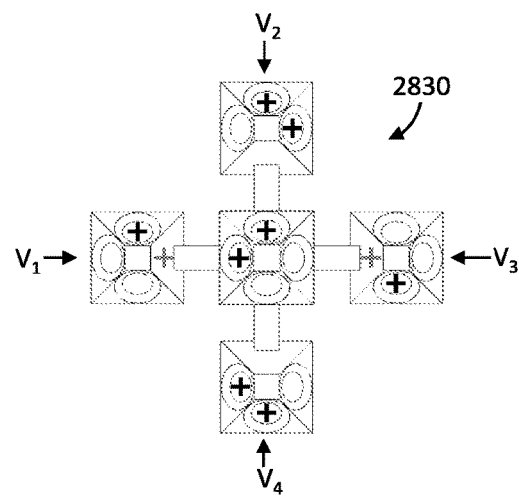
Figure 28D
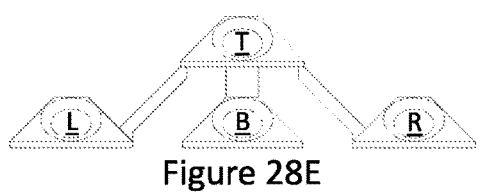
Figure 28E
| View | Marker 2810 | | | | Marker 2820 | | | | Marker 2830 | | | |
|---|---|---|---|---|---|---|---|---|---|---|---|---|
| | T | B | L | R | T | B | L | R | T | B | L | R |
| $V_1$ | ⊕ | ○ | ⊕ | ⊕ | ⊕ | ○ | ⊕ | ○ | ⊕ | ○ | ○ | ⊕ |
| $V_2$ | ⊕ | ⊕ | ⊕ | ⊕ | ⊕ | ⊕ | ⊕ | ○ | ⊕ | ⊕ | ○ | ⊕ |
| $V_3$ | ○ | ○ | ○ | ○ | ○ | ○ | ⊕ | ○ | ○ | ○ | ○ | ⊕ |
| $V_4$ | ○ | ⊕ | ○ | ○ | ○ | ⊕ | ⊕ | ○ | ○ | ⊕ | ○ | ⊕ |
Figure 28F

OPTICALLY DETECTABLE MARKERS FOR TRACKING, AND METHODS FOR MANUFACTURING, ASSEMBLING, AND USING THE SAME

CROSS-REFERENCE

The present application is a continuation-in-part of application PCT/CA2021/051550, filed Nov. 2, 2021, the entire contents of which are incorporated by reference. Application PCT PCT/CA2021/051550 claims the benefit of U.S. Provisional Patent Application No. 63/109,017, filed Nov. 3, 2020, the entire disclosure of which is incorporated herein by reference.

FIELD OF THE INVENTION

The present disclosure relates to surgical tracking, and in particular relates to markers used in tracking, as well as methods for assembling and using such markers.

BACKGROUND

During a procedure, such as a surgical procedure, it can be desirable to register, detect, localize, and/or track various elements. Such elements include, for example, anatomy of a patient, or tools used during the surgery. Such tracking entails positioning a marker having predetermined geometry on the element to be tracked, capturing image data representing the marker, and determining a pose (location and orientation) of the marker, or of the element relative to the marker by a tracking system.

Existing tracking technology has a number of problems and insufficiencies. For example, existing markers are easily soiled, difficult to set up and use, and have limited viewing angles.

The markers, cartridges, and methods described herein are not limited to surgical applications, but rather can be used in any appropriate application.

SUMMARY

Provided are optically detectable markers for tracking, as well as related methods. A marker can comprise a mask unit and a (removable) cartridge comprising an optically detectable surface exposed through at least three faces of the mask unit. Respective materials present a measurable contrast under optical detection conditions. An optical detectable surface can be detectable using IR and a contrasting surface is not. Faces can define openings to the cartridge. The cartridge can comprise a sheet of (optically detectible) material foldable to fit into the mask unit. A sheet can provide multiple connected cartridges (e.g. to fit into multiple connected mask units). Securing devices, including any of a support unit, a clip, a magnet, an adhesive, etc., can secure a cartridge in a mask unit. A marker, or maker kit, may comprise a plurality of mask units and cartridges connected via a marker body. Some of the mask units may be on different planes in such a marker.

According to a broad aspect, the present disclosure describes a marker for use in optical tracking, the marker comprising: a mask unit including at least three faces, the at least three faces defining an interior volume of the mask unit, each face having at least one opening therethrough to the interior volume of the mask unit, free ends of the at least three faces defining a cartridge receiving aperture to the interior volume of the mask unit; and a cartridge insertable into the interior volume of the mask unit through the aperture, a surface of the cartridge exposed through each of the at least one openings, the cartridge being optically detectable relative to the mask unit.

The at least three faces of the mask unit may include at least four faces, or may include at least eight faces. The mask unit may include a front face adjacent to the at least three faces, opposite the aperture. The front face may be parallel to the aperture. The front face may have at least one opening therethrough to the interior volume of the mask unit. The at least one opening of each face may include at least four openings, or may include at least five openings. The at least five openings of each face may be positioned according to a unique pattern which is different from position patterns of openings of other faces.

The cartridge may be a foldable planar sheet which includes at least three regions, each region corresponding to a face of the mask unit, the sheet foldable at boundaries between adjacent regions to fit in the interior volume of the mask unit and be exposed through the at least one opening on the at least three faces of the mask unit.

The marker may further comprise a support unit insertable into the interior volume of the mask unit with the cartridge to secure the cartridge in the interior volume of the mask unit. The support unit may secure the cartridge in the interior volume of the mask unit with one or more of a magnet, a clip, adhesive, or a friction fit. The cartridge may be secured in the interior volume of the mask unit by one or more of a magnet, a clip, adhesive, or a friction fit. The cartridge may have a shape which matches a shape of the interior volume of the mask unit.

The exposed surface of the cartridge may be reflective of light, and an exterior surface of the mask unit may be non-reflective of light. The exposed surface of the cartridge may be retroreflective. The exposed surface of the cartridge may be non-reflective of light, and an exterior surface of the mask unit may be reflective of light. The cartridge may have an optically non-detectable pattern or a hole therethrough to align with and be exposed through a respective opening of the at least one opening of the at least three faces of the mask unit.

The marker may further comprise a light source to emit light within the interior volume of the mask unit, the mask unit may comprise an opaque material, the cartridge may comprise a partially transparent diffusive material, the cartridge to receive the light from the light source, and diffuse at least a portion of the light through the cartridge. The light source may be positioned within the interior volume of the mask unit. The light source may be positioned external to the mask unit, the marker may further comprise a light director to direct light from the light source to the interior volume of the mask unit. The light director may comprise an optical fiber or a light pipe.

The marker may comprise a plurality of mask units and a plurality of cartridges, wherein: the mask unit is one of the plurality of mask units and the cartridge is one of the plurality of cartridges; each other mask unit of the plurality of mask units includes at least three faces, at least one face of each other mask unit having at least one opening therethrough to an interior volume of the respective mask unit, free ends of the at least three faces of each other mask unit defining a cartridge receiving aperture to the interior volume of the respective mask unit; and each cartridge of the plurality of cartridges is insertable into the interior volume of a respective mask unit though the cartridge receiving aperture therein, a surface of the respective cartridge exposed through each of the at least one openings in the respective mask unit, each cartridge being optically detectable relative to the plurality of mask units.

According to another broad aspect, the present disclosure describes a marker comprising: a marker body including a plurality of mask units, each mask unit including at least three faces defining an interior volume of the respective mask unit, at least one face of each mask unit having at least one opening therethrough to the interior volume of the respective mask unit, free ends of the at least three faces of the respective mask unit defining a cartridge receiving aperture to the interior volume of the mask unit; and a plurality of cartridges, each cartridge insertable into the interior volume of one of the mask units through the aperture therein, a surface of the respective cartridge exposed through each of the at least one openings in the respective mask unit, each cartridge being optically detectable relative to the plurality of mask units.

The at least three faces of each mask unit include at least four faces. The plurality of mask units may include four mask units. Three of the four mask units may be positioned spatially separated from each other in a first plane, and the fourth mask unit may be positioned in a second plane spatially separated from the first plane.

The plurality of mask units may include five mask units. Four of the five mask units may be positioned spatially separated from each other in a first plane, and the fifth mask unit may be positioned in a second plane spatially separated from the first plane.

Each mask unit of a first subset of the plurality of mask units may have an optically detectable identifier positioned thereon. Each mask unit of a second subset of the plurality of mask units may have an optically non-detectable identifier positioned thereon, the first and second subsets being non-overlapping subsets. The first and second subsets together may include the entire plurality of mask units. Each optically detectable identifier and each optically non-detectable identifier may be positioned on the respective mask unit adjacent each face of the at least three faces of the mask unit. A second subset of the plurality of mask units may have no optically detectable identifier positioned thereon, the first and second subsets being non-overlapping subsets which together include the entire plurality of mask units.

Each cartridge may be a foldable planar sheet which includes at least three regions, each region corresponding to a face of a respective mask unit of the plurality of mask units, the sheet foldable at boundaries between adjacent regions to fit in the interior volume of the respective mask unit and be exposed through the at least one opening on the at least three faces of the respective mask unit. Each cartridge, when folded, may be sized to fit in the interior volume of any one of the plurality of mask units.

The marker may further comprise a plurality of support units, each support unit insertable into the interior volume of a respective mask unit with one cartridge of the plurality of cartridges to secure the one cartridge in the interior volume of the respective mask unit. The support units may secure the cartridges in the interior volume of respective mask units with one or more of a magnet, a clip, adhesive, or a friction fit. The cartridges may be secured in the interior volume of respective mask units by one or more of magnets, clips, adhesive, or friction fit. Each cartridge may have a shape which matches a shape of the interior volume of each mask unit.

The exposed surface of each cartridge may be reflective of light, and an exterior surface of each mask unit may be non-reflective of light. The exposed surface of each cartridge may be retroreflective. The exposed surface of each cartridge may be non-reflective of light, and an exterior surface of each mask unit may be reflective of light. Each cartridge may have an optically non-detectable pattern or hole therethrough to align with and be exposed through a respective opening of the at least one opening of a respective mask unit.

The marker may further comprise at least one light source, the at least one light source to emit light within the interior volume of each mask unit, each mask unit may comprise an opaque material, each cartridge may comprise a partially transparent diffusive material, each cartridge to receive the light from the at least one light source, and diffuse at least a portion of the light which passes through the cartridge. The at least one light source may comprise a plurality of light sources, each mask unit having a respective one light source of the plurality of light sources positioned in the interior volume therein. The at least one light source may be positioned external to each mask unit, the marker may further comprise a light director to direct light from the at least one light source to the interior volume of each mask unit. The light director may comprise a plurality of optical fibers or light pipes, each of the optical fibers or light pipes to direct light from the at least one light source to the interior volume of a respective mask unit.

The marker body may be a monolithic body including each mask unit of the plurality of mask units. Each mask unit may be separately formed, and the marker body may be an assembly of the plurality of mask units coupled together with connectors.

According to another broad aspect, the present disclosure describes a marker for use in optical tracking, the marker comprising a mask unit including at least three faces, the at least three faces defining an interior volume of the mask unit, each face having at least one opening therethrough to the interior volume of the mask unit, free ends of the at least three faces defining a cartridge receiving aperture to the interior volume of the mask unit, the interior volume of the mask unit sized and dimensioned to receive a cartridge insertable into the interior volume of the mask unit through the aperture, the cartridge to be exposed through each of the at least one openings in the mask unit and optically detectable relative to the mask unit.

The at least three faces of the mask unit may include at least four faces or may include at least eight faces. The mask unit may include a front face adjacent to the at least three faces, opposite the aperture. The front face may be parallel to the aperture. The front face may have at least one opening therethrough to the interior volume of the mask unit. The at least one opening of each face may include at least four openings or may include at least five openings. The at least five openings of each face may be positioned according to a unique pattern which is different from position patterns of openings of other faces.

The marker may further comprise a support unit insertable into the interior volume of the mask unit with the cartridge to secure the cartridge in the interior volume of the mask unit. One of the mask unit or the support unit may include ferromagnetic material, and the other one of the mask unit or the support unit may include at least one magnet to secure the support unit and the cartridge in the interior volume of the mask unit by magnetic force with the ferromagnetic material. The support unit and the mask unit may each include at least one magnet to together secure the support unit and the cartridge in the interior volume of the mask unit. The mask unit and the support unit may comprise complimentary clips to secure the support unit and the cartridge in the interior volume of the mask unit. The mask unit may include at least two clips to secure the cartridge in the interior volume of the mask unit. The marker may further comprise an adhesive to secure the cartridge in the interior volume of the mask unit.

Each face of the at least three faces of the mask unit may be non-reflective of light. The marker may further comprise a light source, the light source to emit light within the interior volume of the mask unit. The light source may be positioned within the interior volume of the mask unit. The light source may be positioned external to the mask unit, the marker may further comprise a light director to direct light from the light source to the interior volume of the mask unit. The light director may comprise an optical fiber or a light pipe.

The marker may comprise a plurality of mask units, wherein: the mask unit is one of the plurality of mask units; each other mask unit of the plurality of mask units includes at least three faces, at least one face of each other mask unit having at least one opening therethrough to an interior volume of the respective mask unit, free ends of the at least three faces of each other mask unit defining a cartridge receiving aperture to the interior volume of the respective mask unit; and the interior volume of each mask unit is sized and dimensioned to receive a respective cartridge through the aperture, the respective cartridge to be exposed through each of the at least one openings in the respective mask unit and be optically detectable relative to the mask unit.

According to another broad aspect, the present disclosure describes a marker comprising a marker body including a plurality of mask units, each mask unit including at least three faces defining an interior volume of the respective mask unit, at least one face of each mask unit having at least one opening therethrough to the interior volume of the respective mask unit, free ends of the at least three faces of the respective mask unit defining a cartridge receiving aperture to the interior volume of the respective mask unit, wherein, for each mask unit: the interior volume of the mask unit is sized and dimensioned to receive a respective cartridge insertable into the interior volume of the mask unit through the aperture of the mask unit, the cartridge to be exposed through each of the at least one openings in the mask unit and optically detectable relative to the mask unit.

The at least three faces of each mask unit may include at least four faces. The plurality of mask units may include four mask units. Three of the four mask units may be positioned spatially separated from each other in a first plane, and the fourth mask unit may be positioned in a second plane spatially separated from the first plane. The plurality of mask units may include five mask units. Four of the five mask units may be positioned spatially separated from each other in a first plane, and the fifth mask unit may be positioned in a second plane spatially separated from the first plane.

Each mask unit of a first subset of the plurality of mask units may have an optically detectable identifier positioned thereon. Each mask unit of a second subset of the plurality of mask units may have an optically non-detectable identifier positioned thereon, the first and second subsets being non-overlapping subsets. The first and second subsets together may include the entire plurality of mask units. Each optically detectable identifier and each optically non-detectable identifier may be positioned on the respective mask unit adjacent each face of the at least three faces of the mask unit. A second subset of the plurality of mask units may have no optically detectable identifier positioned thereon, the first and second subsets being non-overlapping subsets which together include the entire plurality of mask units.

The marker may further comprise a plurality of support units, each support unit insertable into the interior volume of a respective mask unit to secure a cartridge in the interior volume of the respective mask unit. Each support unit may be sized to fit in the interior of any one of the plurality of mask units with a cartridge. For each mask unit and support unit insertable therein, one of the mask unit or the support unit may include ferromagnetic material, and the other one of the mask unit or the support unit may include at least one magnet to secure the support unit and the cartridge in the interior volume of the mask unit by magnetic force with the ferromagnetic material. For each mask unit and support unit insertable therein, the support unit and the mask unit may each include at least one magnet to together secure the support unit and the cartridge in the interior volume of the mask unit. For each mask unit and support unit insertable therein, the mask unit and the support unit may comprise complimentary clips to secure the support unit and the cartridge in the interior volume of the mask unit. Each mask unit may include at least two clips to secure a cartridge in the interior volume of the mask unit.

Each face of the at least three faces of each mask unit may be non-reflective of light. The marker may further comprise at least one light source, the at least one light source to emit light within the interior volume of each mask unit. The at least one light source may comprise a plurality of light sources, each mask unit to receive a respective one light source of the plurality of light sources in the interior volume therein. The at least one light source may be positioned external to each mask unit, the marker may further comprise a light director to direct light from the at least one light source to the interior volume of each mask unit. The light director may comprise a plurality of optical fibers or light pipes, each of the optical fibers or light pipes to direct light from the at least one light source to the interior volume of a respective mask unit.

The marker body may be a monolithic body including each mask unit of the plurality of mask units. Each mask unit may be separately formed, and the marker body may be an assembly of the plurality of mask units coupled together with connectors.

According to another broad aspect, the present disclosure describes an optically detectable cartridge for use in an optical marker, the optical marker including a mask unit having at least three faces, the at least three faces defining an interior volume of the mask unit, each face having at least one opening therethrough to the interior volume of the mask unit, free ends of the at least three faces defining a cartridge receiving aperture to the interior volume of the mask unit, the cartridge comprising: a planar sheet of optically detectable material, wherein: the sheet includes at least three regions corresponding to faces of the mask unit; the sheet is foldable at boundaries between adjacent regions; and the cartridge is sized and dimensioned, when folded at the boundaries, to fit into the interior volume of the mask unit through the aperture and be exposed through the at least one opening on the at least three faces of the mask unit.

The planar sheet of optically detectable material may include a central region, and the at least three regions may include at least three spoke regions extending from the central region, the number of spoke regions being equal to the number of faces of the mask unit; and the sheet may be foldable at a boundary between each spoke region and the central region. Each boundary between adjacent regions may be weakened along a fold line. Prior to folding, the spoke regions may be separated from each other by gaps in the sheet. Prior to folding the spoke regions may be separated from each other by collapsible regions of the sheet, the sheet being foldable at boundaries between each of the collapsible regions and spoke regions. The collapsible regions of the sheet may be foldable regions, boundaries between spoke regions and the central region may be weakened along a first set of fold lines, boundaries between spoke regions and foldable regions may be weakened along a second set of fold lines, and each foldable region may be weakened along at least one other fold line through the foldable region.

At least one region may have a hole therethrough or an optically non-detectable pattern thereon to align with a respective opening of the mask unit when the cartridge is positioned in the mask unit. The cartridge may comprise at least one alignment feature to align with a respective alignment feature of the mask unit.

According to another broad aspect, the present disclosure describes a method of manufacturing a cartridge, comprising: providing a planar sheet of optically detectable material; defining at least three regions in the sheet, each region corresponding to a face of the mask unit into which the cartridge is to be inserted; and weakening each boundary between adjacent regions.

According to another broad aspect, the present disclosure describes a method of manufacturing a cartridge, comprising: providing a planar sheet of optically detectable material; defining a central region and at least three spoke regions extending from the central region in the sheet; and cutting away wedges of the sheet positioned between adjacent spoke regions. The method may further comprise weakening each boundary between a spoke region and the central region.

According to another broad aspect, the present disclosure describes a method of manufacturing a cartridge, comprising: providing a planar sheet of optically detectable material; defining in the sheet a central region and at least three spoke regions extending from the central region; defining in the sheet collapsible regions extending from the central region between the spoke regions; weakening each boundary between a spoke region and the central region; and weakening each boundary between a spoke region and a collapsible region. The method may further comprise weakening each collapsible region along at least one line which runs through the collapsible region.

According to another broad aspect, the present disclosure describes a method comprising: providing a mask unit, the mask unit including at least three faces which define an interior volume of the mask unit, each face having at least one opening therethrough to the interior volume of the mask unit, free ends of the at least three faces defining a cartridge receiving aperture to the interior volume of the mask unit; receiving an optically detectable cartridge in the interior volume of the mask unit through the aperture, with an external surface of the cartridge exposed through each of the at least one opening; and securing the cartridge in the interior volume of the mask unit.

The method may further comprise: detecting, by an image sensor, the cartridge through the at least one opening on at least one of the at least three faces; and determining a pose of the mask unit by identifying a position and orientation of the at least one opening through which the cartridge is exposed. The method may further comprise: lighting, by a light source, the mask unit and cartridge; and tracking, by a computing device, a pose of the mask unit during a procedure. Securing the cartridge in the interior volume of the mask unit may comprise receiving a support unit in the interior volume of the mask unit through the aperture. The method may further comprise receiving a light source in the interior volume of the mask unit through the aperture after receiving the optically detectable cartridge. The method may further comprise: providing a light source; and connecting the light source to the interior volume of the mask unit by a light director.

Providing the mask unit may comprise providing a plurality of mask units, each mask unit including at least three faces, each face having at least one opening open to an interior volume of the respective mask unit, each of the at least three faces of each mask unit adjacent an aperture of the respective mask unit open to the interior volume of the respective mask unit. Receiving an optically detectable cartridge may comprise receiving a respective optically detectable cartridge in the interior volume of each mask unit through the aperture therein, with an external surface of the respective cartridge exposed through any openings in the respective mask unit. Securing the cartridge may comprise securing each cartridge in the interior volume of the respective mask unit. The method may further comprise: detecting, by the image sensor, at least two cartridges through openings on at least two mask units; and determining a pose of the mask units by identifying a position and orientation of the openings through which the cartridges are exposed.

According to another broad aspect there is provided an optical marker kit. In an embodiment, the optical marker kit comprises: a marker body comprising a plurality of mask units spaced from one another and connected by mask unit connectors, each mask unit including at least three faces defining an interior volume of the respective mask unit, at least one face of each mask unit having at least one opening therethrough to the interior volume of the respective mask unit, free ends of the at least three faces of the respective mask unit defining a cartridge receiving aperture to the interior volume of the mask unit; and a connected cartridge assembly comprising a plurality of cartridges spaced from one another and connected by cartridge connectors, each cartridge insertable into the interior volume of one of the mask units through the aperture therein, a surface of a respective cartridge exposed through each of the at least one openings in a respective mask unit into which the respective cartridge is inserted, each cartridge being optically detectable relative to the plurality of mask units.

In an embodiment of the marker kit, the at least three faces of each mask unit include at least four faces. In an embodiment, the plurality of mask units includes four mask units; and three of the four mask units are positioned spatially separated from each other in a first plane, and the fourth mask unit is positioned in a second plane spatially separated from the first plane.

In an embodiment of the marker kit, the plurality of mask units includes five mask units; and four of the five mask units are positioned spatially separated from each other in a first plane, and the fifth mask unit is positioned in a second plane spatially separated from the first plane.

In an embodiment of the marker kit, each mask unit of a first subset of the plurality of mask units has an optically detectable identifier positioned thereon. In an embodiment of the marker kit, each mask unit of a second subset of the plurality of mask units has an optically non-detectable identifier positioned thereon, the first and second subsets being non-overlapping subsets. In an embodiment of the marker kit, each optically detectable identifier and each optically non-detectable identifier are positioned on the respective mask unit adjacent each face of the at least three faces of the mask unit. In an embodiment of the marker kit, a second subset of the plurality of mask units has no optically detectable identifier positioned thereon, the first and second subsets being non-overlapping subsets which together include the entire plurality of mask units.

In an embodiment of the marker kit, each of the cartridges comprises a foldable planar sheet which includes at least three regions, the sheet foldable at boundaries between adjacent regions to define cartridge faces for each of at least three of the faces of each mask unit and to fit in the interior volume of the respective mask unit and be exposed through the at least one opening on the at least three faces of the respective mask unit. In an embodiment of the marker kit, the plurality of cartridges and the cartridge connectors are formed from a single foldable planar sheet to provide the connected cartridge assembly as a monolithic body. In an embodiment of the marker kit, the at least three regions for each of the cartridges define a central region and a plurality of spoke regions, wherein each respective spoke region is adjacent to and extending from the central region; and the boundaries between adjacent regions are weakened along respective fold lines. In an embodiment of the marker kit, either a) the plurality of spoke regions provides one spoke region for each face of the mask unit into which the respective cartridge is to be inserted; or b) the plurality of spoke regions provided is one fewer than the number of faces of the mask unit into which the respective cartridge is to be inserted. In an embodiment of the marker kit, the sheet is formed to provide separation between the spoke regions by gaps in the sheet. In an embodiment of the marker kit, each of the cartridges comprises at least one alignment feature to align with respective alignment features of the respective mask units into which the cartridges are to be inserted. In an embodiment of the marker kit, the plurality of cartridges and the cartridge connectors are formed from a single foldable planar sheet to provide the connected cartridge assembly as a monolithic body, and the cartridge connectors comprise respective connector fold lines, and, when the connected cartridge assembly is folded along the boundary fold lines and the connector fold lines, at least three of the plurality of cartridges are positioned spatially separated from each other in a first plane, and at least one other cartridge of the plurality of cartridges is positioned in a second plane spatially separated from the at least three cartridges of the first plane. In an embodiment of the marker kit, the plurality of mask units comprises either four mask units or five mask units.

In an embodiment of the marker kit, the cartridges are secured in the interior volume of respective mask units by one or more of magnets, clips, adhesive, or friction fit.

In an embodiment of the marker kit, each of the cartridges has a shape which matches a shape of the interior volume of each mask unit.

In an embodiment of the marker kit, one of a) the exposed surface of each of the cartridges is reflective of light, and an exterior surface of each mask unit is non-reflective of light; or b) the exposed surface of each cartridge is non-reflective of light, and an exterior surface of each mask unit is reflective of light.

The marker kit of claim 1, wherein each of the cartridges has an optically non-detectable pattern or provides a hole therethrough to align with and be exposed through a respective opening of the at least one opening of a respective mask unit.

These and other broad aspects and embodiments will be apparent to a person of ordinary skill in the art.

BRIEF DESCRIPTION OF THE FIGURES

FIGS. 2A and 2B are different isometric views, and FIG. 2C is a side view of the marker, in accordance with the prior art.

FIGS. 4A and 4B are isometric views, FIG. 4C is a front view, FIG. 4D is a side view, and FIG. 4E is a rear view of the marker.

FIGS. 6A and 6C are side cross-sectional views of an optically detectable material, which show viewable angles of the material.

FIG. 6B illustrates a retroreflectivity profile of an exemplary material.

FIGS. 7A and 7B are isometric views of the marker. FIG. 7C is a front view of the marker. FIG. 7D is a side view of the marker. FIG. 7E is a rear view of the marker.

FIGS. 8A and 8B are isometric views of the marker. FIG. 8C is a front view of the marker. FIG. 8D is a side view of the marker. FIG. 8E is a rear view of the marker.

FIGS. 10A and 10B are isometric views of the marker. FIG. 10C is a front view of the marker. FIG. 10D is a side view of the marker. FIG. 10E is a rear view of the marker.

FIGS. 11A and 11B are isometric views of the marker. FIG. 11C is a front view of the marker. FIG. 11D is a side view of the marker. FIG. 11E is a rear view of the marker. FIG. 11F is a front view of the marker, including an extension coupled thereto.

FIG. 12A is a front view, and FIGS. 12C, 12F, and 12I are side views with optically detectable identifiers positioned thereon. FIG. 12B is a front view, and FIGS. 12D, 12G, and 12J are side views with optically detectable identifiers and optically non-detectable identifiers positioned thereon. FIGS. 12E, 12H, and 12K are side views of the markers in FIGS. 12A-12D, 12F-12G, and 12I-12J, as seen by an image sensor.

FIGS. 13A and 13B are isometric views of the marker. FIG. 13C is a front view of the marker. FIG. 13D is a side view of the marker. FIG. 13E is a rear view of the marker.

FIGS. 25A, 25B, 25C, 26A, 26B, 26C, and 27A-27B are side views of exemplary mask units and cartridges, the cartridges having patterns aligned with openings of the mask units. FIGS. 25C and 26C illustrate the mask units and cartridges as seen by an image sensor.

FIGS. 28A, 28B, 28C, 28D, 28E, and 28F illustrate unique identification of markers based on cartridge patterns aligned with openings of mask units of the markers.

DETAILED DESCRIPTION

The description herein details several exemplary embodiments. One skilled in the art will appreciate that it is within the scope of the present disclosure to combine individual embodiments with other embodiments as appropriate.

Figure 1:
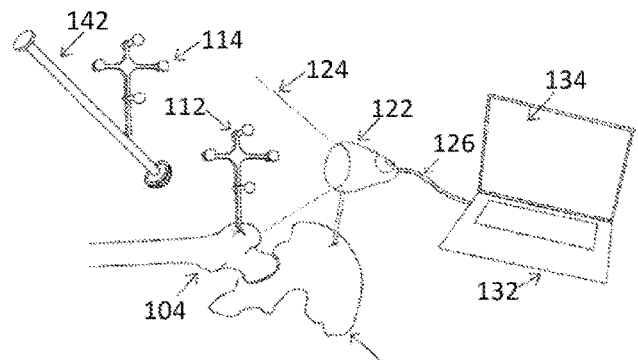
FIG. 1 illustrates an exemplary scenario in which markers described herein can be used.

FIG. 1 illustrates an exemplary scenario in which a surgical procedure is being performed. In the example of FIG. 1, a total hip arthroplasty (THA) is being performed, but the discussion herein is applicable to any surgical procedure where a tracking system is used, or any appropriate procedure other than surgery. In FIG. 1, a patient's pelvis 102 and femur 104 are shown. A marker 112 is positioned on (e.g. affixed to, mounted on, or touched against) femur 104. An image sensor 122 is positioned on pelvis 102. Image sensor 122 can capture image data over a field of view 124. Image sensor 122 can communicate captured image data to computing device 132. Image sensor 122 is shown as being communicatively coupled to computing device 132 by wire 126, but wireless communication between image sensor 122 and computing device 132 is also possible. Further, it is also possible for image sensor 122 and computing device 132 to be a unified device. Computing device 132 can analyze the image data (for example by at least one processor in computing device 132), or computing device 132 can send the data to a remote device or cloud server for analysis, to detect marker 112 and determine a pose (position and orientation) thereof. Pose can be position or orientation in three-dimensional space, though in certain applications pose can be position and orientation in two-dimensional space. Further, based on the pose and predetermined geometry of marker 112, computing device 132 can also determine a pose of elements which marker 112 is positioned on. In the example of FIG. 1, image sensor 122 can be affixed to pelvis 102, and marker 112 can be affixed to femur 104. Consequently, movement of marker 112 relative to image sensor 122 can correspond to movement of the femur 104 relative to pelvis 104. In this context, "tracking" an element can entail continuously, regularly, or intermittently determining a pose of the element.

FIG. 1 also illustrates marker 114 positioned on a tool 142. In the case of FIG. 1, tool 142 is a cup impactor for implanting a prosthetic hip cup during THA, but marker 114 can be positioned on any appropriate tool. Image sensor 122 can capture image data including marker 114, which can subsequently be analyzed by computing device 132 (or a remote analysis device as mentioned above) to determine pose information of tool 142. Marker 114 can be identical to marker 112, or marker 114 and marker 112 could be different (for example by having different geometry from each other). In some implementations, marker 112 could be removably positioned on a base mounted to femur 104, such that marker 112 can be removed from and replaced on femur 104 without affecting the positioning of marker 112 when positioned on femur 104. In such cases, marker 112 can be removed from the base, and positioned on other elements (such as tool 142), such that multiple tracking operations can be achieved with a single marker. In such implementations, the functionality of marker 114 could be achieved with marker 112.

Information based on the pose of an element of interest can be presented by display 134 of computing device 132 (or another device). This information can provide helpful or critical information to the surgeon. Further, other output means can also be used, such as audio output like speakers.

In order to accurately determine the pose of the anatomy (e.g. pelvis 102, femur 104) or the tool 142, registration steps can be performed to determine the geometry of the anatomy/tool relative to a marker. As non-limiting examples, steps such as probing the element with a marker, moving the element with the marker in the field of view of the image sensor, or registering additional information such as acceleration or gravity data using an accelerometer, can be performed.

FIG. 1 shows exemplary anatomy of pelvis 102 and femur 104. However, any appropriate anatomy can be tracked, including for example leg, arm, torso, head, back, or chest anatomy, including bones therein. As mentioned above, the markers discussed herein can also be used in non-surgical applications.

Throughout this disclosure, reference is made to a "tracking system". Such a tracking system can refer to a device such as computing device 132, or any other appropriate device capable of processing, which can receive data representing a marker, and determining a pose of the marker or pose of an element in contact with the marker. Broadly, a tracking system can also include an image sensor and a marker.

Figure 2A:
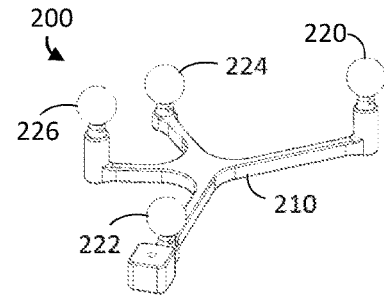
FIGS. 2A-2C illustrate a marker which suffers from occlusion, robustness, and usability issues.
Figure 2B:
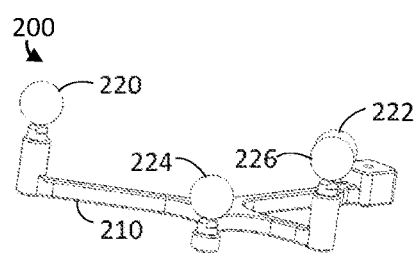
Figure 2C:
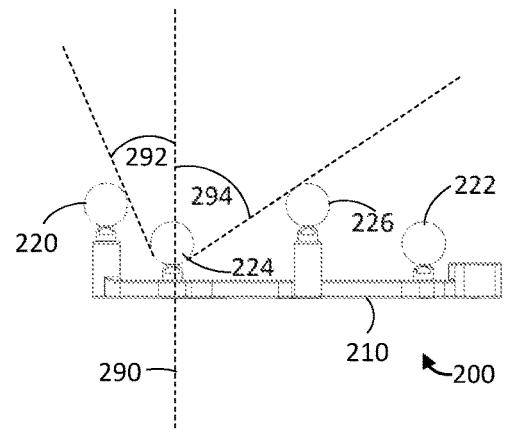

FIGS. 2A-2C illustrate an exemplary marker 200, according to the prior art.

FIG. 2A is an isometric view which shows marker 200 having marker body 210 and spheres 220, 222, 224, and 226. Marker body 210 can be of a specific geometry which holds spheres 220, 222, 224, and 226 in specific positions. By determining relative positioning of spheres 220, 222, 224, and 226, a tracking system can determine the pose of marker 200. However, marker 200 suffers from occlusion problems, which result in low viewing angles.

FIG. 2B is another view of marker 200 which illustrates an instance of occlusion. In particular, when viewed from the angle of FIG. 2B, sphere 226 occludes sphere 222. Consequently, pose determination of marker 200 from this angle may have reduced accuracy, or even be impossible.

FIG. 2C illustrates a side view of marker 200, which illustrates exemplary viewing angle limits before sphere 224 can be at least partially occluded. Relative to an axis 290 which is parallel to a direct viewing angle of marker 200 (a front view), the viewing angle can be at an angle 292 before sphere 220 begins to occlude sphere 224, and the viewing angle can be at an angle 294 before sphere 226 begins to occlude sphere 224. For the marker 200, angles 292 and 294 are each less than 90°, such that marker 200 will commonly occlude itself at beyond a relatively narrow viewing angle. FIG. 2C illustrates exemplary occlusion angles of sphere 224, but many other occlusion scenarios are possible. In view of the above, it is desirable to achieve markers with a greater range of viewing angles.

In addition to the above, marker 200 can be difficult to assemble and use. In particular, spheres 220, 222, 224, and 226 are disposable retro-reflective components, which are attached to marker body 210 for each surgery. Such attachment could include snapping interfaces, screw interfaces, or any other appropriate form of attachment. Such attachment can be cumbersome, painful, and prone to error.

Figure 3A:
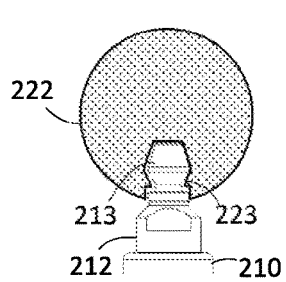
FIGS. 3A and 3B are side cross-sectional views of a detectable sphere used in the marker of FIGS. 2A-2C, in accordance with the prior art.
Figure 3B:
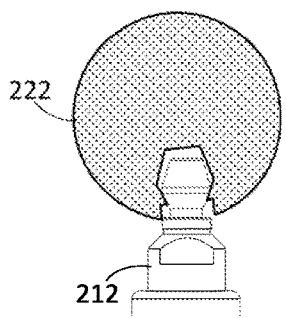

FIGS. 3A and 3B are side cross-sectional views of sphere 222, as attached to marker body 210 via post 212 in accordance with the prior art. The discussion of FIGS. 3A and 3B also applies to spheres 220, 224, 226. Sphere 222 includes a recess 223 which fits around a protrusion 213 of post 212. Recess 223 tapers inwards to fasten around protrusion 213. To attach sphere 222 to post 212, recess 223 is aligned over post 212, and significant downward force is applied to snap recess 223 into engagement with protrusion 213 as shown in FIG. 3A. This significant force can be difficult to apply, causing pain for the person applying the force, and risking damage to sphere 222. Further, the tight fit of sphere 222 to post 212 may catch a glove of the person installing the sphere between any of the interfaces between sphere 222 and post 212. The glove may be damaged or ripped, forcing the wearer to change gloves and potentially harming a sterile field for a surgery.

Further still, sphere 222 may end up misaligned on post 212, as is shown in FIG. 3B. In FIG. 3B, sphere 222 is not properly seated on post 212, which may result in the position of the sphere being inaccurate compared to the expected position of the sphere on the marker and relative to other spheres. Consequently, tracking of the sphere may be inaccurate. Such misalignment may not be readily detected by an operator until the surgical procedure is being performed, at which point it can be difficult to replace or reposition the sphere without soiling the sphere. Further, the sphere may be loose and fall off during a surgical procedure.

Additionally, soiling of spheres 220, 222, 224, and 226 in general can be a problem. In particular, the spheres may be retroreflective, and comprise a surface of microballs. Once a liquid, such as water or blood, gets on a sphere, capillary action between the microballs can make removal of the liquid difficult. Further, the presence of such liquid can harm the desired optical properties of the sphere, making tracking inaccurate or impossible.

As shown in FIGS. 3A and 3B, sphere 222 can be attached to marker body 210 via a post 212 (similar structures are also present for the other spheres 220, 224, and 226). The inclusion of three such coupled components can cause manufacturing or assembly errors to stack up, such that the position of each sphere can be significantly more inaccurate than desired.

In view of the above, it is desirable to achieve a marker which improves at least one of: efficacy (such as range of viewable angles); ease of assembly and use; resilience to soiling; cleanability; reduced manufacturing or assembly errors; and resilience to detection and tracking errors in general.

Figure 4A:
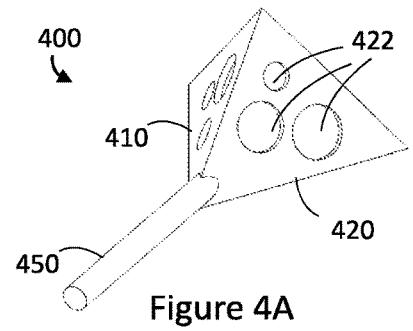
FIGS. 4A-4E illustrate an exemplary marker with three side faces.
Figure 4B:
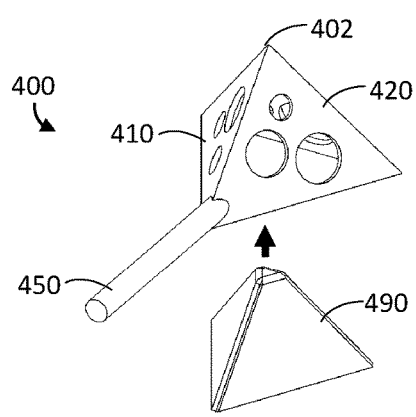
Figure 4C:
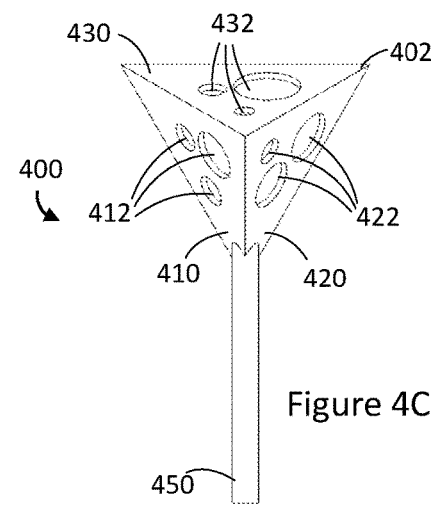
Figure 4D:
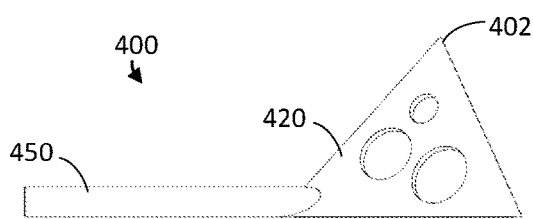
Figure 4E:
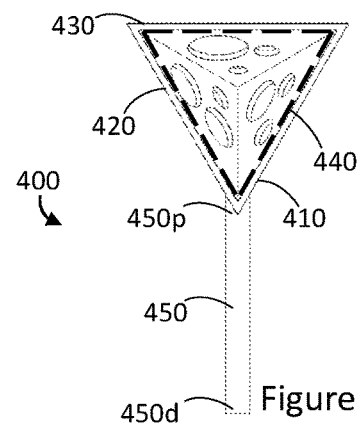

FIGS. 4A-4E illustrate an exemplary marker 400. FIGS. 4A and 4B are isometric views of the marker 400. FIG. 4C is a front view of marker 400. FIG. 4D is a side view of marker 400. FIG. 4E is a rear view of marker 400.

FIGS. 4A-4E illustrate marker 400 as having a mask unit 402 which includes three faces 410, 420, and 430, though additional faces are possible, as will be described later. The three faces 410, 420, and 430 are adjacent a cartridge receiving aperture 440 which is open to an interior volume of the mask unit, as shown accentuated by dashed lines in FIG. 4E. That is, the three faces 410, 420, and 430 define an interior volume of the mask unit 402, and free ends of faces 410, 420, and 430 define a cartridge receiving aperture 440 to the interior volume. Each of the faces includes at least one opening which opens to the interior volume of the mask unit 402. In the example of marker 400, face 410 has three openings 412 therethrough, face 420 has three openings 422 therethrough, and face 430 has three openings 432 therethrough. Each face can include more or fewer openings, as will be discussed later.

FIGS. 4A, 4C, and 4D show marker 400 as having an optically detectable cartridge positioned within the interior volume of the mask unit 402. As used herein, the term "optically detectable" means an element designed to be detectable by a tracking system. The optically detectable element will have high contrast compared to "optically non-detectable" elements, or other elements which may be seen by the tracking system. As used herein, the term "optically non-detectable" refers to elements which accentuate optically detectable elements, or prevent ambient light from interfering with optical detectability of other elements.

As an example, with reference to mask unit 402 and cartridge 490 (though the discussion is applicable to other mask units and cartridges discussed herein), a high contrast is desirable between the cartridge and the mask unit. That is, a high difference in optical detectability between cartridge and mask is desired. For example, one of the mask unit or the cartridge can be detectable by a tracking system with greater brightness than the other of the mask unit or the cartridge. In some implementations, the cartridge can comprise (be coated or formed of) material which is reflective of light, whereas the mask unit can comprise material which is non-reflective or absorptive of light. Exemplary materials for cartridges and mask units are discussed later. In such implementations, the cartridge will appear "bright" to the tracking system, whereas the mask unit will appear "dark". That is, the cartridge as viewed by a tracking system will have greater brightness than the mask unit. Implemented in the case of mask unit 402 and cartridge 490, a tracking system will see bright ellipses (corresponding to openings in the mask unit) over a dark background. In other implementations, the cartridge can comprise material which is non-reflective or absorptive of light, whereas the mask unit can comprise material which is reflective of light. Implemented in the case of mask unit 402 and cartridge 490, a tracking system will see a bright mask unit having dark ellipses therein (corresponding to openings in the mask unit). In each of these examples, the openings of the mask unit are clearly defined relative to the mask body. Additionally, by having the openings defined in a mask unit, the mask unit will block ambient light passing near the openings towards an image sensor of a tracking system, such that the effect of ambient light on optical detectability is reduced or eliminated.

Being optically detectable does NOT require that an element be particularly detectable to the human eye compared to other elements. Similarly, being optically non-detectable does NOT require features to be transparent, see-through, or otherwise invisible to the human eye. Optical detectability and non-detectability refer to detectability by a tracking system, which may be sensitive to wavelengths of light which do not completely overlap with the spectrum of light visible to the human eye. As a non-limiting example, some tracking systems may include an image sensor which captures infrared light, and optically detectable elements may be designed or tuned to emit or reflect infrared light so as to be easily seen by the tracking system. Detailed implementations of optically detectable cartridges are discussed later.

Unless context dictates otherwise, "optically detectable material" as used herein can refer to material which appears bright or dark to a tracking system, when contrasted against "optically non-detectable material" which appears dark or bright, respectively, to the tracking system.

Throughout this disclosure, the term "cartridge" refers to an "optically detectable cartridge", unless context requires otherwise. When an optically detectable cartridge is positioned within the interior volume of the mask unit, an optically detectable surface of the cartridge is exposed through each of the at least one openings.

FIG. 4E is a rear view of marker 400 which shows a cartridge receiving aperture 440 open to the interior volume of the mask unit 402, such that the optically detectable cartridge 490 can be inserted into the interior volume of the mask unit 402 through aperture 440. FIG. 4B shows optically detectable cartridge 490 prior to positioning within the interior volume of the mask unit 402.

FIGS. 4A-4E also illustrate an extension 450 coupled to the mask unit 402. In an embodiment, extension 450 is integrally formed with the mask unit 402, such that marker 400 is a monolithic mask unit and extension. That is, it is formed of a single (unitary) body or piece of a same material. Alternatively, extension 450 could be a separate component which is coupled to the mask unit 402, for example, by fasteners such as clips, screws, bolts, pins, or adhesive, or by processes such as welding, melting, or soldering. Such coupling could also be removable, such as a magnetic coupling. Any appropriate coupling between the extension 450 and the mask unit 402 could be used.

FIG. 4E annotates a first end 450p of the extension 450, proximal to the mask unit 402. FIG. 4E also annotates a second end 450d of the extension 450, distal from the mask unit 402. Extension 450 provides the ability to track elements which are distal from the mask unit 402. For example, extension 450 is a probe, such that an element to be tracked or localized is touched with the end 450d, and a tracking system analyzes the position of the mask unit, and determines the location of the probed element by calculating the position of end 450d based on a known geometrical relationship between the mask unit 402 and extension 450. As another example, marker 400 is mounted to an anatomy of a patient, such as a bone, via extension 450. In an example, such mounting is direct, such that extension 450 is directly mounted to the anatomy (e.g., end 450d could be a sharp end installed in a bone of the patient). In an example, such mounting is indirect; for example, a base or platform is installed on an anatomy of a patient, and the mask unit 402 is mounted to the base or platform (e.g. via extension 450). Such indirect mounting is particularly advantageous for achieving removable coupling between the anatomy and marker 400. In an example, extension 450 is removably coupled (e.g. with a magnetic coupling) to the base or platform mounted to the anatomy, such that marker 400 is removable from the anatomy, and subsequently replaceable on the anatomy, with a consistently defined relationship, since the base or platform is fixed to the anatomy.

Advantageously, including such an extension allows tracking of elements which may be difficult to track where the mask unit is required to directly contact the element (for example, a bone in an incision of a patient). Many of the exemplary markers discussed herein are not shown as including an extension like extension 450. However, any of the markers herein could have such an extension coupled thereto. Further, it is also possible for marker 400 to not include extension 450. Further still, any of the markers herein could include more than one extension.

Optically detectable cartridge 490 has an optically detectable surface facing external to the mask unit. Detailed implementations of cartridge are discussed below with reference to FIGS. 16A-25C, and include examples such as reflective or retroreflective material, or diffusive material with a light source providing light to the cartridge. The at least one opening in each face of the mask unit defines detectable features of the optically detectable surface; that is, the mask unit "masks" the optically detectable cartridge except for regions aligned with openings of the mask unit, to define optically detectable patterns which can be analyzed by a tracking system to determine a pose of the marker. In the example of FIGS. 4A-4E, each face has at least three openings thereon, to define a pattern of three regions of optically detectable material. In an embodiment, the pattern defined by each face is unique, so that a tracking system can determine which of the faces the image sensor is viewing. Further, although the openings are illustrated as being circular, other opening shapes are possible, as discussed later with reference to FIG. 15A. By knowing the geometry of the pattern defined by each face, the tracking system determines an orientation of the face, and consequently a pose of the marker. In some implementations, the tracking system first determines the orientation of a face, then determines which face the image sensor is viewing. Exemplary face patterns are discussed below with reference to FIGS. 15A-15I.

By including at least three faces, with at least one opening on each face, in an embodiment, the marker is localized and tracked by a single image sensor as long as a single face of the marker is visible to the image sensor. Consequently, marker 400 prevents self-occlusion, and is thus viewable from a greater range of viewing angles, as illustrated in FIGS. 5A and 5B.

Figure 5A:
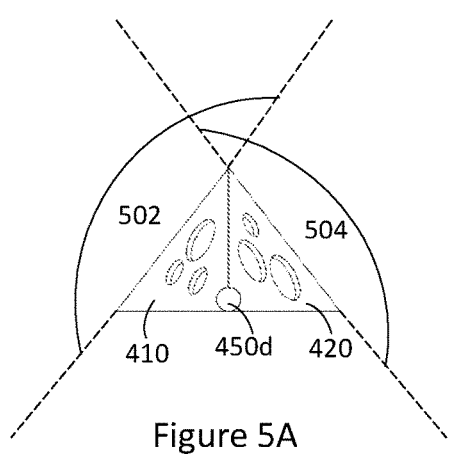
FIGS. 5A and 5B are a bottom view and front view, respectively, of the marker of FIGS. 4A-4E, showing viewable angles of the marker.

FIG. 5A is a bottom view of marker 400, and faces 410 and 420 visible. FIG. 5A illustrates an angular range 502 and an angular range 504. If an image sensor is positioned within angular range 502, face 410 will be visible to the image sensor. If the image sensor is positioned within angular range 504, face 420 will be visible to the image sensor. Since only one face is required for localization and tracking, even if the mask unit blocks one of the faces, at least one other face will be visible over a wide range of angles, and thus tracking can still be achieved. In the example of FIG. 5A, tracking can be achieved in the plane of the page over the range of angles which is the union of angular range 502 and angular range 504, which greatly exceeds 180°.

Figure 5B:
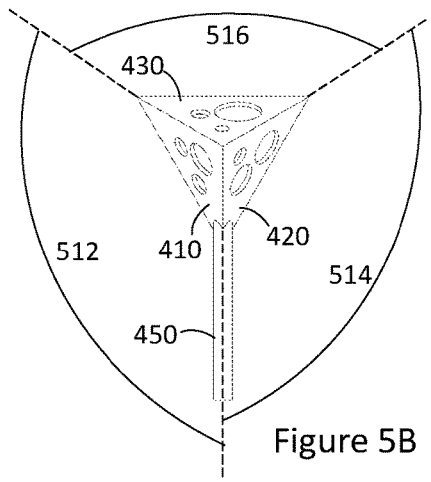

FIG. 5B is a front view of marker 400, with faces 410, 420, and 430 visible. FIG. 5B illustrates angular range 512, angular range 514, and angular range 516. If an image sensor is positioned within angular range 512, face 410 will be visible to the image sensor. If the image sensor is positioned within angular range 514, face 420 will be visible to the image sensor. If the image sensor is positioned within angular range 516, face 430 will be visible to the image sensor. In the example of FIG. 5B, tracking can be achieved in the plane of the page over the range of angles which is the union of angular range 512, angular range 514, and angular range 516, which is 360°. In FIG. 5B, visibility of each of the faces may extend beyond the angular ranges indicated; the boundaries between angular ranges shows the angle where a face which is at least steep angle to the image sensor changes. That is, the boundaries in FIG. 5B illustrates ranges over which a tracking system views and tracks specific faces, even if tracking of certain faces may be possible outside the shown angular ranges.

Based on FIGS. 5A and 5B it can be seen that marker 400 can achieve a wide range of viewing angles, including a large range in front of the marker (potentially extending partially towards a rear direction of the marker), and full range around the marker (above, below, left and right of the marker).

Despite the wide range of viewing angles achieved by the marker 400, in some scenarios this range of viewing angles is reduced because of other features of the marker, as discussed below with reference to FIGS. 6A-6C.

Figure 6A:
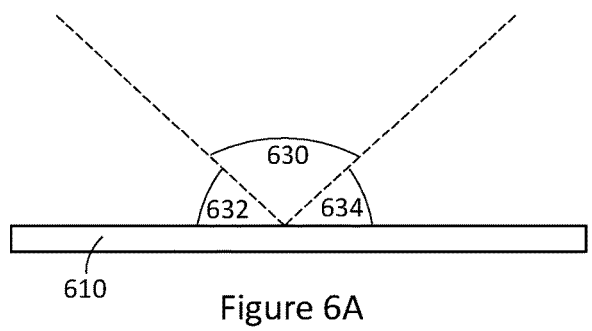
FIGS. 6A-6C illustrate constraints on viewing angles of markers.

FIG. 6A is a cross-sectional view of an optically detectable material 610, from which any of the cartridges discussed herein can be made. In the example of FIG. 6A, material 610 comprises retroreflective material, which redirects light impingent thereon back towards the origin of said light. For example, in a tracking setup, at least one light source is positioned proximal to an image sensor, such that at least one light source emits light towards a view captured by the image sensor. When retroreflective material is used in a cartridge of a marker, exposed regions of the cartridge redirect the light from the direction of the at least one light source back toward the image sensor. Such a setup results in highly detectable markers. However, retroreflective materials may only be effective over a limited range of angles. FIG. 6A illustrates an angular range 630, an angular range 632, and an angular range 634. When light is impingent on material 610 at an angle within range 630, the light is reflected with limited losses back towards its origin. When light is impingent on material 610 at an angle within angular range 632 or within angular range 634, the light may not be reflected back towards its origin, or may not be reflected back towards its origin with a desirable intensity (i.e. significant losses occur). Although FIG. 6A illustrates a distinct boundary between angular range 630 and angular ranges 632 and 634, the retroreflective performance of material 610 may reduce in a continuous or gradual manner as the direction of light incidence is further from normal to the material 310. In such a case, the boundaries between angular range 630 and angular ranges 632 and 634 may be the point at which retroreflective performance crosses a threshold of acceptability, which can be determined on a per-use basis. For some materials, such thresholds may be reached at angles of 60-70 degrees from normal to the material.

Figure 6B:
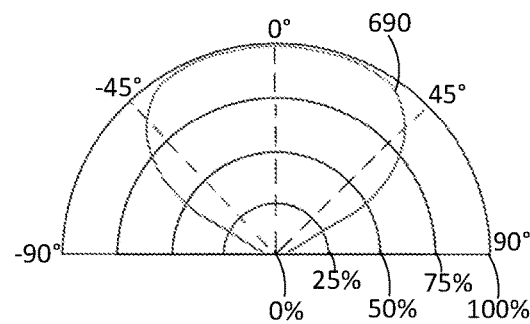

FIG. 6B illustrates a retroreflectivity profile of an exemplary material. In particular, FIG. 6B shows a retroreflective intensity curve 690, which indicates an intensity of retroreflected light as a percentage of incident light, based on the angle of incidence of the light from normal to the material. When the incidence angle is between −40° and 40°, the intensity of reflected light is nearly 100% of the intensity of the incident light. When the incidence angle is −45° or 45°, the intensity of reflected light is about 85-90% of the intensity of the incident light. As the incidence angle goes beyond −45° or 45°, intensity of reflected light sharply drops off, approaching 0% as incidence angle approaches 90°. Curve 690 and the numbers illustrated by FIG. 6B are merely illustrative, and other retroreflectivity curves are possible.

Such limitations on retroreflective performance can reduce viewing angles of surfaces in a marker, since even if a face is visible at a steep angle, retroreflective material of a cartridge in the marker may not have desirable performance at such a steep angle.

Figure 6C:
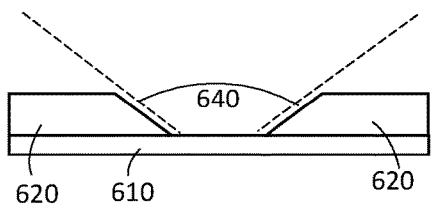

FIG. 6C is a cross-sectional view of an optically detectable material 610, from which any of the cartridges discussed herein can be made, and a mask unit 620 positioned thereon. The mask unit 620 has an opening therethrough (the open section between the illustrated regions of mask unit 620). The thickness of mask unit 620 and the shape of the opening may impact viewable angles of material 610. In particular, light which travels towards mask unit 620 and material 610 in FIG. 6C at a steep angle may not be able to impinge on material 610, because mask unit 620 at least partially blocks the opening at this steep angle. FIG. 6C shows an angular range 640, over which light can enter the opening and impinge on material 610. If a light source is outside of angular range 640, light from the light source will not impinge on the entirety of material 610, and thus a surface of a marker structure in accordance with FIG. 6C may not be trackable, because the openings may not be detectable in its entirety. In some implementations, a surface may be trackable based on partially visible openings; in such a case, angular range 640 could be wider, to the extent that light can impinge on a sufficiently large area of the opening.

In view of the above, even though marker 400 in FIGS. 4A-4E can achieve a good range of viewing angles, it may be desirable to increase the number of faces of the mask unit, to compensate for issues like those discussed with reference to FIGS. 6A-6C, and improve the probability that at least one face of the marker will be detectable.

Figure 7A:
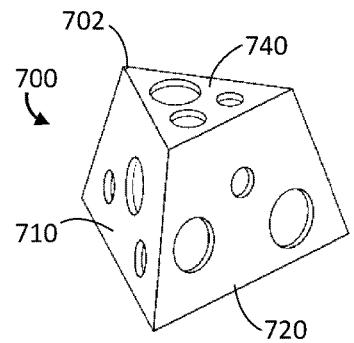
FIGS. 7A-7E illustrate an exemplary marker with three side faces and a front face.
Figure 7B:
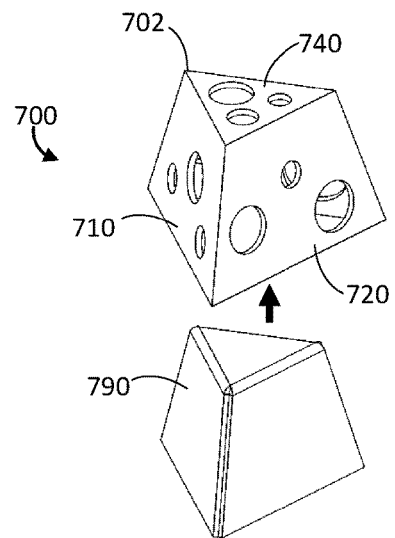
Figure 7C:
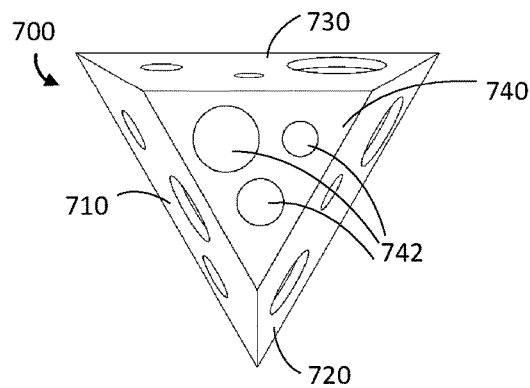
Figure 7D:
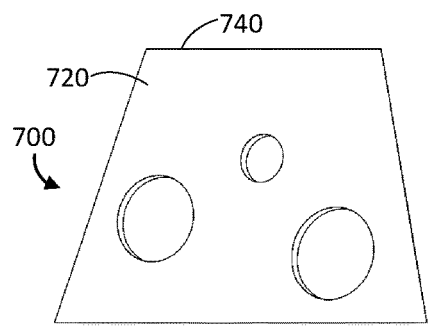
Figure 7E:
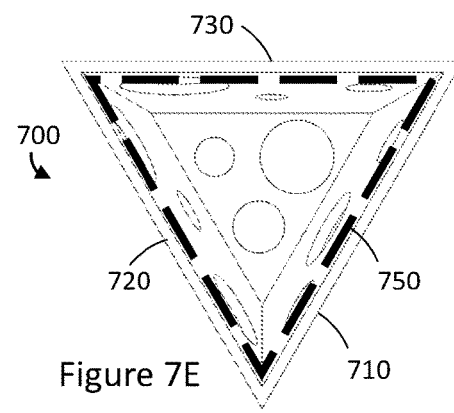

FIGS. 7A-7E illustrate an exemplary marker 700. FIGS. 7A and 7B are isometric views of the marker 700. FIG. 7C is a front view of marker 700. FIG. 7D is a side view of marker 700. FIG. 7E is a rear view of marker 700. Marker 700 can be similar to marker 400 discussed with reference to FIGS. 4A-4E. Unless context dictates otherwise, discussion of marker 400 is applicable to marker 700 and vice-versa.

Marker 700 includes a mask unit 702 having faces 710, 720, and 730, which, in an example, are similar to faces 410, 420, and 430 in marker 400. An optically detectable cartridge 790 can be positioned in an interior volume of marker 700, through an aperture 750 adjacent each of faces 710, 720, and 730, similar to cartridge 490 in marker 400. Detailed implementations of cartridge are discussed below with reference to FIGS. 16A-25C. Aperture 750 is shown accentuated by dashed lines in FIG. 7E. FIGS. 7A, 7C, and 7D show marker 700 with cartridge 790 positioned in the interior volume thereof.

One difference between marker 700 and marker 400 is that marker 700 is illustrated without an extension like extension 450 in marker 400 shown in FIGS. 4A-4E. In some implementations, marker 700 includes such an extension (or any other appropriate form of extension), but the extension is not shown in FIGS. 7A-7E to focus more on the features specific to marker 700.

Another difference between marker 700 and marker 400 is that marker 700 includes a front face 740, in addition to side faces 710, 720, and 730. As used throughout this disclosure, a "front" face of a mask unit can be a face which is opposite to a cartridge receiving aperture in the mask unit through which a cartridge is inserted (in the example of marker 700, front face 740 is opposite aperture 750). In contrast, "side" faces of a mask unit can be faces which are adjacent to said aperture (in the example of marker 700, side faces 710, 720, and 730 are positioned adjacent aperture 750; that is, the side faces 710, 720, and 730 define an interior volume of the mask unit 702, and free ends of faces 710, 720, and 730 define the cartridge receiving aperture 750 to the interior volume. Front face 740 has at least one opening 742 therein, such that an optically detectable surface of optically detectable cartridge 790 is exposed through the at least one opening 742. When viewing marker 700 from a frontal direction (such as the view in FIG. 7C), face 740 provides a trackable face which is relatively normal to the viewing direction, and thus has excellent trackability. In contrast, when viewing marker 400 from a frontal direction (such as the view shown in FIG. 4C), at least one of faces 410, 420, or 430 is used for tracking instead. However, these faces are at a relatively steep angle from normal to the viewing direction, and therefore may not be accurately trackable for the reasons discussed with reference to FIGS. 6A-6C. Consequently, having a front face such as front face 740 improves viewing angles and tracking effectiveness of the marker 700. Principles by which viewing angles are improved by adding faces are discussed in detail below with reference to FIGS. 9A-9F.

FIG. 7D shows a top edge of face 720 as being parallel to a bottom edge of face 720. This could be true for all side faces of marker 700, such that front face 740 is parallel to aperture 750. However, such parallelism is optional. Further, in any of the mask units described herein which include a front face, the front face is optionally parallel to the aperture.

Figure 8A:
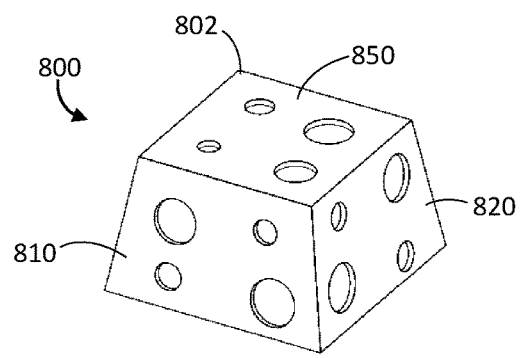
FIGS. 8A-8E illustrate an exemplary marker with four side faces.
Figure 8B:
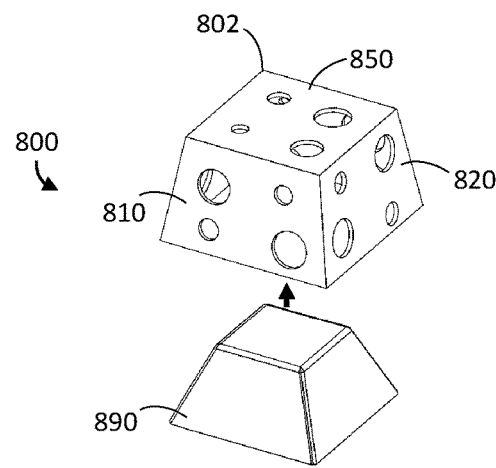
Figure 8C:
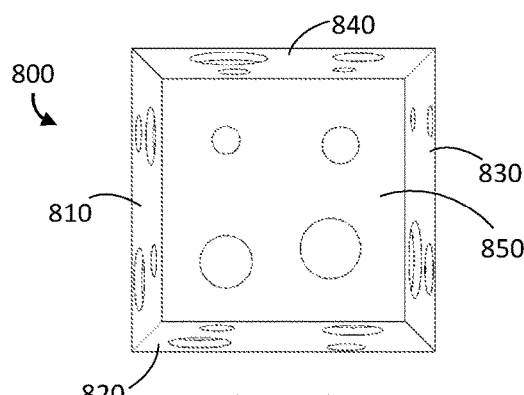
Figure 8D:
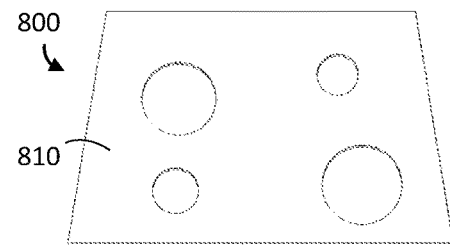
Figure 8E:
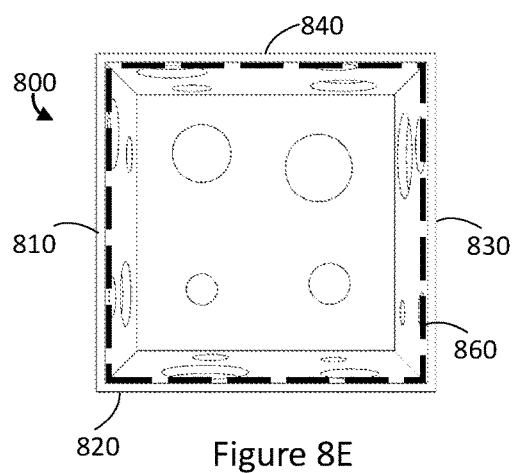

FIGS. 8A-8E illustrate an exemplary marker 800. FIGS. 8A and 8B are isometric views of the marker 800. FIG. 8C is a front view of marker 800. FIG. 8D is a side view of marker 800. FIG. 8E is a rear view of marker 800. In an example, marker 800 is similar to marker 400 discussed with reference to FIGS. 4A-4E and marker 700 discussed with reference to FIGS. 7A-7E. Unless context dictates otherwise, discussion of marker 400 and marker 700 is applicable to marker 800 and vice-versa. Marker 800 includes a mask unit 802 having faces 810, 820, 830, and 840, which are similar to faces 410, 420, and 430 in marker 400 or faces 710, 720, and 730 in marker 700. In an example, an optically detectable cartridge 890 is positioned in an interior volume of marker 800, through an aperture 860 adjacent each of faces 810, 820, 830, and 840, similar to cartridge 490 in marker 400 or cartridge 790 in marker 700. Detailed implementations of cartridge are discussed below with reference to FIGS. 16A-25C. Aperture 860 is shown accentuated by dashed lines in FIG. 8E. FIGS. 8A, 8C, and 8D show marker 800 with cartridge 890 positioned in the interior volume thereof.

One difference between marker 800 and marker 400 is that marker 800 is illustrated without an extension like extension 450 in marker 400 shown in FIGS. 4A-4E. In some implementations, marker 800 includes such an extension (or any other appropriate form of extension), but the extension is not shown in FIGS. 8A-8E to focus more on the features specific to marker 800.

Another difference between marker 800 and marker 400 is that marker 800 includes a front face 850, in addition to faces 810, 820, 830, and 840. In an example, front face 850 is similar to front face 740 in marker 700, and improves viewing angles and tracking effectiveness of the marker 800.

Yet another difference between marker 800 and markers 400 and 700 is that marker 800 includes four faces adjacent aperture 860 (e.g. that form or define the aperture), instead of three faces. That is, the four faces 810, 820, 830, and 840 define an interior volume of the mask unit 802, and free ends of faces 810, 820, 830, and 840 define a cartridge receiving aperture 860 to the interior volume. The inclusion of the fourth face reduces a relative outside angle between adjacent faces, which in turn reduces the steepness of angle at which a given face will be viewed. This concept is discussed with reference to FIGS. 9A-9F below.

Figure 9A:
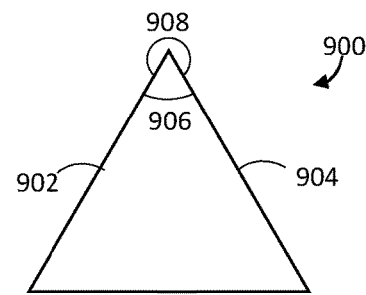
FIGS. 9A and 9B are conceptual views of a triangular profile of a marker.
Figure 9B:
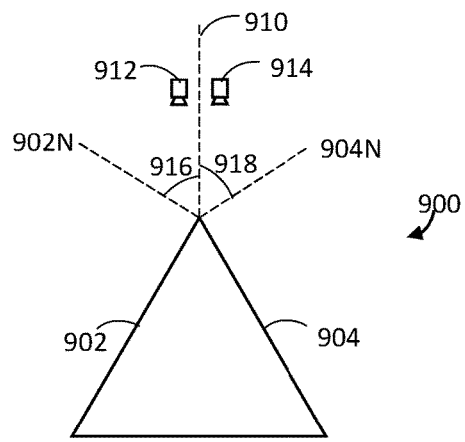

FIGS. 9A and 9B are conceptual views of a triangular profile 900, which correspond to a cross-section of marker 400 or marker 700 taken in the plane of the page in FIG. 4C or 7C. FIGS. 9A and 9B show two adjacent sides 902 and 904. An inside angle between faces 902 and 904 is shown in FIG. 9A as angle 906, and an outside angle between faces 902 and 904 is shown in FIG. 9A as angle 908. For an equilateral triangle, angle 906 is 60°, and angle 908 is 300°. The effect of outside angle between adjacent sides is illustrated in FIG. 9B. FIG. 9B illustrates a boundary 910, which delineates regions where a different face of a marker will be detected and tracked, in implementations where a single face of the marker is used for tracking. In the example of FIG. 9B, if an image sensor is positioned left of boundary 910 (e.g. in position 912), face 902 of the marker will be detected and tracked; if an image sensor is positioned right of boundary 910 (e.g. in position 914), face 904 will be detected and tracked. FIG. 9B illustrates an angular range 916, which ranges from boundary 910 to an axis 902N normal to face 902. FIG. 9B also illustrates an angular range 918, which ranges from boundary 910 to an axis 904N normal to face 904. That is, angular range 916 represents the steepness from normal 902N at which the image sensor can be positioned, where face 902 should still be detectable and trackable; angular range 918 represents the steepness from normal 904N at which the image sensor can be positioned, where face 904 should still be detectable and trackable. For an equilateral triangle, angular range 916 and angular range 918 are 60°.

Figure 9C:
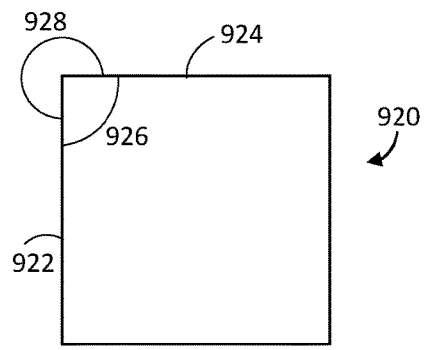
FIGS. 9C and 9D are conceptual views of a square profile of a marker.
Figure 9D:
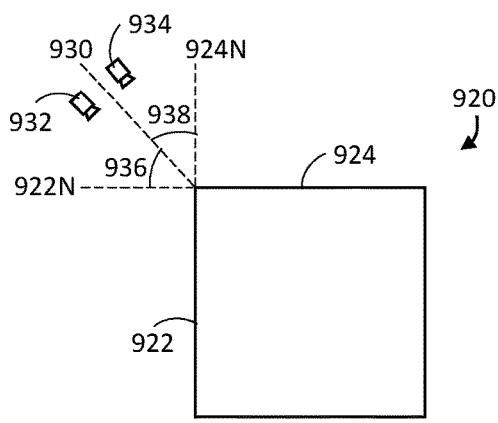

FIGS. 9C and 9D are conceptual views of a square profile 920, which correspond to a cross-section of marker 800 taken in the plane of the page in FIG. 8C. FIGS. 9C and 9D shows two adjacent sides 922 and 924. An inside angle between faces 922 and 924 is shown as angle 926, and an outside angle between faces 922 and 924 is shown as angle 928. For a square, angle 926 is 90°, and angle 928 is 270°. Comparing square profile 920 to triangular profile 900, it is evident that the outside angle between two adjacent faces is reduced by 30° through the addition of a fourth face. By having a reduced outside angle between faces, a tracking system will be able to track the marker without having to detect and analyze faces of the marker at as steep of angles. FIG. 9D illustrates a boundary 930, which delineates regions where a different face of a marker will be detected and tracked, in implementations where a single face of the marker is used for tracking (similar to boundary 910 discussed above). In the example of FIG. 9D, if an image sensor is positioned left of boundary 930 (e.g. in position 932), face 922 of the marker will be detected and tracked; if an image sensor is positioned right of boundary 930 (e.g. in position 934), face 924 will be detected and tracked. FIG. 9D illustrates an angular range 936, which ranges from boundary 930 to an axis 922N normal to face 922. FIG. 9D also illustrates an angular range 938, which ranges from boundary 930 to an axis 924N normal to face 924. That is, angular range 936 represents the steepness from normal 922N at which the image sensor can be positioned, where face 922 should still be detectable and trackable; angular range 938 represents the steepness from normal 924N at which the image sensor can be positioned, where face 924 should still be detectable and trackable. For a square, angular range 936 and angular range 938 are 45°. Angular ranges 936 and 938 are less than angular ranges 916 and 918 (by 15°, for the examples of a square and equilateral triangle). That is, for a given face of a marker to be detectable and trackable, the addition of a fourth face decreases the steepness of angle at which the face might be viewed. Thus, the optical detectability requirements of the cartridge at steep angles (such as effective retroreflective angles, as discussed with reference to FIGS. 6A and 6B), are reduced.

Figure 9E:
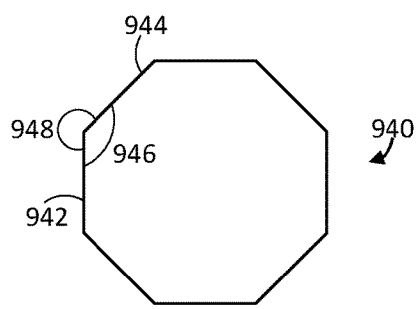
FIGS. 9E and 9F are conceptual views of an octagonal profile of a marker.
Figure 9F:
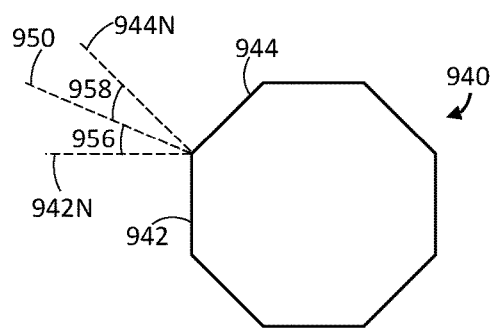

The inclusion of even more sides can further improve detectability of a marker. For example, FIGS. 9E and 9F are conceptual views of an octagonal profile 940, which corresponds to a cross-section of marker 1000 taken in the plane of the page in FIG. 10C discussed below. FIGS. 9E and 9F show two adjacent sides 942 and 944. An inside angle between faces 942 and 944 is shown as angle 946, and an outside angle between faces 942 and 944 is shown as angle 948. For an octagon, angle 946 is 135°, and angle 948 is 225°. For octagonal profile 940, it is evident that the outside angle between two adjacent faces is reduced by 75° compared to triangular profile 900, and is reduced by 50° compared to square profile 920. Similar to above, by having a reduced outside angle between faces, a tracking system will be able to track the marker without having to detect and analyze faces of the marker at as steep of angles. FIG. 9F illustrates a boundary 950, which delineates regions where a different face of a marker will be detected and tracked, in implementations where a single face of the marker is used for tracking (similar to boundaries 910 and 930 discussed above). In the example of FIG. 9F, if an image sensor is positioned below boundary 950, face 942 of the marker will be detected and tracked; if an image sensor is positioned above boundary 950, face 944 will be detected and tracked. FIG. 9F illustrates an angular range 956, which ranges from boundary 950 to an axis 942N normal to face 942. FIG. 9F also illustrates an angular range 958, which ranges from boundary 950 to an axis 944N normal to face 944. That is, angular range 956 represents the steepness from normal 942N at which the image sensor can be positioned, where face 942 should still be detectable and trackable; angular range 958 represents the steepness from normal 944N at which the image sensor can be positioned, where face 944 should still be detectable and trackable. For an octagon, angular range 956 and angular range 958 are 22.5°. Angular ranges 956 and 958 are less than angular ranges 916 and 918 (by 37.5°, for the example of an equilateral triangle), and angular ranges 956 and 958 are less than angular ranges 936 and 938 (by 22.5°, for the example of a square). That is, for a given face of a marker to be detectable and trackable, the addition of more faces decreases the steepness of angle at which the face might be viewed. Thus, the optical detectability requirements of the cartridge at steep angles (such as effective retroreflective angles, as discussed with reference to FIGS. 6A and 6B), are reduced even further by the inclusion of additional faces. In this regard, any of the markers discussed herein could have any appropriate amount of faces, to achieve desired viewability.

Figure 10A:
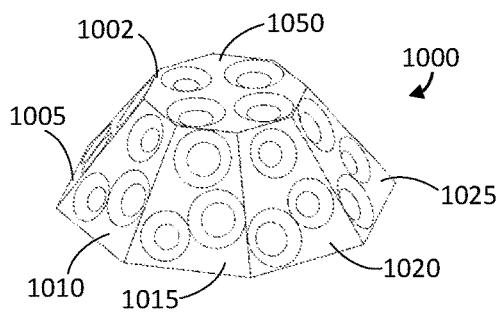
FIGS. 10A-10E illustrate an exemplary marker with eight side faces.
Figure 10B:
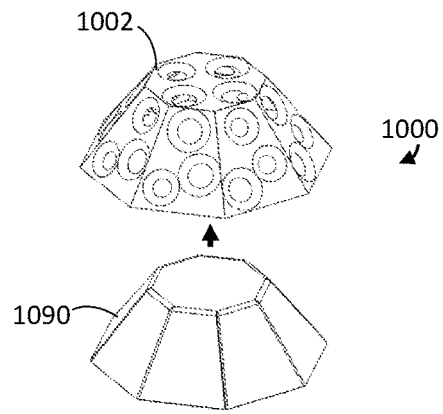
Figure 10C:
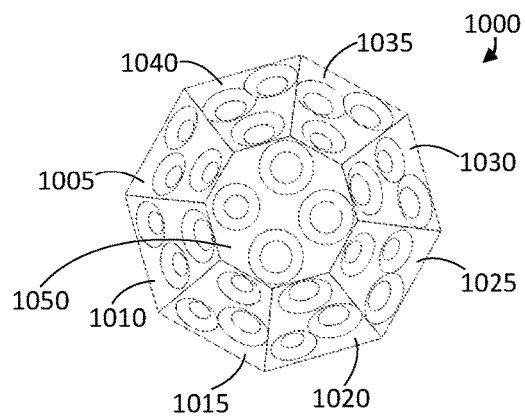
Figure 10D:
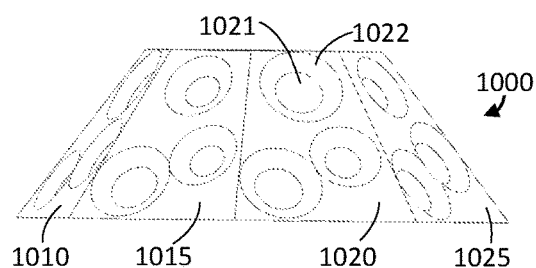
Figure 10E:
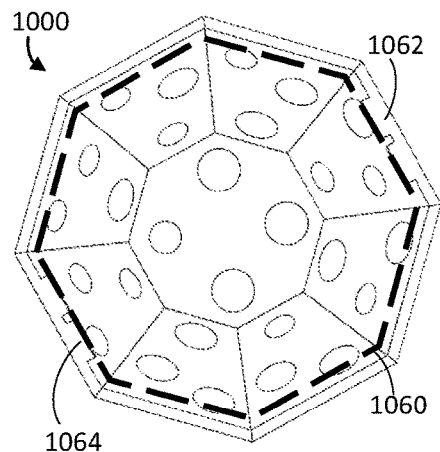

FIGS. 10A-10E illustrate an exemplary marker 1000, which includes eight side-faces, similar to the octagonal profile 900 in FIGS. 9E and 9F. FIGS. 10A and 10B are isometric views of the marker 1000. FIG. 10C is a front view of marker 1000. FIG. 10D is a side view of marker 1000. FIG. 10E is a rear view of marker 1000. In an example, marker 1000 is similar to marker 400 discussed with reference to FIGS. 4A-4E, marker 700 discussed with reference to FIGS. 7A-7E, and marker 800 discussed with reference to FIGS. 8A-8E. Unless context dictates otherwise, discussion of marker 400, marker 700, and marker 800 is applicable to marker 1000 and vice-versa.

Marker 1000 includes a mask unit 1002 having faces 1005, 1010, 1015, 1020, 1025, 1030, 1035, 1040, which are similar to faces 410, 420, and 430 in marker 400, faces 710, 720, and 730 in marker 700, or faces 810, 820, 830, and 840 in marker 800. An optically detectable cartridge 1090 is positioned in an interior volume of marker 1000, through an aperture 1060 defined by free ends of each of faces 1005, 1010, 1015, 1020, 1025, 1030, 1035, and 1040, similar to cartridge 490 in marker 400, cartridge 790 in marker 700, or cartridge 890 in marker 800. Detailed implementations of cartridge are discussed below with reference to FIGS. 16A-25C. Aperture 1060 is shown accentuated by dashed lines in FIG. 10E.

One difference between marker 1000 and marker 400 is that marker 1000 is illustrated without an extension like extension 450 in marker 400 shown in FIGS. 4A-4E. In some implementations, marker 1000 includes such an extension (or any other appropriate form of extension), but the extension is not shown in FIGS. 10A-10E to focus more on the features specific to marker 1000.

Another difference between marker 1000 and marker 400 is that marker 1000 includes a front face 1050, in addition to faces 1005, 1010, 1015, 1020, 1025, 1030, 1035, and 1040. Front face 1050 is similar to front face 740 in marker 700 or front face 850 in marker 800, and improves viewing angles and tracking effectiveness of the marker 1000.

Yet another difference between marker 1000 and markers 400 and 700 is that marker 1000 includes a clip 1062 and a clip 1064. Together, clips 1062 and 1064 secure cartridge 1090 in the interior volume of marker 1000, as is discussed in more detail with reference to FIG. 23B. More clips could be included in some implementations. Alternatively, no clips could be included, or other cartridge securing mechanisms could be included. In embodiments, markers 400, 700, or 800 also include similar clips or cartridge securing mechanisms.

Yet another difference between marker 1000 and markers 400 and 700 is that marker 1000 has chamfers around each opening in the faces. For example, FIG. 10D shows a chamfer 1022 around opening 1021 in face 1020. The inclusion of such chamfers can increase a viewable angular range of light from the opening, for the reasons discussed with reference to FIG. 6B. The inclusion of such chamfers is optional, and any of the markers discussed herein could have chamfers around openings therein.

Figure 11A:
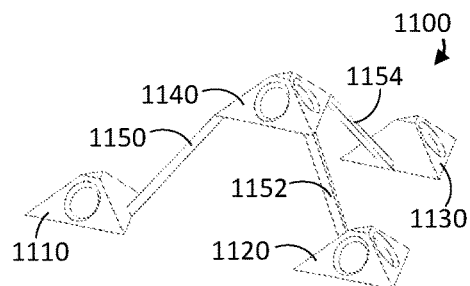
FIGS. 11A-11F illustrate an exemplary marker with four mask units.
Figure 11B:
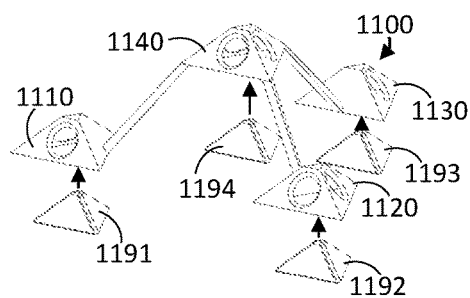
Figure 11C:
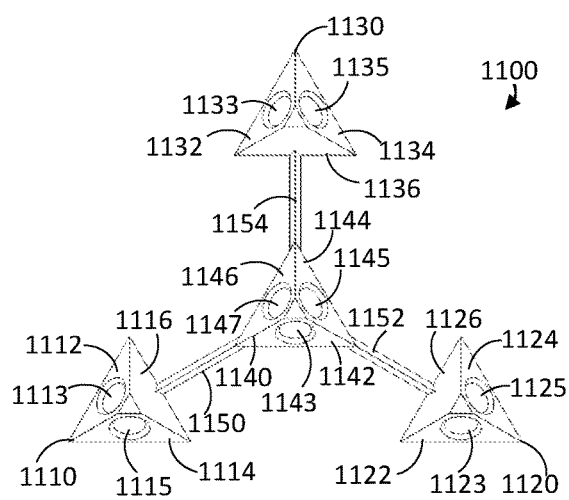
Figure 11D:
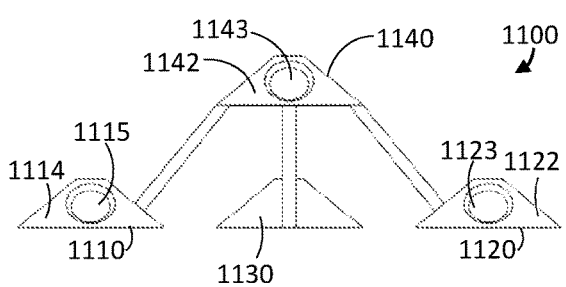
Figure 11E:
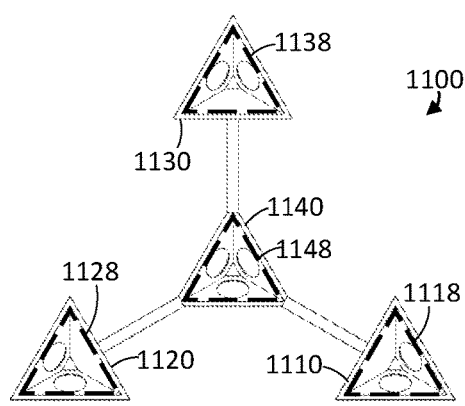

FIGS. 11A-11E illustrate another exemplary marker 1100. FIGS. 11A and 11B are isometric views of the marker 1100. FIG. 11C is a front view of marker 1100. FIG. 11D is a side view of marker 1100. FIG. 11E is a rear view of marker 1100.

FIGS. 11A-11E show marker 1100 as including four mask units 1110, 1120, 1130, and 1140, which operate similarly to the mask units described above. Each mask unit includes a plurality of faces, with some of the faces having at least one opening therein which is open to an interior volume of the respective mask unit. Mask unit 1110 includes face 1112 having opening 1113, face 1114 having opening 1115, and face 1116 having no opening, with each of openings 1113 and 1115 being open to an interior volume of mask unit 1110. Mask unit 1120 includes face 1122 having opening 1123, face 1124 having opening 1125, and face 1126 having no opening, with each of openings 1123 and 1125 being open to an interior volume of mask unit 1120. Mask unit 1130 includes face 1132 having opening 1133, face 1134 having opening 1135, and face 1136 having no opening, with each of openings 1133 and 1135 being open to an interior volume of mask unit 1130. Mask unit 1140 includes face 1142 having opening 1143, face 1144 having opening 1145, and face 1146 having opening 1147, with each of openings 1143, 1145, and 1147 being open to an interior volume of mask unit 1140. Although each of the openings are illustrated as being circular, other opening shapes are possible, as discussed later with reference to FIG. 15A.

Although marker 1100 includes four mask units, each mask unit having three faces, in other implementations additional mask units could be included, and/or additional faces could be included in each mask unit. Examples are discussed later with reference to FIGS. 13A-14B. Further, although the faces having openings in marker 1100 are only shown as including a single circular opening, it is possible for the faces to include a plurality of openings, and/or non-circular openings, such as in the examples discussed later with reference to FIGS. 15A-15I.

Free ends of the faces of each mask unit are adjacent to (define a) respective aperture which is open to an interior volume of the mask unit. The three faces 1112, 1114, and 1116 are adjacent an aperture 1118 which is open to an interior volume of mask unit 1110. The three faces 1122, 1124, and 1126 are adjacent an aperture 1128 which is open to an interior volume of mask unit 1120. The three faces 1132, 1134, and 1136 are adjacent an aperture 1138 which is open to an interior volume of mask unit 1130. The three faces 1142, 1144, and 1146 are adjacent an aperture 1148 which is open to an interior volume of mask unit 1140. Each of the apertures is shown accentuated by dashed lines in FIG. 11E.

FIGS. 11A, 11C, and 11D show marker 1100 as having a respective optically detectable cartridge positioned within the interior volume of each mask unit. FIG. 11B shows optically detectable cartridges 1191, 1192, 1193, and 1194 prior to positioning within the interior volume of respective mask units 1110, 1120, 1130, and 1140. Optically detectable cartridges 1191, 1192, 1193, and 1194 can be similar to optically detectable cartridges 490, 790, 890 and 1090 discussed above. Detailed implementations of cartridge are discussed below with reference to FIGS. 16A-25C. When an optically detectable cartridge is positioned within the interior volume of a mask unit, an optically detectable surface of the cartridge is exposed through each opening of the mask unit. The optically detectable cartridges can be inserted into the interior volume of the respective mask units through apertures 1118, 1128, 1138, and 1148 illustrated in FIG. 11E. Preferably, mask units 1110, 1120, 1130, and 1140 can have similar size and shape, so that one size of cartridge fits within the interior volume of each mask unit.

The mask units can be positioned such that at least one of the mask units is positioned in a first plane spatially separated from a second plane in which at least one other mask unit is positioned. In the example of marker 1100, mask units 1110, 1120, and 1130 can be positioned in a first plane, and mask unit 1140 can be positioned in a second plane parallel to but spatially separated from the first plane. This can be seen particularly well in FIG. 11D, where mask units 1110, 1120, and 1130 are positioned at the same height in the page, but mask unit 1140 is positioned above the other mask units.

The plurality of mask units can be connected together by any appropriate connecting structure. In the example of FIGS. 11A-11E, three connectors 1150, 1152, and 1154 connect the mask units to each other. In particular, connector 1150 couples face 1116 of mask unit 1110 to mask unit 1140; connector 1152 couples face 1126 of mask unit 1120 to mask unit 1140; connector 1154 couples face 1136 of mask unit 1130 to mask unit 1140. In this way, the mask units are coupled together so as to have a predictable geometry. Alternative or additional connecting structures are within the scope of the present invention; as an example, connectors could directly connect mask units 1110, 1120, and 1130 to each other. In some implementations, mask units 1110, 1120, 1130, and 1140 can be formed together with connectors 1150, 1152, and 1154 as a monolithic structure. In other implementations, mask units 1110, 1120, 1130, and 1140 can be formed separately, and can be coupled together as an assembly with connectors 1150, 1152, and 1154.

Figure 11F:
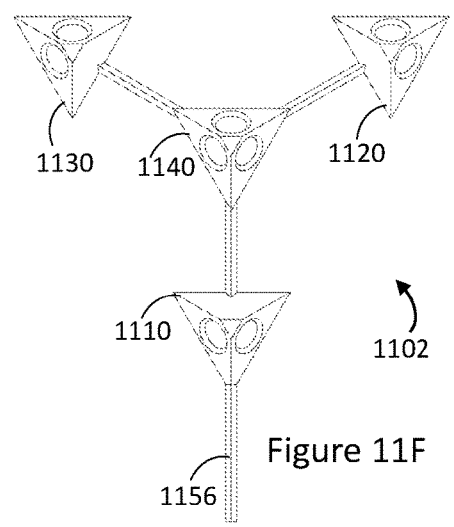

FIG. 11F is a front view of a marker 1102, which, in an example, is similar to marker 1100 described above and illustrated in FIGS. 11A-11E. One difference between marker 1102 and marker 1100 is that marker 1102 includes an extension 1156 coupled to the marker. In an example, extension 1156 is illustrated as being coupled to mask unit 1110. But, in an example, extension 1156 is coupled to any appropriate location of marker 1102, such as mask unit 1120, mask unit 1130, mask unit 1140, connector 1150, connector 1152, or connector 1154, for example. In an example, extension 1156 is integrally formed with marker 1102, such that marker 1102 is a monolithic cluster of mask units and an extension. Alternatively, in an example, extension 1156 is a separate component which is coupled to marker 1102, for example by fasteners such as clips, screws, bolts, pins, or adhesive, or by processes such as welding, melting, or soldering. In an example, such coupling is removable/replaceable, such as magnetic coupling. Any appropriate coupling between the extension 1156 and the marker 1102 could be used.

Extension 1156 can be similar to extension 450 described with reference to FIGS. 4A-4E, and can similarly be used to track elements which are distal from the marker 1102. Further, it is within the scope of the present invention for marker 1102 to not include extension 1156.

A plurality of faces of the plurality of mask units can together be detected and tracked as a single conceptual "face" of the marker 1100, akin to how individual faces in markers 400, 700, 800, and 1000 are detected and tracked as discussed above. In particular, faces from different mask units which face in a similar direction to each other can be detected and tracked together. This can be seen particularly in FIG. 11C: in the example of marker 1100, faces 1112, 1132, and 1146 can be detected and tracked together as a first conceptual "face"; faces 1114, 1122, and 1142 can be detected and tracked together as a second conceptual "face";

and faces 1124, 1134, and 1144 can be detected and tracked together as a third conceptual "face". FIG. 11D illustrates an exemplary side view of the second conceptual "face", where faces 1114, 1142, and 1122 can be detected and tracked together. In particular, optically detectable cartridges can be exposed to an image sensor through openings 1115, 1143 and 1123. A processing device can determine a pose of marker 1100 based on the size, shape, and relative positioning of openings 1115, 1143, and 1123.

By including at least three conceptual "faces" with openings as discussed above, the marker 1100 can be detected, localized, and tracked using image data from a single image sensor as long as a single conceptual "face" of the marker 1100 is visible to the image sensor. Consequently, marker 1100 is robust against self-occlusion, because even if some faces are occluded, enough other faces will be visible to perform reliable tracking. Thus marker 1100 is viewable from a greater range of viewing angles, similar to as discussed above regarding FIGS. 5A and 5B.

In the markers discussed above, the markers can be detected, localized, and tracked as long as a single face is visible (physical face in the case of markers 400, 700, 800, and 1000; conceptual face in the case of marker 1100). However, since each marker contains multiple such faces, it is desirable to be able to determine which face is being viewed, to accurately determine the overall pose of the marker (as opposed to a pose of the face).

Figure 12A:
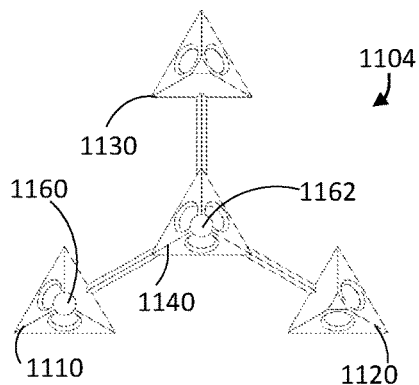
FIGS. 12A-12K illustrate an exemplary marker having four mask units.
Figure 12B:
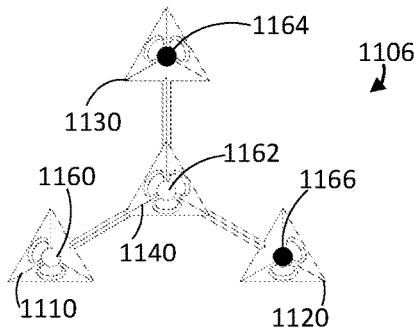

FIGS. 12A and 12B are front views of exemplary marker 1104 and marker 1106, respectively. Each of markers 1104 and 1106 is similar to marker 1100 discussed above. FIGS. 12A and 12B illustrate exemplary identification features which can be implemented on the markers discussed herein to assist in determining which conceptual face of a marker is being viewed. In particular, FIGS. 12A and 12B illustrate optically detectable identifiers 1160 and 1162 positioned on mask units 1110 and 1140, respectively. FIG. 12B illustrates optically non-detectable identifiers 1164 and 1166 positioned on mask units 1130 and 1120, respectively. Each of identifiers 1160, 1162, 1164, and 1166 is positioned adjacent to each face of the respective mask unit on which the identifier is positioned. FIGS. 12C-12K illustrate markers 1104 and 1106 when viewed by a tracking system.

Figure 12C:
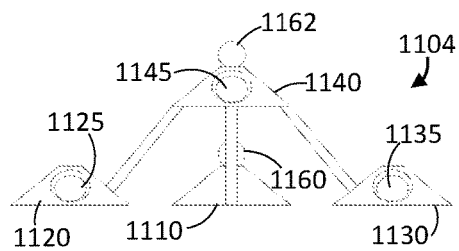
Figure 12D:
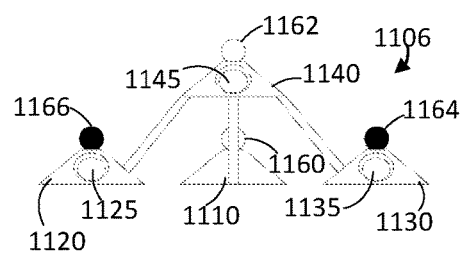
Figure 12E:
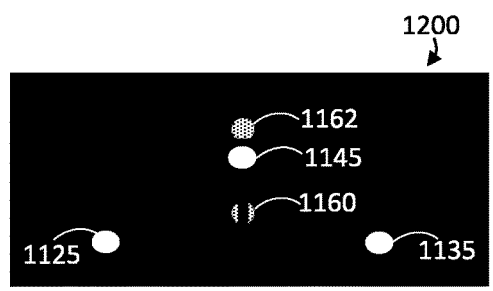

FIGS. 12C and 12D are side views of marker 1104 and marker 1106, respectively, both viewed from a first direction. FIG. 12E illustrates an exemplary image 1200 captured by an image sensor of a tracking system viewing either marker 1104 or marker 1106 from the first direction. In the example of FIG. 12E, cartridges of the marker are detectable with greater brightness than the mask units, such that much of the image is dark or black, with trackable features being bright and highly detectable. However, in alternative implementations, the mask units could be detected with greater brightness than the cartridges, such that the mask units appear bright, and surround dark or black regions which are detected and tracked. In the image 1200, openings 1125, 1135, and 1145 are clearly detectable. Based on the shape, size, and positioning of the openings as seen by the image sensor, the tracking system can determine a pose of the conceptual face being viewed. However, based on the openings alone, the tracking system may not be able to determine which three openings are being viewed (particularly if the openings are similar or identical in geometry to each other). In the image 1200, identifier 1162 is clearly detectable. Based on the relative positioning of the identifier 1162 to the detected openings and the absence of other fully detectable identifiers (i.e., an identifier pattern), the tracking system can determine that the conceptual face being viewed is the conceptual face which includes openings 1125, 1135, and 1145. Thus, the tracking system can determine a pose of a face based on detected openings, and can determine which face is being viewed based on the detected identifier or identifiers.

In image 1200 Identifier 1160 is partially detectable (because identifier 1160 is partially obscured by a connector of the marker structure); the tracking system could disregard this partially detectable identifier, or could also use the partially detectable identifier in the detection.

Figure 12F:
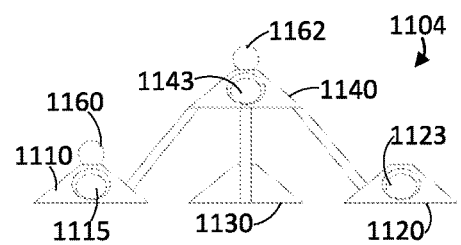
Figure 12G:
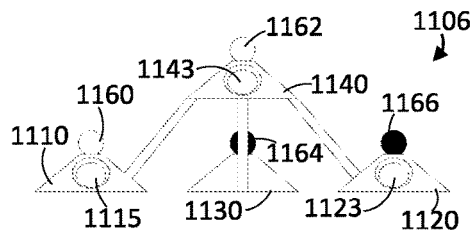
Figure 12H:
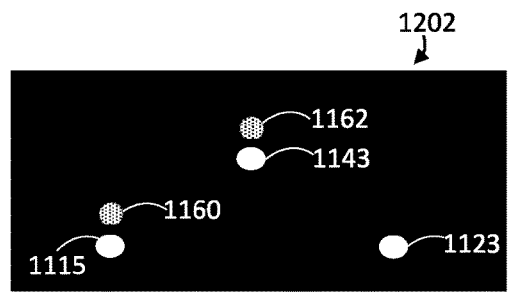

FIGS. 12F and 12G are side views of marker 1104 and marker 1106, respectively, both viewed from a second direction different from the first direction of FIGS. 12C and 12D. FIG. 12H illustrates an exemplary image 1202 captured by the image sensor. In the image 1202, openings 1115, 1123, and 1143 are clearly detectable, similarly to as discussed with reference to image 1200 above. Based on the shape, size, and positioning of the openings as seen by the image sensor, the tracking system can determine a pose of the conceptual face being viewed. In the image 1202, identifiers 1160 and 1162 are clearly detectable. Based on the relative positioning of the identifiers 1160 and 1162 to the detected openings and the absence of other fully detectable identifiers (i.e., an identifier pattern), the tracking system can determine that the conceptual face being viewed is the conceptual face which includes openings 1115, 1123, and 1143.

Figure 12I:
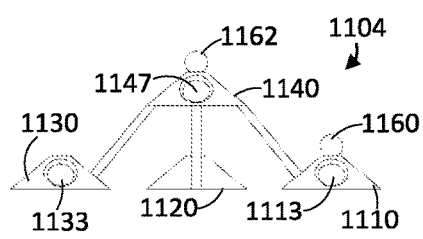
Figure 12J:
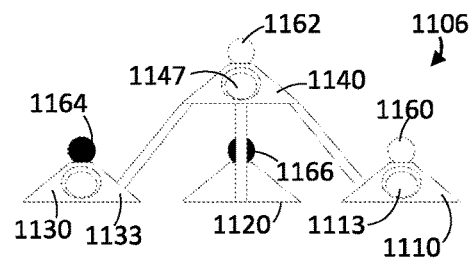
Figure 12K:
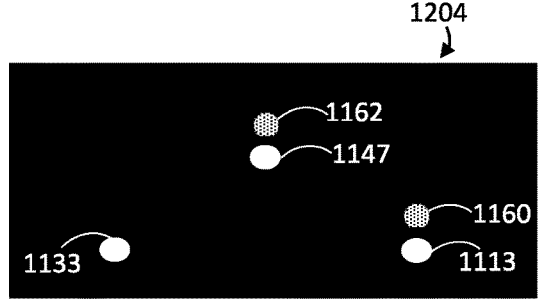

FIGS. 12I and 12J are side views of marker 1104 and mark 1106, respectively, both viewed from a third direction different from the first direction of FIGS. 12C and 12D and different from the second direction of FIGS. 12F and 12G. FIG. 12K illustrates an exemplary image 1204 captured by the image sensor. In the image 1204, openings 1113, 1133, and 1147 are clearly detectable, similarly to as discussed above regarding image 1200. Based on the shape, size, and positioning of the openings as seen by the image sensor, the tracking system can determine a pose of the conceptual face being viewed. In the image 1204, identifiers 1160 and 1162 are clearly detectable. Based on the relative positioning of the identifiers 1160 and 1162 to the detected openings and the absence of other fully detectable identifiers (i.e., an identifier pattern), the tracking system can determine that the conceptual face being viewed is the conceptual face which includes openings 1113, 1133, and 1147.

Based on detected openings alone, the tracking system may not be able to determine which openings are being viewed (particularly if the openings are similar or identical in geometry to each other). For example, comparing images 1200, 1202, and 1204, the pattern of detectable openings is practically the same, even though a different conceptual face of the marker is being viewed. However, a pattern of identifiers 1160 and 1162 is different for each conceptual face. Consequently, the tracking system can determine a pose of a face based on detected openings, and can determine which face is being viewed based on the detected identifier or identifiers.

In some implementations, the requirements for optical detectability of identifiers can be lower than for the cartridge surface detectable through the openings. This is shown in FIGS. 12E, 12H, and 12K, where the identifiers 1160 and 1162 are shown as being detected with lower brightness than the openings 1113, 1115, 1123, 1125, 1133, 1135, 1143, 1145, and 1147. The tracking system can first determine the pose of detected openings, and subsequently detect identifiers based on expected locations of the identifiers, based on the pose of the detected openings. Since the potential locations of identifiers can be relatively predictable based on the pose of the openings, the identifiers do not need to be as detectable to achieve unambiguous detectability. As an example, in systems which use a light source near an image sensor, in combination with retroreflective cartridges, optically detectable identifiers could be formed or coated with a reflective or light-colored material. Consequently, while the openings will be highly detectable thanks to the retroreflective cartridge material, the identifiers may be less detectable (because reflected light therefrom will be less directed and/or bright). However, this may still be sufficient to achieve sufficient detectability of the identifiers for the purpose of face detection. In alternative implementations where the mask unit appears bright to the tracking system, optically detectable identifiers could comprise materials which appear dark to the tracking system.

Optically detectable identifiers could be formed of or coated with plastic, paint, powder coating, or any other appropriate materials. Further, optically detectable identifiers could be formed of optically non-detectable material, and coated with optically detectable material. Many factors could be considered or adjusted when selecting or designing optically detectable surfaces, including material, texture (e.g. roughness/smoothness), color, sterilizability, or other appropriate factors.

Notably, image 1200 corresponds to a captured image of either marker 1104 or marker 1106, image 1202 corresponds to a captured image of either marker 1104 or marker 1106, and image 1204 corresponds to a captured image of either marker 1104 or marker 1106. This is because in the exemplary implementations the optically non-detectable identifiers 1164 and 1166 are designed to appear dark to the tracking system, and thus don't appear strongly in images 1200, 1202, and 1204. However, by including optically non-detectable identifiers as in marker 1106, background or stray light can be prevented from being misinterpreted by the tracking system as an optically detectable identifier. For example, for marker 1104 as viewed in image 1200, if a sufficient amount of background or stray light were to be captured by the image sensor above opening 1125, the tracking system may misinterpret the marker as being in the orientation captured in image 1202 instead. In contrast, if optically non-detectable identifiers 1164 and 1166 are included as in marker 1106, such background or stray light can be blocked or absorbed by the optically non-detectable identifiers. Thus, accuracy of tracking can be improved.

Optically non-detectable identifiers could be formed of or coated with anodized aluminum, plastic, rubber, paint, powder coating, or any other appropriate materials. Many factors could be considered or adjusted when selecting or designing optically non-detectable surfaces, including material, texture (e.g. roughness/smoothness), color, sterilizability, or other appropriate factors.

Identifiers, such as identifiers 1160, 1162, 1164, and 1166, can be integrally formed with a marker body, or could be separately formed and subsequently affixed to a marker body with adhesive, fasteners, welding, or any other appropriate coupling means. Further, identifiers can be made of a sterilizable or autoclavable material, such that the marker body and identifiers could be sterilized/autoclaved together, thereby reducing the amount of assembly and disassembly required for a marker between uses.

In addition to being useful to identify a conceptual "face" of a marker, a pattern of identifiers such as identifiers 1160, 1162, 1164, and 1166 can also be used to identify or distinguish between multiple different markers. For example, compared to markers 1104 and 1106, a similar marker could be designed, but with identifier 1162 being a non-optically detectable identifier (or not present at all). In this way, when viewed by an image sensor, this other marker could be distinguished from marker 1104 or 1106 based on a lack of detectable identifier above openings 1145, 1143, and 1147. In such an example, identifier 1162 can be a "marker identifier", because marker 1162 is positioned in a location which is viewed by an image sensor over the entire angular range in which the marker can be tracked, and thus marker 1162 alone can distinguish one marker from another. Identifiers 1160, 1164, and 1166 can be "face identifiers" in the sense that these identifiers can uniquely identify the conceptual face being viewed.

Figure 13A:
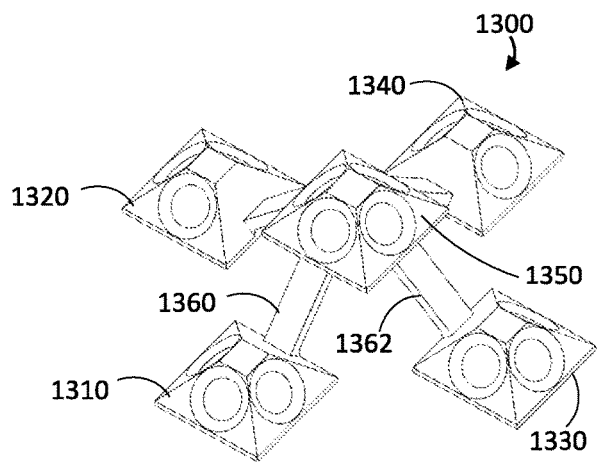
FIGS. 13A-13E illustrate an exemplary marker with five mask units.
Figure 13B:
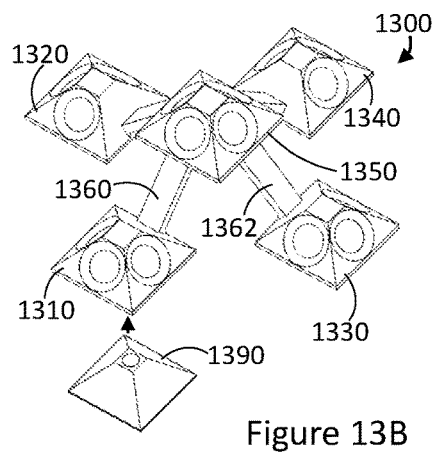
Figure 13C:
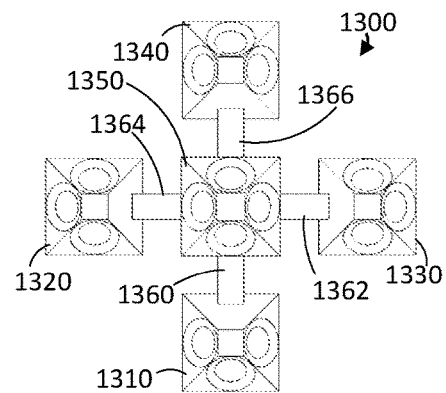
Figure 13D:
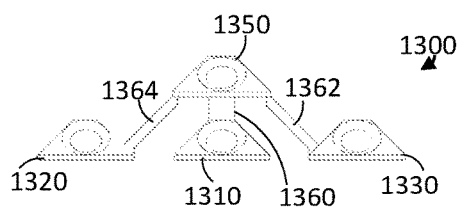
Figure 13E:
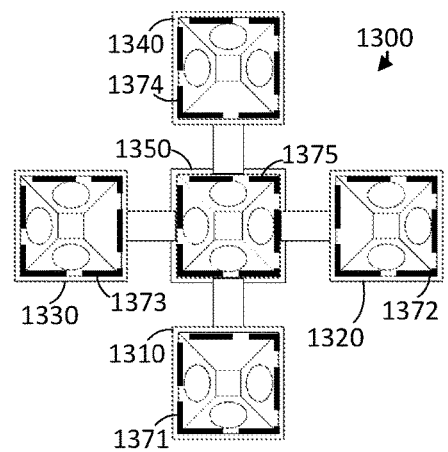

FIGS. 13A-13E illustrate another exemplary marker 1300. FIGS. 13A and 13B are isometric views of the marker 1300. FIG. 13C is a front view of marker 1300. FIG. 13D is a side view of marker 1300. FIG. 13E is a rear view of marker 1300.

Marker 1300 can be similar to marker 1100 in FIGS. 11A-11E, and description of marker 1100 can be applicable to marker 1300. One difference between marker 1300 and marker 1100 is that marker 1300 includes five mask units 1310, 1320, 1330, 1340, and 1350, as opposed to four mask units in marker 1100. The inclusion of the additional mask unit results in marker 1300 having an additional conceptual "face" which can be detected and tracked. FIG. 13D shows one exemplary such conceptual "face". When viewed at different angles, marker 1300 can have four such conceptual "faces". By having more conceptual "faces" which can be detected and tracked, an external angle between conceptual "faces" can be reduced, which in turn improves range of viewing angles at which marker 1300 can be detected and tracked, as discussed above regarding FIGS. 9A-9F.

Each mask unit includes a plurality of faces, with some of the faces of each mask unit having at least one opening therein which is open to an interior volume of the respective mask unit. Although marker 1300 includes five mask units, each mask unit having four faces, in other implementations additional mask units could be included, and/or additional faces could be included in each mask unit. Further, although the faces having openings in marker 1100 are only shown as including a single circular opening, it is possible for the faces to include a plurality of openings, and/or non-circular openings, such as in the examples discussed later with reference to FIGS. 15A-15I.

Free ends of the faces of each mask unit define a respective aperture which is open to an interior volume of the mask unit. In particular, an aperture 1371 is open to an interior volume of mask unit 1310; an aperture 1372 is open to an interior volume of mask unit 1320; an aperture 1373 is open to an interior volume of mask unit 1330; an aperture 1374 is open to an interior volume of mask unit 1340; and an aperture 1375 is open to an interior volume of mask unit 1350. Each of the apertures is shown accentuated by dashed lines in FIG. 13E.

FIGS. 13A, 13C, and 13D show marker 1300 as having a respective optically detectable cartridge positioned within the interior volume of each mask unit. FIG. 13B shows optically detectable cartridge 1390 prior to positioning within the interior volume of respective mask unit 1310. Similar optically detectable cartridges can be positioned in each of mask units 1320, 1330, 1340, and 1350. Preferably, mask units 1310, 1320, 1330, 1340, and 1350 can have similar size and shape, so that one size of cartridge fits within the interior volume of each mask unit. The optically detectable cartridges can be similar to optically detectable cartridges 490, 790, 890, 1090, and 1191-1194 discussed above. Detailed implementations of cartridge are discussed below with reference to FIGS. 16A-25C. When an optically detectable cartridge is positioned within the interior volume of a mask unit, an optically detectable surface of the cartridge is exposed through each opening of the mask unit. The optically detectable cartridges can be inserted into the interior volume of the respective mask units through apertures 1371, 1372, 1373, 1374, and 1375 illustrated in FIG. 13E.

The mask units can be positioned such that at least one of the mask units is positioned in a first plane spatially separated from a second plane in which at least one other mask unit is positioned. In the example of marker 1300, mask units 1310, 1320, 1330, and 1340 can be positioned in a first plane, and mask unit 1350 can be positioned in a second plane parallel to but spatially separated from the first plane. This can be seen particularly well in FIG. 13D, where mask units 1310, 1320, and 1330 (as well as mask unit 1340, not visible in FIG. 13D) are positioned at the same height in the page, but mask unit 1350 is positioned above the other mask units.

The plurality of mask units can be connected together by any appropriate connecting structure. In the example of FIGS. 13A-13E, four connectors 1360, 1362, 1364, and 1366 connect the mask units to each other, similar to in marker 1100. In this way, the mask units are coupled together so as to have a predictable geometry. Alternative or additional connecting structures are within the scope of the present invention; as an example, connectors could directly connect mask units 1310, 1320, 1330, and 1340 to each other as discussed below with reference to FIGS. 14A and 14B.

Although not illustrated, marker 1300 could include or be coupled to an extension similar to extension 450 or extension 1156 discussed above, to track elements which are distal from the marker 1300.

Figure 14A:
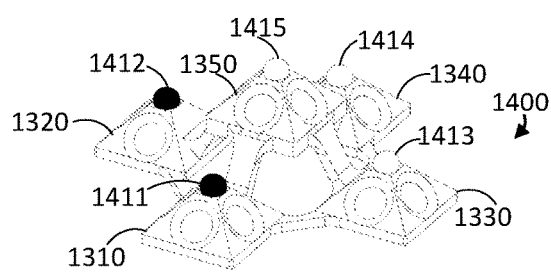
FIGS. 14A and 14B are an isometric view and a front view, respectively, of a marker having five mask units, with optically detectable identifiers and optically non-detectable identifiers positioned thereon.
Figure 14B:
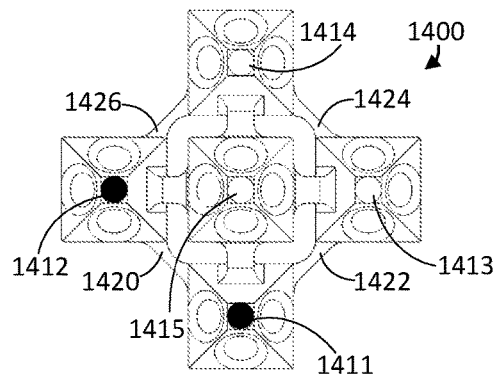

FIGS. 14A and 14B illustrate an exemplary marker 1400, which can be similar to marker 1300. FIG. 14A is an isometric view of marker 1400. FIG. 14B is a front view of marker 1400. Description of marker 1300 can be applicable to marker 1400.

One difference between marker 1400 and marker 1300 is that marker 1400 is shown as including face/marker identifiers. In particular, marker 1400 is shown as including optically detectable identifiers 1413, 1414, and 1415 positioned on mask units 1330, 1340, and 1350, respectively, which can be similar to optically detectable markers 1160 and 1162 discussed with reference to FIGS. 12A-12K. Further, marker 1400 is shown as including optically non-detectable identifiers 1411 and 1412 positioned on mask units 1310 and 1320, respectively, which can be similar to optically non-detectable markers 1164 and 1166 discussed with reference to FIGS. 12A-12K. Each of identifiers 1411, 1412, 1413, 1414, and 1415 can be positioned adjacent to each face of the respective mask unit on which the identifier is positioned. As discussed above regarding FIGS. 12A-12K, a tracking system can detect the optically detectable identifiers, and determine which face (or conceptual "face") of a marker is being viewed. Also as discussed above regarding FIGS. 12A-12K, different identifier patterns can be used to distinguish between different markers. Optically detectable identifiers 1413, 1414, and 1415 can be used without optically non-detectable identifiers, but optically non-detectable identifiers 1411 and 1412 can improve face identification accuracy, as discussed above.

Another difference between marker 1400 and marker 1300 is that marker 1400 is shown as including connectors 1420, 1422, 1424, and 1426. In particular, connector 1420 connects mask units 1310 and 1320; connector 1422 connects mask units 1310 and 1330; connector 1424 connects mask units 1330 and 1340; and connector 1426 connects mask units 1320 and 1340. Connectors 1420, 1422, 1424, and 1426 can be in addition to connectors which connect mask unit 1350 to other mask units (similar to connectors 1360, 1362, 1364, and 1366 discussed above), as shown in FIGS. 14A and 14B. Alternatively, connectors 1420, 1422, 1424, and 1426 can be used instead of some of the connectors between mask unit 1350 and other mask units.

Figure 15A:
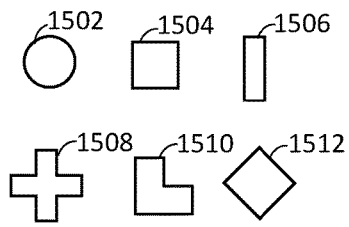
FIG. 15A illustrates several exemplary opening shapes.
Figure 15A:
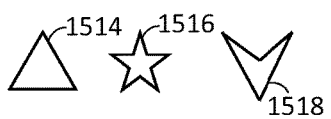

The markers discussed herein generally show openings in mask units as being circular in shape. However, many different opening shapes are possible, and provide different advantages. Further, any given marker can include multiple openings having different opening shapes. FIG. 15A illustrates several exemplary opening shapes, including circle 1502, square 1504, elongate rectangle 1506, cross 1508, corner 1510, diamond 1512, triangle 1514, star 1516, and arrow 1518. However, these opening shapes are merely exemplary, and other opening shapes are within the scope of the disclosure.

Compared to a circular opening 1502, openings which are not radially uniform can be useful to enable at least partial determination of orientation of the opening (in the plane of the page in FIG. 15A). For example, corner 1510 and arrow 1518 are rotationally unique, meaning that in the plane of the page, corner 1510 and arrow 1518 will have one shape for each different angle of rotation. This can be compared to other openings like square 1504, which will only specify a unique rotation within 90 degree angular ranges of rotation (i.e., square 1504 will have an identical appearance at four different rotational angles). However, many of the openings in FIG. 15A could be able to uniquely specify rotation by forming the opening with some amount of skew or elongation, to make the opening rotationally unique. For example, star 1516 could be elongated vertically in the plane of the page, such that star 1516 is rotationally unique. By using opening shapes which have more detectable features (e.g. more corners, extensions, etc.), detectability and trackability of individual openings can be improved. In some implementations, a single opening could be positioned on a face of a mask unit, and trackability of this single opening can be improved by shaping the opening to have interesting, detectable features.

Additionally, similar to as discussed above with reference to FIGS. 12A-12K and 14A-14B, it can be desirable for each face of a mask unit to be uniquely identifiable relative to other faces of the mask unit. Such unique identifiability can be achieved with unique opening patterns and/or unique opening shapes, as discussed below with reference to FIGS. 15B-15I.

Figure 15B:
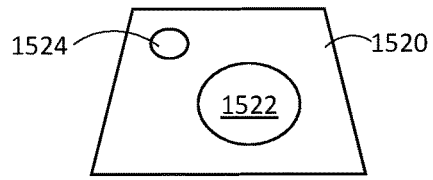
FIGS. 15B, 15C, 15D, 15E, 15F, 15G, 15H, and 15I are side views which illustrate exemplary faces and opening patterns.
Figure 15C:
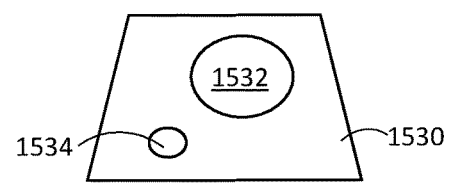

FIGS. 15B and 15C are side views of two different faces of a mask unit. FIG. 15B shows side 1520, and FIG. 15C shows side 1530. Side 1520 includes openings 1522 and 1524, with opening 1522 being larger than opening 1524, and positioned lower and to the right of opening 1524 (in the orientation shown in FIG. 15B). Side 1530 includes openings 1532 and 1534, with opening 1532 being larger than opening 1534, and positioned above and to the right of opening 1534 (in the orientation shown in FIG. 15C). The relative scale, positioning, and spacing between openings 1522 and 1524, and between openings 1532 and 1534, can make the different openings detectable relative to each other as a pattern for each face. Such a pattern can uniquely identify the face, such that a tracking system can determine what face of the mask unit is being viewed based on the pattern of viewed openings. Although FIGS. 15B and 15C illustrate an example where two openings are included per face, any appropriate number of openings could be included per face, such as three, four, five, six, seven, eight, nine, ten, or even more openings. Using more openings per face can make each face more uniquely identifiable. Further, although FIGS. 15B and 15C only illustrate two faces, additional faces could be included with unique patterns.

Figure 15D:
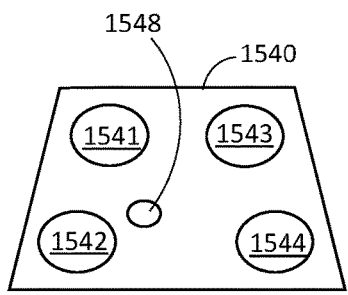
Figure 15E:
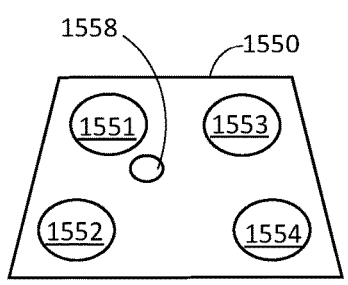
Figure 15F:
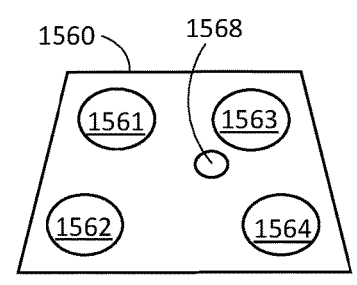
Figure 15G:
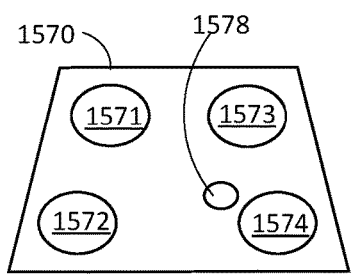

FIGS. 15D-15G are side views of different faces of a mask unit, which illustrate concepts of using a specific identification opening or openings. FIG. 15D illustrates a face 1540 having openings 1541, 1542, 1543, 1544, and 1548; FIG. 15E illustrates a face 1550 having openings 1551, 1552, 1553, 1554, and 1558; FIG. 15F illustrates a face 1560 having openings 1561, 1562, 1563, 1564, and 1568; FIG. 15G illustrates a face 1570 having openings 1571, 1572, 1573, 1574, and 1578. In FIG. 15D, openings 1541, 1542, 1543, and 1544 can be arranged in a first pattern. In FIG. 15E, openings 1551, 1552, 1553, and 1554 can also be arranged in the first pattern. In FIG. 15F, openings 1561, 1562, 1563, and 1564 can also be arranged in the first pattern. In FIG. 15G, openings 1571, 1572, 1573, and 1574 can also be arranged in the first pattern. By arranging a subset of openings in each face according to the same pattern (i.e., same relative size, positioning, and spacing of openings), a tracking system can perform similar detection and localization algorithms to detect a pose of any given face being viewed, and thus computational burden can be reduced compared to having to run individual pose determination algorithms for each face. In FIGS. 15D-15G, openings 1548, 1558, 1568, and 1578 can be positioned and/or shaped differently in each face, such that a tracking system can identify each face by analyzing the position and shape of the identification opening 1548, 1558, 1568, or 1578. That is, in the example of FIGS. 15D-15G, a tracking system can run an algorithm for detecting pose of a face being viewed, and another algorithm for determining which face is being viewed. Optionally, the pose detection algorithm can be run first, which can reduce computational burden of the face identification algorithm. In particular, once a pose of the face being viewed is determined, identification openings are expected to appear in certain locations, so the face detection algorithm can just detect whether an identification opening is present in the expected regions. In some implementations, although only the identification opening of each face is positioned differently in FIGS. 15D-15G, all of the openings of a given face together define a unique pattern for the face, which could be detected as a whole by a tracking system. Although FIGS. 15C-15G only illustrate four faces, additional faces could be included with unique patterns.

Figure 15H:
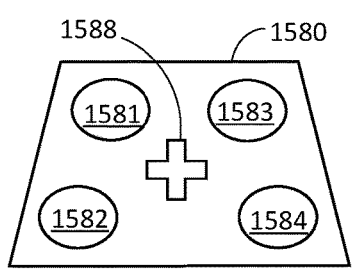
Figure 15I:
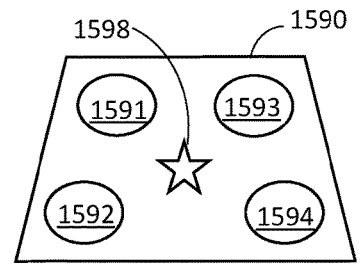

FIGS. 15H and 15I are side views of different faces of a mask unit, which illustrate concepts of using a uniquely shaped identification opening or openings. FIG. 15H shows a face 1580 having openings 1581, 1582, 1583, 1584, and 1588. FIG. 15I shows a face 1590 having openings 1591, 1592, 1593, 1594, and 1598. Similarly to as discussed with reference to FIGS. 15D-15G, openings 1581, 1582, 1583, and 1584 can be arranged in a pattern, and openings 1591, 1592, 1593, and 1594 can be arranged in the same pattern, for detection by a pose detection algorithm. However, opening 1588 and opening 1598 can have unique shapes, for detection by a face identification algorithm. In the example of FIGS. 15H and 15I, face 1580 can be identified by cross-shaped opening 1588, whereas face 1590 can be identified by star-shaped opening 1598. Other shapes of openings are possible, including the shapes illustrated in FIG. 15A, as non-limiting examples. Although FIGS. 15H and 15I only illustrate two faces, additional faces could be included with unique patterns.

FIGS. 15D-15I illustrate a single identification opening being included in each face. However, it is possible to include any number of identification openings in a given face. By including additional identification openings, more unique combinations can be achieved, to uniquely identify more faces. Further, although FIGS. 15D-15I illustrate identification openings as being positioned between the other openings of a face, it is possible for identification openings to be positioned elsewhere, such as at or toward the periphery of a face. However, positioning identification openings in a middle region between other openings of the face can increase the probability that the identification opening is associated with the correct face (as opposed to being associated with an adjacent face).

In some implementations, the optically detectable cartridges described herein is formed from folded planar sheets of material. In this way, many cartridges can be stored efficiently in a planar configuration, and later folded for insertion in a mask unit when needed. FIGS. 16A-16B, 17A-17B, and 18A-18B illustrate exemplary foldable cartridges in this regard.

Figure 16A:
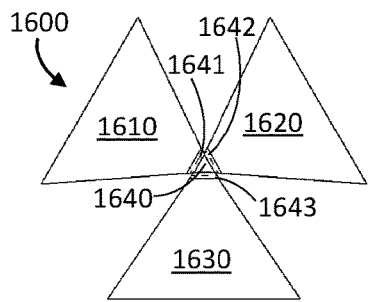
FIGS. 16A-16B, 17A-17B, and 18A-18B are front views of exemplary foldable cartridges.
Figure 16B:
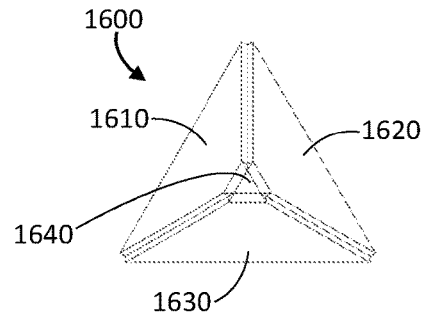

FIG. 16A is a front view of an optically detectable cartridge 1600 in an unfolded state. FIG. 16B is a front view of optically detectable cartridge 1600 in a folded state. Cartridge 1600 has three spoke regions 1610, 1620, and 1630, which each extend from a central region 1640. In an embodiment, each spoke region is similar in size and shape to a side face of a mask unit into which the cartridge is to be inserted. The cartridge 1600 is foldable at each boundary between the spoke regions and the central region 1640. In particular, FIG. 16A shows boundary 1641 between spoke region 1610 and central region 1640; boundary 1642 between spoke region 1620 and central region 1640; and boundary 1643 between spoke region 1630 and central region 1640. Cartridge 1600 is foldable at each of boundaries 1641, 1642, 1643 to transform cartridge 1600 into the folded form shown in FIG. 16B. To facilitate folding, in an example, each of boundaries 1641, 1642, and 1643 is weakened along a fold line (such as by perforations, a score line, or a line where the material of cartridge 1600 is thinner). By virtue of including three spoke regions, cartridge 1600 is suitable for use with mask units having three side faces, such as in marker 400, in marker 700 (if central region 1640 were larger so as to fit under all of the openings in front face 740), or in marker 1100. Cartridge 1600 is sized and dimensioned such that, when folded, cartridge 1600 fits into the interior volume of a mask unit through an aperture in the mask unit, and is exposed through any openings in faces of the mask unit.

Adjacent spoke regions in cartridge 1600 are shown as being separated by wedge-shaped gaps. In particular, spoke region 1610 is separated from spoke region 1620 by a first wedge-shaped gap; spoke region 1620 is separated from spoke region 1630 by a second wedge-shaped gap; and spoke region 1630 is separated from spoke region 1610 by a third wedge-shaped gap. In alternative implementations, spoke regions are separated from each other by collapsible regions, such as bifold regions discussed later with reference to FIGS. 21A-21B and 22.

Figure 17A:
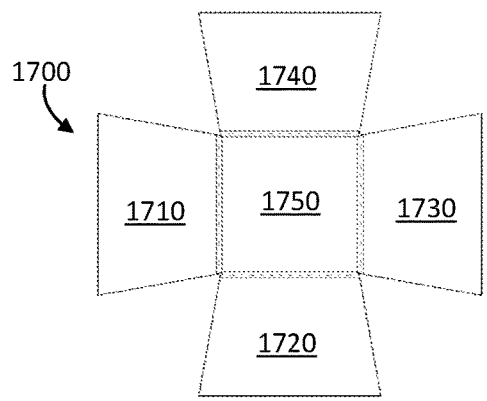
Figure 17B:
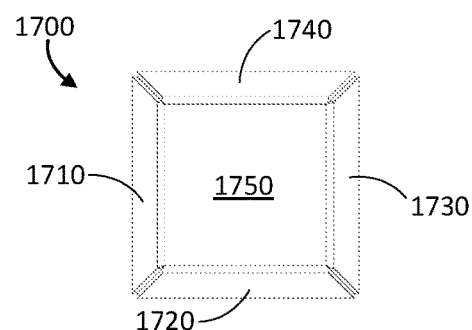

FIG. 17A is a front view of an optically detectable cartridge 1700 in an unfolded state. FIG. 17B is a front view of optically detectable cartridge 1700 in a folded state. Cartridge 1700 is similar to cartridge 1600 discussed above, such that description of cartridge 1600 applies to cartridge 1700.

One difference between cartridge 1700 and cartridge 1600 is that cartridge 1700 includes four spoke regions 1710, 1720, 1730, and 1740 which extend from central region 1750 (as opposed to three spoke regions). Another difference is that central region 1750 is shown as being larger than central region 1640 (though this is optional).

Similar to cartridge 1600, the spoke regions 1710, 1720, 1730, and 1740 in cartridge 1700 can similarly be separated by gaps or collapsible regions, and boundaries between the spoke regions and central region 1750 can be weakened along a fold line. By virtue of including four spoke regions, cartridge 1700 when folded as in FIG. 17B is suitable for use with mask units having four side faces, such as in marker 800, or in marker 1300 (although central region 1750 may need to be reduced in size for cartridge 1700 to match the shape of the mask units in marker 1300).

Figure 18A:
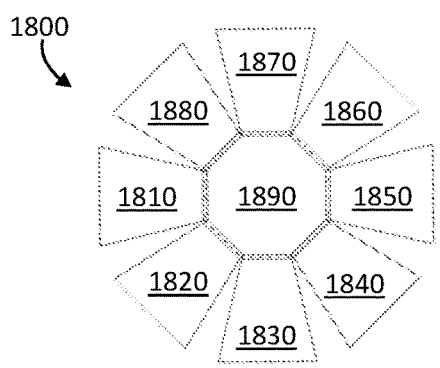
Figure 18B:
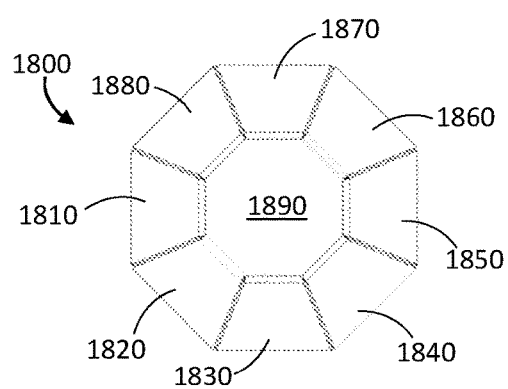

FIG. 18A is a front view of an optically detectable cartridge 1800 in an unfolded state. FIG. 18B is a front view of optically detectable cartridge 1800 in a folded state. Cartridge 1800 is similar to cartridges 1600 and 1700 discussed above, such that descriptions of cartridge 1600 and cartridge 1700 applies to cartridge 1800.

One difference between cartridge 1800 and cartridges 1600 and 1700 is that cartridge 1800 includes eight spoke regions 1810, 1820, 1830, 1840, 1850, 1860, 1870, and 1880 which extend from central region 1890 (as opposed to three or four spoke regions).

Similar to cartridges 1600 and 1700, the spoke regions 1810, 1820, 1830, 1840, 1850, 1860, 1870, and 1880 in cartridge 1800 can similarly be separated by gaps or collapsible regions, and boundaries between the spoke regions and central region 1890 can be weakened along a fold line. By virtue of including eight spoke regions, cartridge 1800 when folded as in FIG. 18B is suitable for use with mask units having eight side faces, such as in marker 1000.

Optically detectable cartridges can have any appropriate number of spoke regions, to match a number of side faces in a mask unit in which the cartridge is to be used.

Figure 19A:
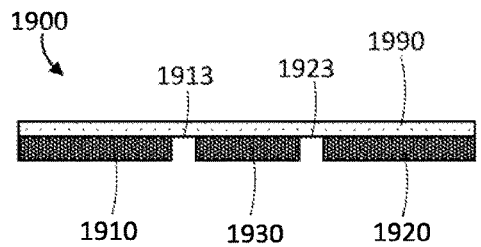
FIGS. 19A-19B are side cross-sectional views of an exemplary foldable cartridge.
Figure 19B:
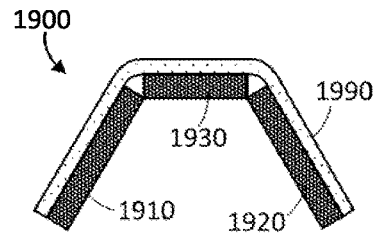

FIGS. 19A and 19B are side cross-sectional views of an exemplary cartridge 1900, which illustrate how fold lines can be defined by regions of the cartridge being thinner than other regions. Cartridge 1900 includes a flexible optically detectable material 1990, with sections of sturdy or rigid backing material 1910, 1920, and 1930 affixed thereto. Such backing material is, for example, affixed to the optically detectable material with adhesive, chemical treatment, welding, or any appropriate affixation means. Backing sections 1910 and 1920 define spoke regions extending from a central region defined by backing material 1930. Although only two spoke regions are shown in FIGS. 19A and 19B, in respective embodiments, cartridge 1900 has any appropriate number of spoke regions as discussed above regarding FIGS. 16A, 16B, 17A, 17B, 18A, and 18B. Backing sections 1910 and 1930 are separated by a gap 1913, and backing sections 1920 and 1930 are separated by a gap 1923, as shown in FIG. 19A. Gaps 1913 and 1923 define "weakened" regions along which cartridge 1900 is foldable into a folded configuration as shown in FIG. 19B.

Figure 20:
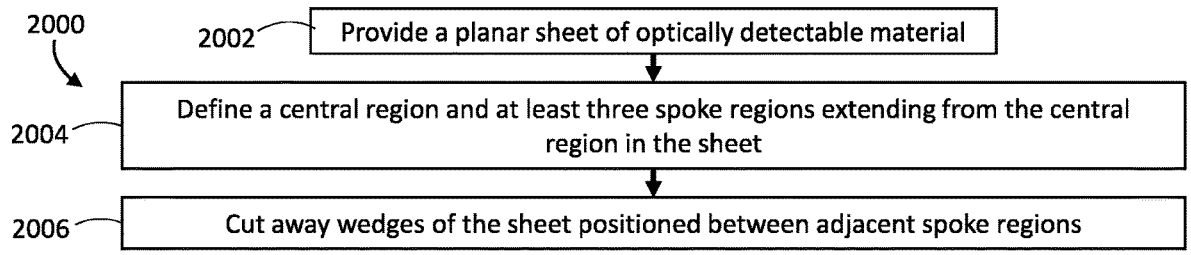
FIG. 20 is a flowchart diagram which illustrates an exemplary method for manufacturing optically detectable cartridges.

FIG. 20 is a flowchart diagram which illustrates an exemplary method 2000 for manufacturing optically detectable cartridges, such as cartridges 1600, 1700, 1800, and 1900 discussed above. Such optically detectable cartridges can be used with the mask units and markers discussed herein. Method 2000 includes acts 2002, 2004, and 2006, though additional acts could be added as appropriate.

In act 2002, a planar sheet of optically detectable material is provided. Optical detectability is only required on one surface of the sheet, though opposing surfaces of the sheet could be optically detectable if desired. When the optically detectable material is to appear bright to a tracking system, the optically detectable material includes, as examples, a reflective material, a light colored material, a retroreflective material, a diffuse material, or any other appropriate material. When the optically detectable material is to appear dark to a tracking system, the optically detectable material includes, as examples, a non-reflective material, an absorptive material, a dark colored material, or any other appropriate material.

In act 2004, a central region and at least three spoke regions extending from the central region are defined in the sheet. Any appropriate number of spoke regions could be defined, including four or eight spoke regions, as non-limiting examples discussed above with reference to FIGS. 17 and 18. The spoke regions are defined to have a size and shape approximating the interior size and shape of a side face of a mask unit into which the cartridge is intended to be inserted.

In act 2006, wedges of the sheet between adjacent spoke regions are cut away. This enables the spoke regions to be folded relative to the central region to form a three-dimensional cartridge for insertion into an interior volume of a three-dimensional mask unit.

Optionally, method 2000 may further include weakening each boundary between each of the spoke regions and the central region, to form a fold line at each boundary. In respective embodiments, this entails perforating or scoring said boundaries, or forming the sheet with thinner regions which correspond to said boundaries. The formation of such fold lines facilitates easy and consistent folding of the sheet in desired ways.

Figure 21A:
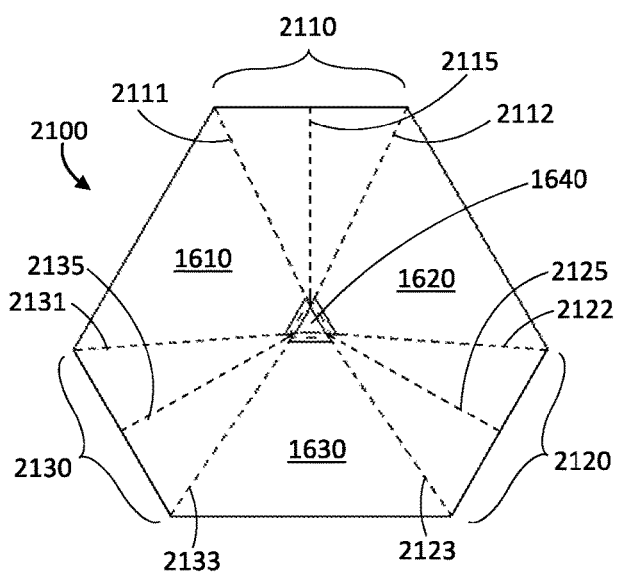
FIG. 21A is a front view of an exemplary foldable cartridge having collapsible regions.
Figure 21B:
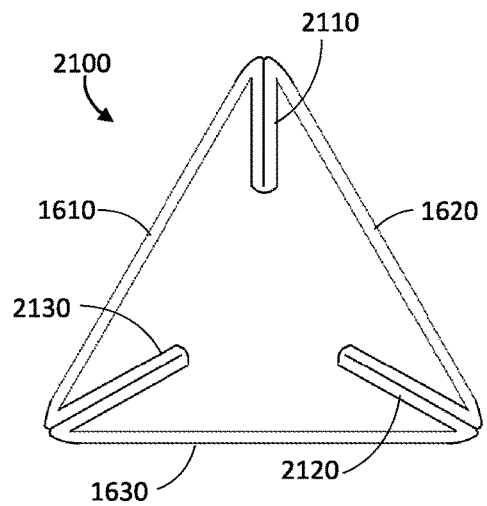
FIG. 21B is a rear view of the cartridge of FIG. 21A, in a folded configuration.

FIG. 21A is a front view of an optically detectable cartridge 2100 in an unfolded state; FIG. 21B is a rear view of optically detectable cartridge 2100 in a folded state. Cartridge 2100 is similar to cartridge 1600 discussed above, such that description of cartridge 1600 is applicable to cartridge 2100.

FIGS. 21A and 21B illustrate spoke regions separated from each other by collapsible regions (in this case bifold regions). In particular, a difference between cartridge 2100 and cartridge 1600 is that cartridge 2100 includes bifold regions between respective spoke regions. Bifold region 2110 extends from central region 1640, between spoke regions 1610 and 1620; bifold region 2120 extends from central region 1640, between spoke regions 1620 and 1630; and bifold region 2130 extends from central region 1640, between spoke regions 1630 and 1610.

In respective embodiments, boundaries between spoke regions and bifold regions are weakened along a fold line (for example, by perforations, scoring, or having the boundary be formed of thinner material). In FIG. 21A, boundary 2111 between spoke region 1610 and bifold region 2110; boundary 2112 between spoke region 1620 and bifold region 2110; boundary 2122 between spoke region 1620 and bifold region 2120; boundary 2123 between spoke region 1630 and bifold region 2120; boundary 2133 between spoke region 1630 and bifold region 2130; and boundary 2131 between spoke region 1610 and bifold region 2130 can all be weakened. Further, in respective embodiments, each bifold region is weakened along a line which runs through the respective bifold region. In particular, bifold region 2110 is weakened along a line 2115 which runs therethrough; bifold region 2120 is weakened along a line 2125 which runs therethrough; and bifold region 2130 is weakened along a line 2135 which runs therethrough. The weakened lines of cartridge 2100 allow each of the bifold regions to fold onto themselves as shown in FIG. 21B, such that cartridge 2100 is of a three-dimensional shape which fits within an interior volume of a mask unit.

Although FIGS. 21A and 21B and the corresponding description related to bifold regions, collapsible regions can take other forms. For example, a collapsible region could include many weakened lines therethrough, so that the collapsible region folds over itself multiple times in an accordion-like way. As another example, a collapsible region could be made of flexible or non-rigid material which crumples or folds over itself, even without weakened lines which run therethrough.

Although FIGS. 21A and 21B illustrate collapsible regions in the context of a cartridge for use with a mask unit have three side faces, the concept can be extended to cartridges for use with mask units having any appropriate number of faces, such as the cartridges 1700 and 1800, as non-limiting examples.

Figure 22:
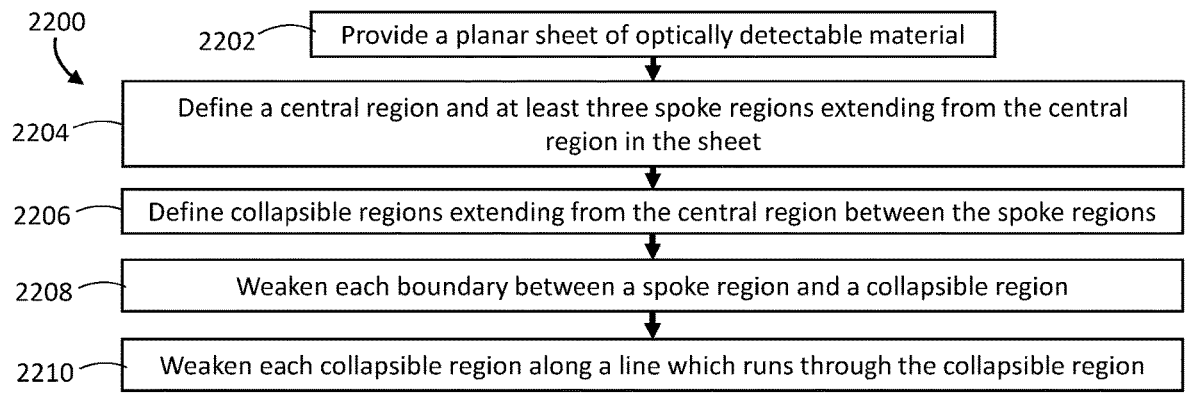
FIG. 22 is a flowchart diagram which illustrates an exemplary method for manufacturing optically detectable cartridges having collapsible regions.

FIG. 22 is a flowchart diagram which illustrates an exemplary method 2200 for manufacturing optically detectable cartridges with collapsible regions, such as cartridge 2100 discussed above. Such optically detectable cartridges can be used with the mask units and markers discussed herein. Method 2200 includes acts 2202, 2204, 2206, 2208, and 2210, though additional acts could be added, or acts could be removed or reordered as appropriate.

In act 2202, a planar sheet of optically detectable material is provided. Optical detectability is only required on one surface of the sheet, though opposing surfaces of the sheet could be optically detectable if desired. In implementations where the cartridge is intended to appear more bright than the mask unit to a tracking system, the cartridge material comprises, as examples, a reflective material, a light colored material, a retroreflective material, a diffuse material, or any other appropriate material. In implementations where the cartridge is intended to appear darker than the mask unit to a tracking system, the cartridge material comprises, as examples, a non-reflective material, a dark colored material, an absorptive material, or any other appropriate material.

In act 2204, a central region and at least three spoke regions extending from the central region are defined in the sheet. Any appropriate number of spoke regions are defined, including four or eight spoke regions, as non-limiting examples discussed above with reference to FIGS. 17A-17B and 18A-18B. The spoke regions are defined to have a size and shape approximating the interior size and shape of a side face of a mask unit into which the cartridge is intended to be inserted.

In act 2206, collapsible regions extending from the central region between the spoke regions are defined. In respective embodiments, such collapsible regions include bifold regions (or multifold regions which fold over themselves like an accordion), as further defined in acts 2208 and 2210. Alternatively, in respective embodiments, such collapsible regions include regions which crumple, flex, or otherwise collapse over themselves, such that weakened fold lines are not necessary. In this sense, acts 2208 and 2210 discussed below are optional.

Optionally, method 2200 may further include weakening each boundary between each of the spoke regions and the central region, to form a fold line at each boundary. In act 2208, each boundary between a spoke region and a collapsible region is weakened, to form a fold line at each boundary. In act 2210, each collapsible region is weakened along at least one line which runs through the collapsible region. Each act of weakening, in respective embodiments, entails perforating or scoring said boundaries, or forming the sheet with thinner regions which correspond to said boundaries. The formation of such fold lines facilitates easy and consistent folding of the sheet in desired ways, and the fold line or fold lines in the collapsible region enable the collapsible region to be folded over itself, even if the cartridge material is otherwise too rigid to be easily foldable.

Broadly, method 2000 in FIG. 20 and method 2200 in FIG. 22 can be summarized as providing a planar sheet of reflective material, defining at least three regions in the sheet, each region corresponding to a face of the mask unit into which the cartridge is to be inserted, and weakening each boundary between adjacent regions.

Although FIGS. 16A-22 discuss techniques related to foldable cartridges, the optically detectable cartridges described herein are not required to be foldable. Rather, in respective embodiments, the optically detectable cartridges discussed herein are rigid, three-dimensional structures which have a shaping matching a shape of an interior volume of a desired mask unit without any need for folding.

FIGS. 23A-23H are side cross-sectional views of an exemplary mask unit 2310, which receives an optically detectable cartridge 2390 or 2392 within an interior volume thereof. FIGS. 23A-23H illustrate exemplary mechanisms for securing a cartridge in a mask unit, which, in respective embodiments, is applicable to any of the cartridges or mask units discussed herein. Although many of the features in FIGS. 23A-23H are shown as securing cartridge 2390 in the interior volume of mask unit 2310, it is also possible for cartridge 2390 to include supportive backing, like backing sections 1910, 1920, and 1930 in cartridge 1900. Features which are shown as securing cartridge 2390 could instead secure such backing, which in turn secures the cartridge.

Figure 23A:
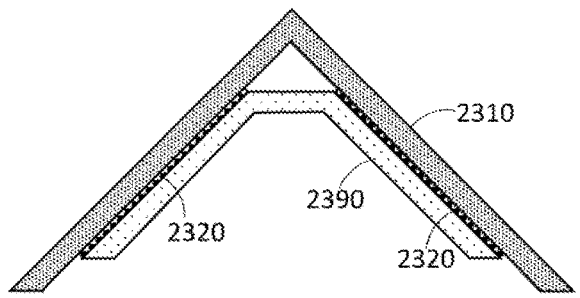
FIGS. 23A, 23B, 23C, 23D, 23E, 23F, 23G, and 23H are side cross-sectional views of exemplary mask units and mechanisms for securing cartridges therein.

FIG. 23A shows cartridge 2390 as being secured to mask unit 2310 by adhesive 2320. Such adhesive should preferably be non-permanent, such that cartridge 2390 can be removed from mask unit 2310 without damage to either component. Although, in embodiments, the adhesive 2320 can be applied to either or both of mask unit 2310 or cartridge 2390 prior to inserting cartridge 2390 into mask unit 2310, it can be preferable to apply adhesive 2320 to an interior surface of mask unit 2310, then insert cartridge 2390 into the interior volume of mask unit 2310. In this way, adhesive 2320 is limited from being positioned on regions of cartridge 2390 which are intended to be detectable through openings in mask unit 2310. Alternatively, in an embodiment, adhesive 2320 is applied to cartridge 2390 during manufacturing, with adhesive 2320 being positioned outside of regions of cartridge 2390 which are intended to be detectable through openings in mask unit 2310. Consequently, adhesive 2320 should have limited to no impact on the detectability of the cartridge 2390 through the openings.

In FIG. 23A, cartridge 2390 is shown as being inset relative to mask unit 2310. However, in any of the implementations discussed herein, cartridge 2390 could extend such that the rear of cartridge 2390 (the bottom edge in the orientation of FIGS. 23A-23H) is flush with the rear edge of mask unit 2310, unless physical structures require otherwise.

Figure 23B:
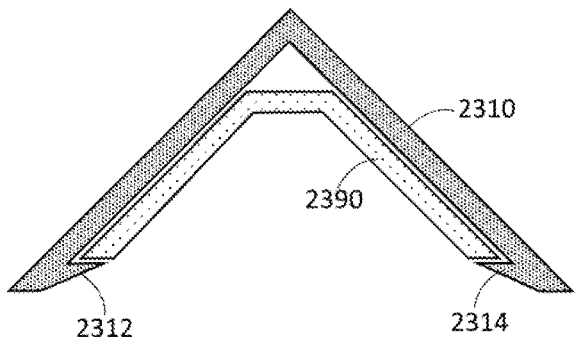

FIG. 23B shows mask unit 2310 as including clips 2312 and 2314 which clip over and secure cartridge 2390 in the interior volume of mask unit 2310. Although two clips 2312 and 2314 are shown, any appropriate number of clips could be used, which can be based partly on the number of side faces of the mask unit. Further, in an embodiment, clips 2312 and 2314 comprise a single continuous clip which at least partially encircles the interior volume of the mask unit 2310.

Figure 23C:
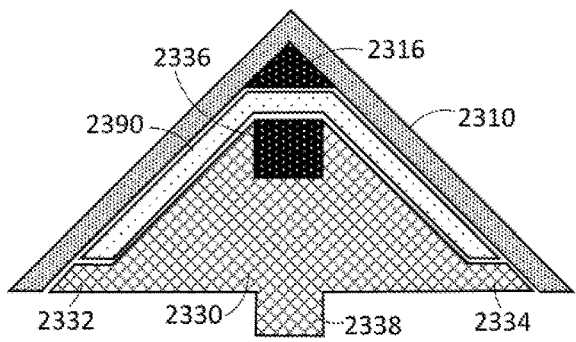

FIG. 23C shows a support unit 2330 which can be positioned within the interior volume of the mask unit 2310 together with cartridge 2390. Support unit 2330 secures cartridge 2390 in the interior volume of mask unit 2310. In the example of FIG. 23C, support unit 2330 secures itself and cartridge 2390 in mask unit 2310 with magnetic force between element 2316 on mask unit 2310 and element 2336 in support unit 2330. For example, element 2316 is ferromagnetic, and element 2336 is magnetic. As another example, element 2316 is magnetic, and element 2336 is ferromagnetic. As yet another example, elements 2316 and 2336 are both magnetic, with opposite polarity surfaces facing each other. In each of these examples, element 2316 and element 2336 are drawn together by magnetic force, which holds support unit 2330 and cartridge 2390 in the interior volume of mask unit 2310. In some implementations, elements 2316 and 2336 are formed as individual components, and installed in mask unit 2310 and support unit 2330, respectively. In other implementations, elements 2316 and 2336 are formed together with mask unit 2310 and support unit 2330, respectively. For example, mask unit 2310 and/or support unit 2330 are magnetized. As another example, one of mask unit 2310 and/or support unit 2330 is formed of ferromagnetic material, and the other of mask unit 2310 and/or support unit 2330 has a magnet installed therein.

FIG. 23C also shows support unit 2330 as including protrusions 2332 and 2334, which abut against cartridge 2390 and help align and secure cartridge 2390. However, these protrusions are optional, and omitted if desired.

It is also possible to secure cartridge 2390 within the interior volume of the mask unit 2310 with magnetic force, without support unit 2330. For example, element 2336 is affixed directly to cartridge 2390 (e.g. as backing section 1930 described with reference to FIGS. 19A-19B, or a portion thereof). Similar to as described above, in examples, element 2316 is ferromagnetic, and element 2336 is magnetic; element 2316 is magnetic, and element 2336 is ferromagnetic; elements 2316 and 2336 are both magnetic, with opposite polarity surfaces facing each other. In each of these examples, element 2316 and element 2336 are drawn together by magnetic force, which holds cartridge 2390 in the interior volume of mask unit 2310.

Figure 23D:
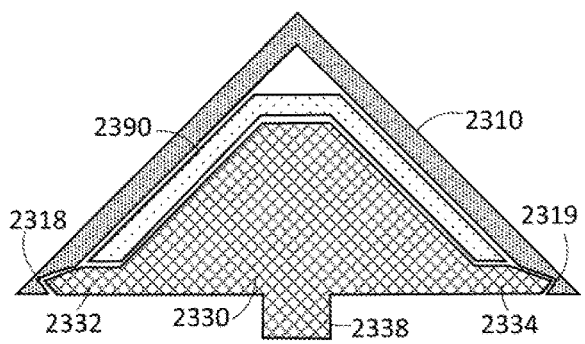

FIG. 23D illustrates support unit 2330 as being secured in the interior volume of mask unit 2310 by protrusions 2332 and 2334, which extend into recesses 2318 and 2319, respectively, of mask unit 2310. Protrusions 2332 and 2334 are complementary to recesses 2318 and 2319, and can be considered as "complementary clips". Further, two protrusions 2332 and 2334 are illustrated as extending into two recesses 2318 and 2319; however, any appropriate number of complementary protrusions and recesses can be used, for example, based at least partly on the number of side faces of mask unit 2310. Further, in an example, protrusions 2332 and 2334 are a single continuous protrusion, which at least partially encircles support unit 2330, and recesses 2318 and 2319 are a single continuous recess, which at least partially encircles mask unit 2310.

Figure 23E:
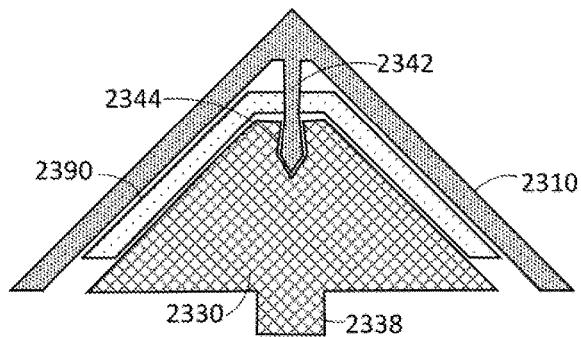

FIG. 23E illustrates support unit 2330 as being secured in the interior volume of mask unit 2310 by a protrusion 2342 extending from mask unit 2310, through cartridge 2390, into a recess 2344 in support unit 2330. In an embodiment, protrusion 2342 has an end region distal from mask unit 2310, which is wider than an opening of recess 2344. Further, in an embodiment, protrusion 2342 and/or support unit 2330 are made of a resilient material which allows protrusion 2342 to be forced into recess 2344, with the opening of recess subsequently gripping and securing protrusion 2342. In this way, protrusion 2342 and recess 2344 can be considered as "corresponding clips". Additionally, in an embodiment, cartridge 2390 has a hole therein through which protrusion 2342 passes, or cartridge 2390 is made of sufficiently thin or pierceable material such that protrusion 2342 pierces through cartridge 2390 in use. Protrusion 2342 consequently helps to align cartridge 2390.

Figure 23F:
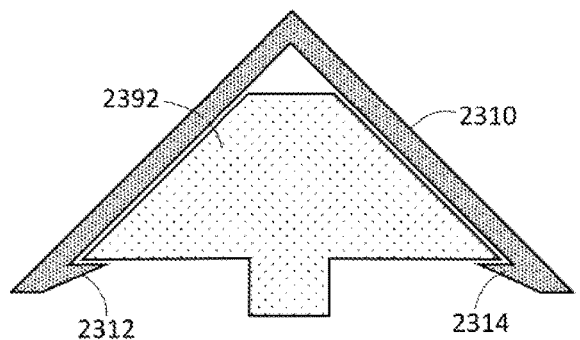

FIG. 23F illustrates an exemplary optically detectable cartridge 2392 which is not hollow, but rather fits in and occupies a significant portion of the interior volume of mask unit 2310. That is, cartridge 2392 has a shape which matches a shape of the interior volume of mask unit 2310. For example, in an embodiment, cartridge 2392 comprises a three-dimensional structure designed to fit in mask unit 2310 without any folding. Cartridge 2392 is secured in mask unit 2310 by clips 2312 and 2314, similarly to as in FIG. 23B. In some examples, cartridge 2392 comprises deformable foam, which is compressed prior to insertion into mask unit 2310, and expands to fill the interior volume of mask unit 2310 once positioned in the interior volume thereof. In such examples, the cartridge 2392 could be formed entirely of such foam, or cartridge 2392 could be formed with a foam core having optically detectable material affixed to a surface thereof.

Figure 23G:
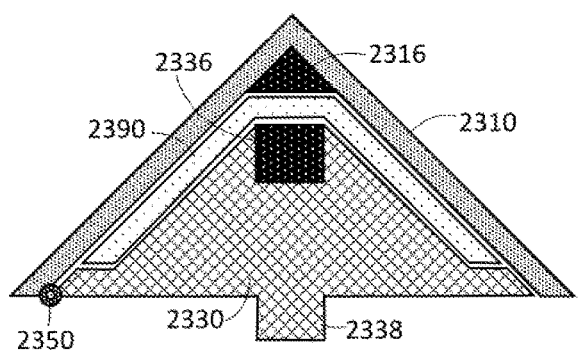
Figure 23H:
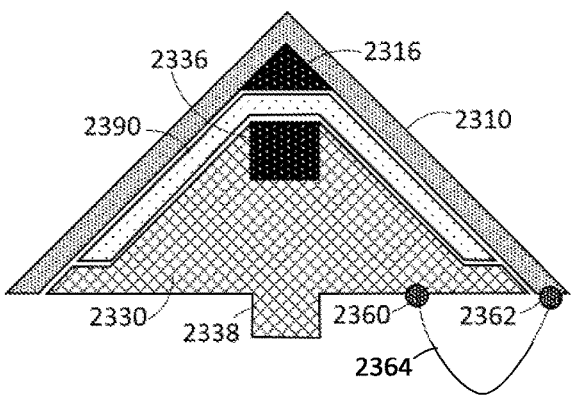

FIG. 23G illustrates an exemplary implementation where support unit 2330 is coupled to mask unit 2310 by a hinge 2350. FIG. 23H illustrates an exemplary implementation where support unit 2330 is coupled to mask unit 2310 by a linkage 2364. In an embodiment, linkage 2364 comprises a flexible string, cord, or wire, or a rigid connector such as a rod. One end of linkage 2364 is coupled to mask unit 2310 by coupling 2362 and the other end of linkage 2364 is coupled to support unit 2330 by coupling 2360. In these implementations, support unit 2330 is removable from the interior volume of mask unit 2310, while still being attached thereto. This allows cartridge 2390 to be inserted into and removed from the interior volume of mask unit 2310, while keeping support unit 2330 together with mask unit 2310. This prevents the support unit 2330 from falling to the floor (and losing sterility) if support unit 2330 is accidently dropped. Further, support unit 2330 is prevented from being misplaced or lost. Additionally, in an embodiment, support unit 2330 is also coupled to other portions of a marker in addition to the mask unit, such as to any connectors or structural features of the marker. Although FIGS. 23G and 23H show elements 2316 and 2336 for securing support unit 2330 in mask unit 2310, any other described securing mechanisms can be used.

Any of the securing mechanisms discussed in FIGS. 23A-23H can be used together in combination, such that a cartridge is secured in a mask unit by multiple securing mechanisms, for improved stability. Additionally, cartridges can be removed from the mask unit 2310 by pressing on any exposed clips (e.g. clips 2312, 2314), prying the cartridge out (e.g. prying recesses 2318 and 2319 open, or prying a side of the support unit away from edges of the mask unit), or pressing on the cartridge through at least one opening on a face of the mask unit. Further, FIGS. 23C-23E, 23G, and 23H illustrate support unit 2330 as including an optional handle 2338, by which the support unit 2330 can be grabbed to remove the support unit 2330 from the mask unit 2310, releasing the cartridge 2390. Cartridge 2392 in FIG. 23F is shown as including a similar handle. In addition or alternative to the securing mechanisms discussed above, a cartridge or support unit can be secured in a mask unit by a friction fit.

Further still, in an embodiment, cartridge 2390 is adhered to support unit 2330 prior to insertion into the interior volume of mask unit 2310, preferably by a non-permanent adhesive.

Figure 24A:
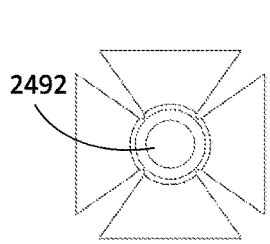
FIG. 24A is a front view of an exemplary foldable cartridge having an alignment hole therethrough.
Figure 24B:
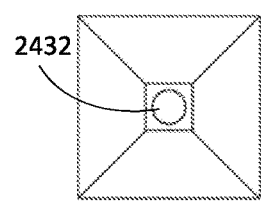
FIG. 24B is a front view.
Figure 24C:
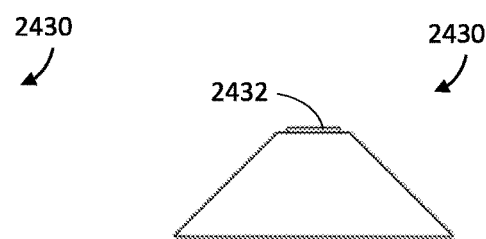
FIG. 24C is a side view, of an exemplary support unit having a post to be aligned with the hole of the cartridge in FIG. 24A.

FIGS. 24A-24C illustrate an exemplary implementation where a hollow cartridge and a support unit can have complimentary alignment mechanisms. FIG. 24A is a front view of an optically detectable cartridge 2490, prior to folding (though a hollow, non-foldable cartridge could also be used). FIG. 24B is a front view of a support unit 2430 sized and dimensioned to support cartridge 2490 in a mask unit. FIG. 24C is a side view of support unit 2430. Cartridge 2490 is shown as having a hole 2492 therethrough, to be received on a post 2432 of support unit 2430. This hole and post arrangement will enable cartridge 2490 to be aligned on support unit 2430, prior to insertion into a mask unit. Alternatively, the post and hole arrangement will align and position cartridge 2490 already in a mask unit when support unit 2430 is subsequently inserted into the mask unit. Thus, alignment mechanisms on the cartridge and support unit can make inserting and securing cartridges in a mask unit easier, and achieve better alignment.

Although FIGS. 23A-23H and 24A-24B illustrate singular cartridges being secured in singular mask units, the illustrated mechanisms are applicable to each mask unit and cartridge combination in markers having a plurality of mask units and cartridges. For example, in a marker with a plurality of mask units, a plurality of support units like support units 2330 are provided, with each support unit securing a cartridge in a respective mask unit. In such an example, the mask units, cartridges, and support units are preferably sized and shaped such that cartridges and support units fit in the interior volume of the mask units in any combination; that is, the cartridges and support units are preferably interchangeable between mask units. As another example, in a marker with a plurality of mask units, a plurality of non-foldable cartridges like cartridge 2392 is provided, for insertion into respective mask units. In such an example, the mask units and cartridges are preferably sized and shaped such that each cartridge fits in the interior volume of any of the mask units; that is, the cartridges are preferably interchangeable between mask units.

As mentioned above, in the markers discussed herein, it is generally desirable to achieve a high contrast between cartridges and mask units. Such high contrast provides clear delineation of the openings in a mask unit, and thus results in the openings being more easily detected and localized by a tracking system. As mentioned above, one of the mask unit(s) or the cartridge(s) can be detectable by a tracking system with greater brightness than the other of the mask unit(s) or the cartridge(s). For example, one of the cartridge(s) or the mask unit(s) can comprise (be coated or formed of) material which is reflective or diffusive of light, whereas the other of the cartridge(s) or the mask unit(s) can comprise material which is non-reflective or absorptive of light. Such reflective materials include, for example, spectrally reflective materials, retroreflective materials, or diffusively reflective materials (such as opaque diffuse). In some implementations, diffusive cartridge materials could be paired with a light source which outputs light to an interior volume of a mask unit, as discussed later with reference to FIGS. 30A-30C.

In the case of reflective, retroreflective, or diffusive cartridges, because the surfaces of the cartridge which are viewed are generally planar, detection based on the cartridges herein can be more effective and robust compared to reflective spheres as discussed with reference to FIGS. 2A-2C and 3A-3B. For example, a retroreflective surface can be formed with a plurality of microballs or other micro-structures disposed across the surface. With planar surfaces, a smooth protective film can be layered over top such micro-structures, without substantially affecting the reflective performance thereof. With spherical surfaces on the other hand, this is more difficult, as a transparent layer over the sphere will refract light incident on and reflected by the sphere. Consequently, if liquid such as water or blood gets on a sphere, capillary action between the micro-structures can make removal of the liquid difficult. Further, the presence of such liquid can harm the desired reflective properties of the sphere, making tracking inaccurate or impossible. With a planar surface having a smooth protective layer, liquid can be easily wiped away, and such liquid will have less significant impacts on the tracking even if present. Similar protective films could also be applied over planar reflective and diffuse materials (not only retroreflective materials). Consequently using planar cartridge surfaces can be more robust than spheres.

Additionally, with spherical markers, the shape of detectable features is defined by the edges of the sphere, and thus accurate sphere positioning is paramount. However, accurate sphere positioning can be difficult to achieve, such as discussed with reference to FIGS. 3A and 3B, for example. Further, if stray light is detected behind a sphere, this could inaccurately be interpreted as an edge of the sphere. In the markers discussed herein, the detectable features are defined by openings of a mask unit, and consequently tracking can still be accurate even if a cartridge is inaccurately positioned in the mask unit, as long as the mask unit itself is accurate. Further, the mask unit will block stray light from behind the marker around the openings. As a result, the markers discussed herein can achieve more accurate tracking and be less prone to errors.

In the markers discussed herein, in order to maximize contrast and enhance detection of the optically detectable cartridge or cartridges, at least an exterior surface of either the mask unit or the cartridge comprises (e.g. is preferably formed or coated with) a non-reflective or light absorptive material. Exemplary materials or coatings include anodized aluminum, plastic, rubber, dark paint, powder coating, or any other appropriate materials. Many factors could be considered or adjusted when selecting or designing cartridge and mask unit surfaces, including material, texture (e.g. roughness/smoothness), surface preparation (e.g. bead blasting the surface to make it diffuse), color, or other appropriate factors. Further, mask units and cartridges can be made of a sterilizable or autoclavable material, such that the marker body could be sterilized/autoclaved. Exemplary materials could include medical grade titanium, aluminum, stainless steel, amorphous thermoplastic polyetherimide (PEI) (e.g. Ultem™ of SABIC), high-performance thermoplastic (e.g. Radel™ of Solvay SA), or any other appropriate material. In some implementations, cartridges can be intended for single use. That is, cartridges can be used once, and discarded after use. In such implementations, cartridges can be provided sterilized, and do not necessarily have to be sterilizable or autoclavable by means available to hospitals and clinics. For example, cartridges could be made of a thin foldable material that is not durable enough to withstand steam or heat sterilization.

In addition, the mask units discussed herein are illustrated with each face as being flat, and faces being separated from each other by a sharp boundary or corner. However, this is not necessarily required. A "face" could include a curved surface, and adjacent faces may be separated conceptually, rather than by a sharp boundary or corner. For example, boundaries between faces could be rounded, with each face being defined as a group of openings or opening features which are trackable.

Any of the optically detectable cartridges described herein can include patterns or features which enable more specific detection, as exemplified in FIGS. 25A-25C, 26A-26C, and 27A-27B.

FIGS. 25A-25C are side views of a side face of a mask unit 2510 and an optically detectable cartridge 2590. FIG. 25A illustrates mask unit 2510 and cartridge 2590 separately. The visible side of mask unit 2510 has an opening 2512 therein open to an interior volume of the mask unit 2510. Cartridge 2590 has a hole 2592 therethrough. FIG. 25B shows cartridge 2590 inserted in the interior volume of mask unit 2510. Hole 2592 is smaller than, and aligned with, opening 2512, such that a ring of the optically detectable material of cartridge 2590 is exposed through opening 2512. FIG. 25C illustrates the same view of mask unit 2510, but as seen by an image sensor designed to be sensitive to the optically detectable material of cartridge 2590. The pattern seen by the image sensor is that of a ring delineated by opening 2512 and hole 2592. Such rings can be used to detect not only a pose of mask unit 2510, but can also be used to identify which face of mask unit 2510 is being viewed. For example, other faces of cartridge 2590 may not have a hole such as hole 2592, or may have a different pattern thereon, such that the ring identifies the face being viewed. Such identification can be unique (i.e., each face has a different, detectable pattern), or can at least reduce a number of candidate faces which may be viewed (e.g., a mask unit and cartridge combination could have a first set of faces with no holes in the cartridge, and a second set of faces with holes in the cartridge).

FIGS. 26A-26C are side views of a side face of a mask unit 2610 having an opening 2612 therethrough, and an optically detectable cartridge 2690. FIGS. 26A-26C are similar to FIGS. 25A-25C, and description of FIGS. 25A-25C can be applicable to FIGS. 26A-26C.

One difference between FIGS. 26A-26C and FIGS. 25A-25C is that in FIGS. 26A-26C, instead of a hole, cartridge 2690 has an optically non-detectable pattern 2692 thereon. FIGS. 26A-26C show pattern 2692 as a cross, but any appropriate pattern could be used. The pattern 2692 could be printed, painted, or drawn on cartridge 2690, or cartridge 2690 could be manufactured such that optically detectable material is placed everywhere except pattern 2692. Alternatively, pattern 2692 could be cut away from cartridge 2690. As shown in FIG. 26B, pattern 2692 can align with opening 2612, such that pattern 2612 is detected (or rather, the optically detectable cartridge is detected around the pattern). This pattern can be used to determine what face of the combination of mask unit 2610 and cartridge 2690 is being viewed.

By using different patterns for different faces, unique identification of faces can be achieved. Further, aligning patterns of the cartridge with certain openings of a face can be useful to identify faces. In this regard, FIGS. 27A and 27B illustrate side views of a mask unit 2700. FIG. 27A shows a face 2710 of mask unit 2700, whereas FIG. 27B shows a face 2720 of mask unit 2700. Face 2710 includes openings 2711, 2712, 2713, and 2714 arranged in a first pattern, and face 2720 includes openings 2721, 2722, 2723, and 2724 arranged in the first pattern. A cartridge inserted into the interior volume of mask unit 2700 has a hole 2715 therethrough, which is aligned with opening 2711 of face 2710. Further, the cartridge also has holes 2725 and 2726 therethrough, which are aligned with openings 2722 and 2723 of face 2720. Consequently, a tracking system will see a ring pattern in the top left of mask unit 2700 when face 2710 is viewed, or will see ring patterns in the top right and bottom left of mask unit 2700 when face 2720 is viewed. In this way, patterns of holes or non-detectable regions on the cartridge can be used to identify which face of a marker is being viewed.

In addition to being useful for identifying different faces of a marker, aligning optically non-detectable patterns or hole of cartridges with openings of mask units can also be useful for identifying and distinguishing between multiple markers. FIGS. 28A-28E illustrate examples in this regard.

FIG. 28A is a front view of an optically detectable cartridge 2890 in an unfolded configuration. Cartridge 2890 can have an optically detectable surface with the exception of optically non-detectable patterns 2892 and 2894. Patterns 2892 and 2894 are shown as being cross-shaped, but could be any appropriate shape. Further, patterns 2892 and 2894 are shown as optically non-detectable areas of the surface, but could also comprise holes through the cartridge 2890. Further still, patterns 2892 and 2894 could be positioned on any appropriate spokes of cartridge 2890, and any appropriate number of patterns could be included.

FIGS. 28B, 28C, and 28D are front views of markers 2810, 2820, and 2830, respectively. The shapes of markers 2810, 2820, and 2830 are shown as corresponding to marker 1300 discussed above, but any appropriate shape could be used. Preferably, each mask unit in markers 2810, 2820, and 2830 can be similarly sized and shaped to receive cartridge 2890, such that the interior volumes of mask units of markers 2810, 2820, and 2830 can be populated by a plurality of identical cartridges 2890. However, an orientation of cartridge 2890 in each of the mask units can define a pattern seen through the openings of each mask unit. Markers 2810, 2820, and 2830 are each illustrated as having the same structure of mask units, with identical cartridges inserted in the interior volume of each mask unit. However, the orientation of cartridges within mask units can be different, resulting in uniquely identifiable patterns for each marker. FIGS. 28B-28C also show, as dotted regions, the locations of optically non-detectable patterns which are not aligned with an opening of a mask unit, so that the orientation of each cartridge can be understood. In the examples of markers 2810, 2820, and 2830, each opening in each mask unit can either have only optically detectable material of a cartridge exposed therethrough, or can have optically detectable material and an optically non-detectable pattern exposed therethrough. Specifically, for round openings and cross-shaped patterns 2892 and 2894, each opening can appear to a tracking system as either a round feature, or a round feature with a cross therethrough.

FIG. 28E illustrates an exemplary side or bottom view of any one of markers 2810, 2820, or 2830, when viewed in the directions V1, V2, V3, or V4. Each visible opening is labelled as T (top), B (bottom), L (left), or R (right), with the relative direction referring to the direction as seen according to the view. FIG. 28F is a table which indicates, for each view V1, V2, V3, or V4 of each marker 2180, 2820, and 2830, what will be detected by the tracking system for each opening T, B, L, and R. As can be seen in FIG. 28F, each set of openings visible for a given view are unique to each face of each marker. That is, each conceptual face of a marker can be uniquely specified by a pattern in the openings of the face. For example, the pattern of openings for marker 2810 in V1 is different from the pattern of openings in each of the other views of marker 2810, and is different from the pattern of openings in each view of markers 2820 and 2830. This applies to each of the views of each marker.

In order to ensure that cartridges are installed in mask units of marker in the correct orientation to uniquely identify the marker and faces thereof, and/or to match patterns expected by a tracking system, alignment features can be included in the mask unit and/or the cartridges, as discussed below with reference to FIGS. 29A-29Z. Although FIGS. 29A-29Z generally show singular mask units or cartridges, the features described could be applied to a plurality of mask units or cartridge in a marker.

Figure 29A:
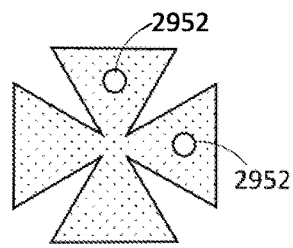
FIGS. 29A, 29B, 29C, 29D, 29E, 29F, 29G, 29H, 29I, 29J, 29K, 29L, 29M, 29N, 29O, 29P, 29Q, 29R, 29S, 29T, 29U, 29V, 29W, 29X, 29Y, and 29Z illustrate exemplary alignment features for mask unit and cartridges, to control alignment of cartridges in the interior volume of mask units.

FIG. 29A is a front view of an optically detectable cartridge having optically non-detectable regions 2952 therein. Optically non-detectable regions 2952 are illustrated as being round holes through the cartridge, but could be any appropriate shape, or could be an optically non-detectable material as part of the cartridge.

Figure 29B:
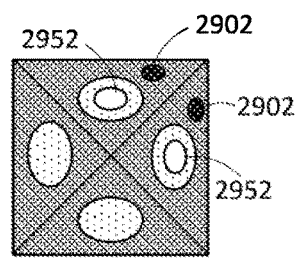

FIG. 29B is a front view of a mask unit having features 2902 thereon, and having the cartridge of FIG. 29A positioned in an interior volume thereof. Features 2902 provide a visual indication of the correct orientation of the cartridge. In the example of FIG. 29B, features 2902 indicate openings of the mask unit with which optically non-detectable regions 2952 should be aligned. This allows a person installing the cartridge to visually identify when the cartridge is properly aligned, and improperly aligned, by viewing the front of the marker. Features 2902 could for example be protrusions, indentations, embossing, paint, or any other feature which can be discerned by the human eye. However, since features 2902 are positioned on the front of the mask unit, features 2902 should not be detectable by a tracking system (or significantly less detectable than the optically detectable cartridge), so as to not interfere with detection and tracking of the mask unit.

Figure 29C:
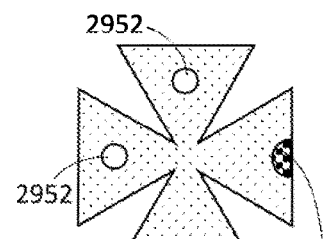
Figure 29D:
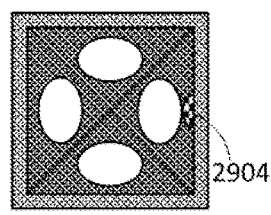

FIG. 29C is a rear view of an optically detectable cartridge similar to that shown in FIG. 29A. The cartridge is shown as including feature 2954 on its rear surface. FIG. 29D is a rear view of a mask unit similar to the mask unit of FIG. 29B, and including feature 2904 on an interior surface thereof. Prior to insertion of the cartridge of FIG. 29C into the mask unit of FIG. 29D, feature 2954 can be aligned with feature 2904. Thus, features 2954 and 2904 together provide visible alignment cues. Feature 2904 and 2954 can for example be indentations, embossing, paint, stickers, or any other appropriate visible features.

Figure 29E:
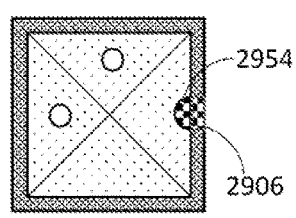
Figure 29F:
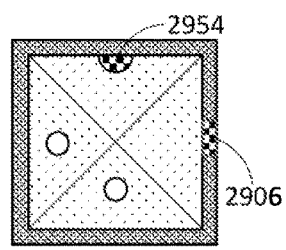

FIGS. 29E and 29F are rear views of a mask unit having the cartridge of FIG. 29C inserted therein. In FIGS. 29E and 29F, the mask unit has feature 2906 on an edge thereof. Feature 2906 can be similar to feature 2904, except that feature 2906 is visible even when the cartridge is positioned in the interior volume of the mask unit. In this way, correct alignment of the cartridge can be verified after the cartridge is inserted. FIG. 29E illustrates the cartridge in correct alignment, with features 2954 and 2906 being aligned. FIG. 29F illustrates the cartridge in incorrect alignment, with features 2954 and 2906 not being aligned.

Figure 29G:
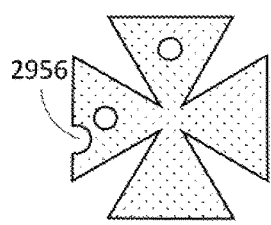
Figure 29H:
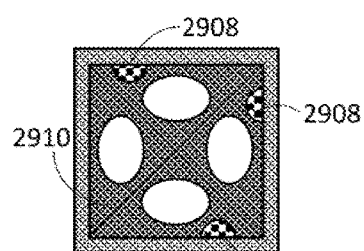
Figure 29I:
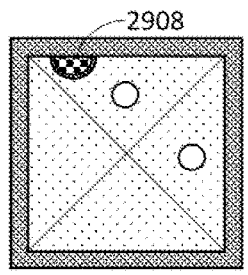
Figure 29J:
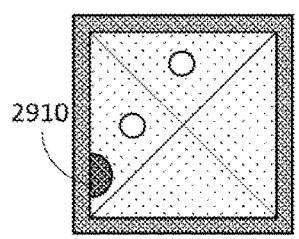

FIG. 29G is a rear view of an optically detectable cartridge similar to the cartridge in FIG. 29A. The cartridge of FIG. 29G has a notch 2956 therein. FIG. 29H is a rear view of a mask unit into which the cartridge of FIG. 29G can be inserted. The mask unit of FIG. 29H includes features 2908, which can be similar to feature 2904 discussed above. In the example of FIG. 29H, a feature is included on all but one of the interior walls of the mask unit, with the remaining interior wall of the mask unit lacking a feature in the position 2910. FIGS. 29I and 29J are rear views of the mask unit of FIG. 29H having the cartridge of FIG. 29G positioned therein. In FIG. 29I, the cartridge is improperly aligned, such that feature 2908 will be visible through notch 2956. This can be true for all but one of the possible orientations of the cartridge, such that a visible indication is provided that the cartridge is misaligned. In FIG. 29J, the cartridge is properly aligned, such that position 2910 is visible through notch 2956. Since none of features 2908 indicating improper alignment are visible, this indicates the cartridge is properly aligned. In alternative implementations, a feature could be provided at position 2910 which when visible indicates that the cartridge is properly aligned. This feature at position 2910 could be in addition to the features 2908, or could be instead of the features 2908. If a visible feature is included at position 2910 in addition to features 2908, the feature at position 2910 should be visibly different from features 2908, for example by being a different color.

Figure 29K:
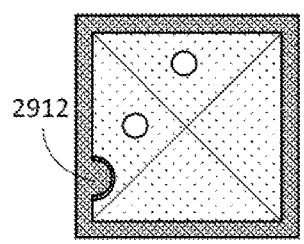
Figure 29L:
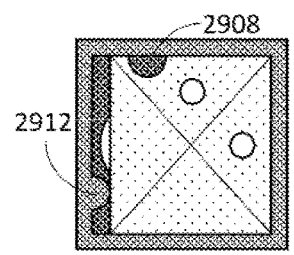

FIGS. 29K and 29L are rear views of another mask unit into which the cartridge of FIG. 29G can be inserted. The mask unit of FIGS. 29K and 29L includes a protrusion 2912 intended to align with the notch 2956 of the cartridge. FIG. 29K shows the cartridge being properly aligned in the mask unit, such that protrusion 2912 aligns with notch 2956 and the cartridge is properly seated in the mask unit. FIG. 29L shows the cartridge being misaligned in the mask unit such that protrusion 2912 pushes against part of the cartridge, causing the cartridge to be visibly improperly seated in the mask unit. This should prompt the person installing the cartridge to correct the orientation thereof.

Figure 29M:
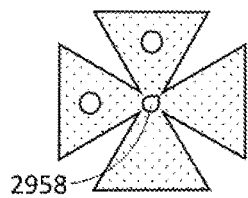
Figure 29N:
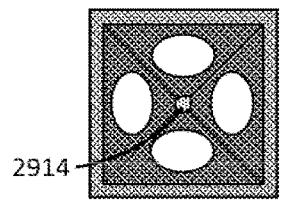

FIG. 29M is a rear view of an optically detectable cartridge having an alignment hole 2958 therethrough. FIG. 29N is a rear view of a mask unit having an alignment post 2914 protruding therefrom. The cartridge of FIG. 29M is insertable into the interior volume of the mask unit of FIG. 29N, with alignment hole 2958 receiving alignment post 2914. Alignment hole 2958 and alignment post 2914 can have matching asymmetrical cross-sectional shapes such that alignment hole 2958 can only receive alignment post 2914 in a specific orientation. In this way, alignment post 2914 can prevent the cartridge of FIG. 29M from being inserted into the interior volume of the mask unit unless the cartridge is properly aligned.

Figure 29O:
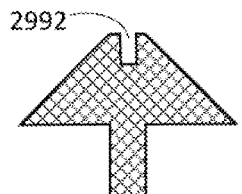

In some implementations, optically detectable cartridges can be made of weak, flimsy, or flexible material, which is not sufficiently sturdy to control alignment of the cartridge on a post such as alignment post 2914. FIG. 29O shows a side-cross-sectional view of a cartridge inserting tool, which includes an alignment hole 2992, shaped to receive alignment post 2914 in a specific alignment. A cartridge such as that in FIG. 29M could first be placed on the cartridge inserting tool of FIG. 29O, and subsequently inserted into the interior volume of the mask unit of FIG. 29N with the cartridge inserting tool. In this way, the cartridge inserting tool can provide correct alignment to the cartridge. The cartridge inserting tool could have identifiable features such as those detailed above to ensure correct alignment of the cartridge on the tool prior to insertion into the mask unit.

Figure 29P:
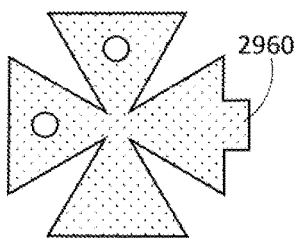
Figure 29Q:
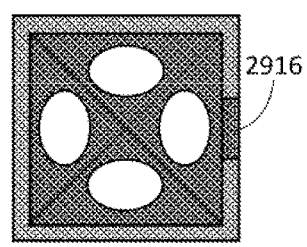

FIG. 29P is a rear view of an exemplary optically detectable cartridge having a tab 2960 protruding therefrom. FIG. 29Q is a rear view of a mask unit having a recess 2916 at an edge thereof. The mask unit of FIG. 29Q can receive the cartridge of FIG. 29P, such that tab 2960 aligns with recess 2916. If the cartridge is improperly aligned, tab 2960 will be bent by a wall of the mask unit, to stick out of the mask unit, thus acting as a visible indicator that the cartridge is not aligned properly. Alternatively, if the cartridge is made of a rigid or resilient material, and the cartridge is improperly aligned, tab 2960 can push against a wall of the mask unit and prevent the cartridge from seating properly in the mask unit.

Figure 29R:
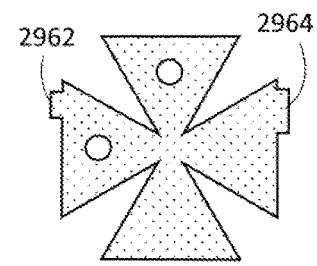
Figure 29S:
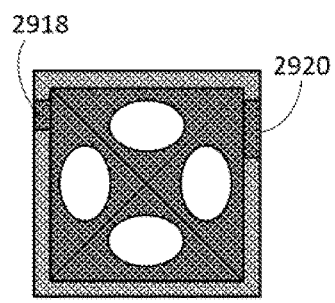

FIG. 29R is a rear view of an exemplary optically detectable cartridge similar to the cartridge of FIG. 29P. The cartridge of FIG. 29R includes two tabs 2962 and 2964, which can be of different sizes or the same size. In alternative implementations, more tabs could be included. FIG. 29S is a rear view of an exemplary mask unit similar to the mask unit shown in FIG. 29Q. The mask unit of FIG. 29S includes two recesses 2918 and 2920, sized to receive tabs 2962 and 2964, respectively. If the cartridge is improperly aligned, tab 2962 and/or tab 2964 will be bent by walls of the mask unit, to stick out of the mask unit, thus acting as visible indicators that the cartridge is not aligned properly. Alternatively, if the cartridge is made of a rigid or resilient material, and the cartridge is improperly aligned, tab 2962 or tab 2964 can push against walls of the mask unit and prevent the cartridge from seating properly in the mask unit.

Figure 29T:
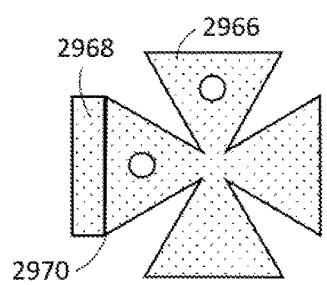
Figure 29U:
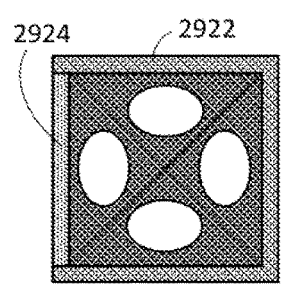
Figure 29V:
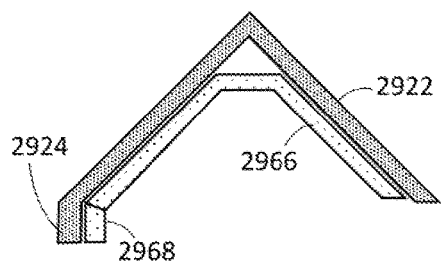
Figure 29W:
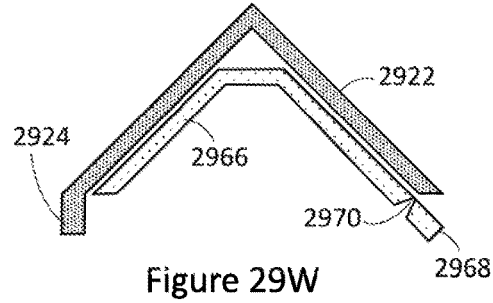

FIG. 29T is a rear view of an exemplary optically detectable cartridge 2966 having a tab 2968 protruding therefrom. A weakened region 2970 can be positioned between tab 2968 and the rest of cartridge 2966. Weakened region 2970 could be for example a score line. FIG. 29U is a rear view of an exemplary mask unit 2922 which can receive cartridge 2966. Mask unit 2922 includes a protrusion 2924 extending rearward from the mask unit. FIG. 29V is a side cross-sectional view of mask unit 2922 with cartridge 2966 properly inserted therein. Protrusion 2924 presses against tab 2968, and tab 2968 bends inward, covering weakened region 2970. FIG. 29W is a side cross-sectional view of mask unit 2922 with cartridge 2966 improperly inserted therein. Tab 2968 extends beyond the mask unit 2922, without being bent inward, such that weakened region 2970 can be seen. Weakened region 2970 can be colored or otherwise made obvious in appearance, such that a visual indicator is provided that the cartridge is not properly seated. Alternatively, protrusion 2924 could be provided on all sides but one of the mask unit 2922, and the weakened region 2970 could act as an indicator that the cartridge is properly seated when visible.

Figure 29X:
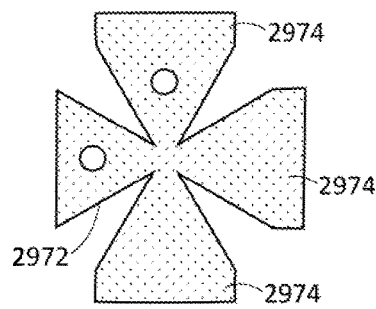
Figure 29Y:
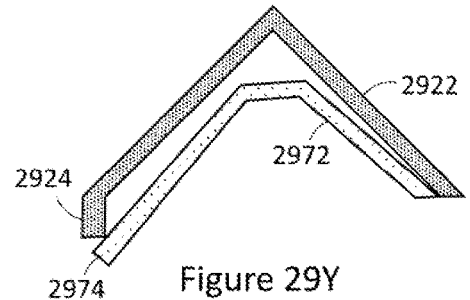

FIG. 29X shows an optically detectable cartridge 2972 which can be inserted into the mask unit 2922 discussed with reference to FIG. 29U. Cartridge 2972 includes tabs 2974 extending therefrom. Further cartridge 2972 is formed of a rigid or resilient material. FIGS. 29Y and 29Z are side cross-sectional views which show cartridge 2972 inserted into mask unit 2922. In FIG. 29Y, cartridge 2972 is improperly aligned, such that one of tabs 2974 contacts protrusion 2924 and prevents cartridge 2972 from seating properly in mask unit 2922. In FIG. 29Z, cartridge 2972 is properly aligned, such that none of tabs 2974 contact protrusion 2924, and thus cartridge 2972 seats properly in mask unit 2922.

Figure 29Z:
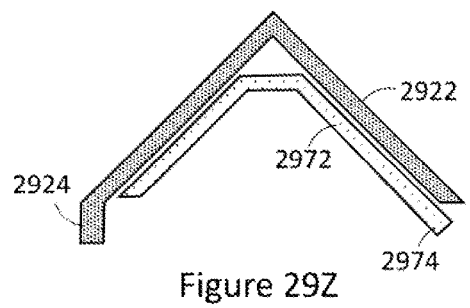

FIGS. 29A-29Z illustrate several exemplary techniques and mechanisms for aligning a cartridge within a mask unit. Unless they are mechanically contradictory, any of these mechanisms or techniques can be used in combination as appropriate for a given application. For example, features 2902 shown in FIG. 29B could be included in any of the mask units shown in FIG. 29D, 29E, 29F, 29H, 29I, 29J, 29K, 29L, 29N, 29Q, 29S, or 29U. Other combinations are possible.

Figure 30A:
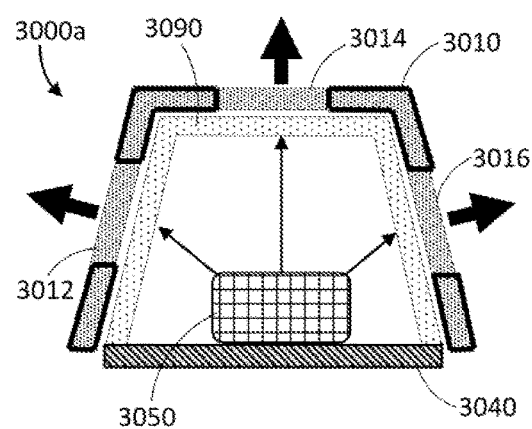
FIGS. 30A, 30B, and 30C are side cross-sectional views of exemplary mask units, in which light sources emit light into the interior volume of the mask units.
Figure 30B:
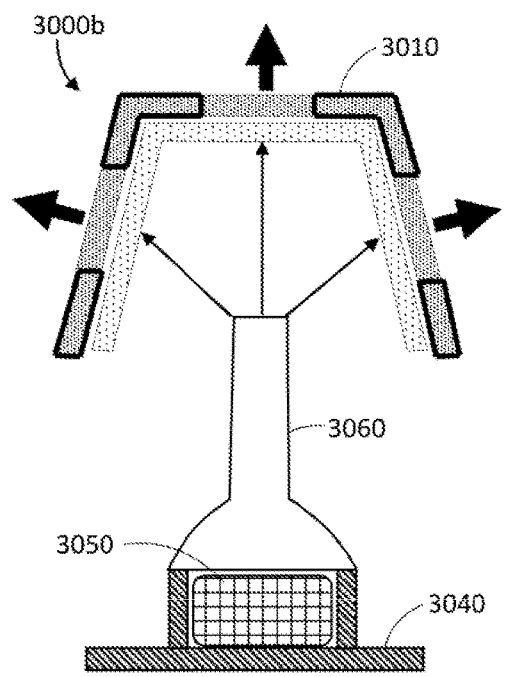
Figure 30C:
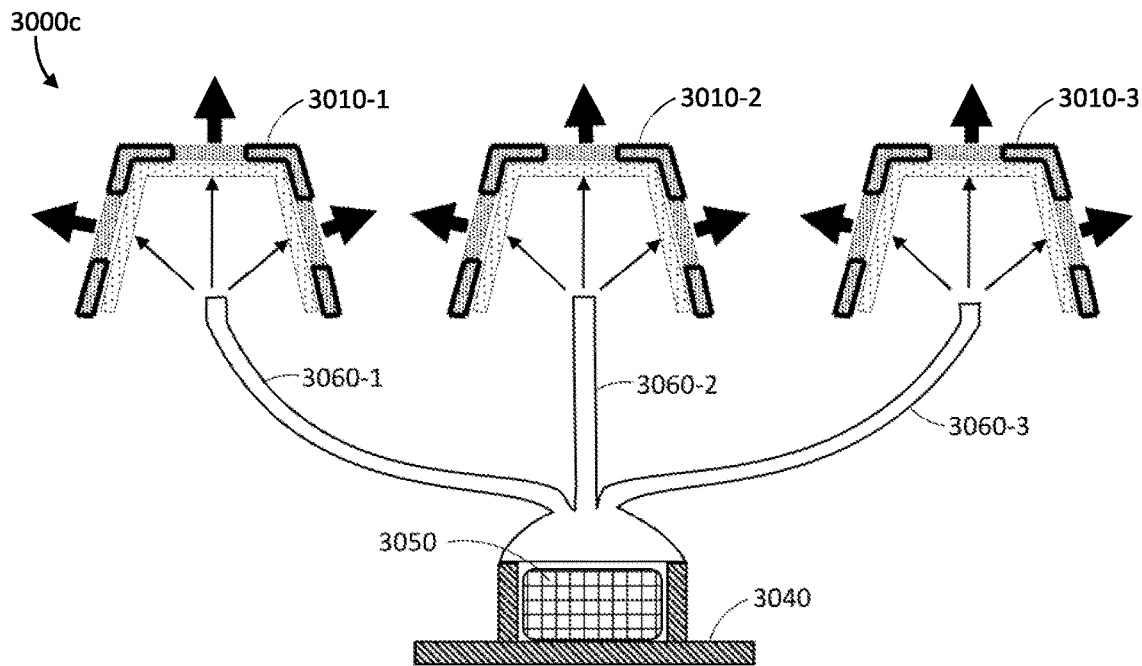

The markers and mask units described herein can also be implemented as active markers: that is, markers which themselves output light (as opposed to passive markers which reflect light from other sources). FIGS. 30A-30C illustrate exemplary implementations of active markers.

FIG. 30A is a side cross-sectional view of an exemplary marker 3000a, which includes a mask unit 3010 having openings 3012, 3014, and 3016. More or less openings could be included in mask unit 3010, as appropriate for a given application. Mask unit 3010 could have any appropriate shape and any appropriate number of faces, similar to the example markers 400, 700, 800 and 1000 described above. Further, a plurality of mask units 3010 could be assembled together to form a single marker, similar to the exemplary markers 1100, 1102, 1104, 1106, 1300, and 1400 described above.

Marker 3000a in FIG. 30A has a light source 3050 positioned in the interior volume of mask unit 3010. Light source 3050 is shown positioned on a substrate 3040, but light source 3050 could be secured in the interior volume of mask unit 3010 by any appropriate means. Optically detectable cartridge 3090 is also positioned in the interior volume of mask unit 3010, and could be secured by any appropriate means, such as those described above with reference to FIGS. 23A-23H. In some implementations, light source 3050 could be carried by a support unit similar to support units 2330 discussed above. In the context of active trackers, cartridge 3090 is optically detectable in the sense that it can be a partially transparent diffusive material, to diffuse light from light source 3050, to be detected by an image sensor and tracking system. In the example of marker 3000a, light source 3050 can emit light into the interior volume of mask unit 3010. Cartridge 3090 can receive light from mask unit 3010 and diffuse at least a portion of the light therethrough, to exit mask unit 3010 through the openings 3012, 3014, and/or 3016. Mask unit 3010 comprises an opaque material to prevent light from passing therethrough except for through the openings. In this way, an image sensor and tracking system can detect the openings of marker 3000a, and determine a pose of marker 3000a.

Light source 3050 could be for example an LED, or any appropriate light source. Cartridge 3090 could be formed of for example polycarbonate, paper, engineered diffusers, or any other appropriate diffusive material. An image sensor can be designed and/or tuned to be sensitive to light having wavelengths corresponding to the wavelengths of light emitted by the light source 3050.

FIG. 30B is a side cross-sectional view of a marker 3000b, which can be similar to marker 3000a in FIG. 30A. Description of marker 3000a can be applicable to marker 3000b.

One difference between marker 3000b and marker 3000a is that in marker 3000b, light source 3050 is positioned external to mask unit 3050. Marker 3000b includes a light redirector 3060, which receives light from light source 3050, and redirects the light to the interior volume of mask unit 3010. The light redirector could be for example a light pipe, an optical fiber, a plurality of light pipes or optical fibers, or any other appropriate light redirector. Once inside the interior volume of mask unit 3010, the light is received by a diffusive cartridge and diffused external to the mask unit 3010 through openings therethrough, similar to as in FIG. 30A.

FIG. 30C is a schematic diagram of a marker 3000c, which can be similar to marker 3000b in FIG. 30B. Description of marker 3000b can be applicable to marker 3000c.

One difference between marker 3000c and marker 3000b is that marker 3000c includes a plurality of mask units. The example of FIG. 30C shows three mask units 3010-1, 3010-2, and 3010-3, but any appropriate number of mask units could be used. Further, the mask units can be arranged in any appropriate pattern for detection and tracking, for example similar to the arrangement of mask units in trackers 1100, 1102, 1104, 1106, 1300, and 1400 discussed above. Instead of including an individual light source in each mask unit (as was discussed with reference to FIG. 30A), a single light source 3050 can be positioned external to each of the mask units. Light from light source 3050 can be redirected to an interior volume of each mask unit. In the example of FIG. 30C, an optical fiber 3060-1 redirects light from light source 3050 to an interior volume of mask unit 3010-1; an optical fiber 3060-2 redirects light from light source 3050 to an interior volume of mask unit 3010-2; and an optical fiber 3060-3 redirects light from light source 3050 to an interior volume of mask unit 3010-3. Although optical fibers are shown in FIG. 30C, alternative light redirection elements could be used, such as light pipes. Once inside the interior volume of a given mask unit, the light is received by a diffusive cartridge and diffused external to the mask unit through openings therethrough, similar to as in FIG. 30A.

In each of the active markers discussed above, power can be supplied to the light source or light sources, such as by a battery or an external power source connected to the light source(s) by a power cable. Such a marker could include a power switch to activate the light source. In some implementations, the cartridge could comprise a region of conductive material, such that when the cartridge is inserted into a mask unit, a power circuit is completed, activating the light source(s). In battery powered markers, insertion of a battery could complete a power circuit which activates the light source(s).

Figure 31:
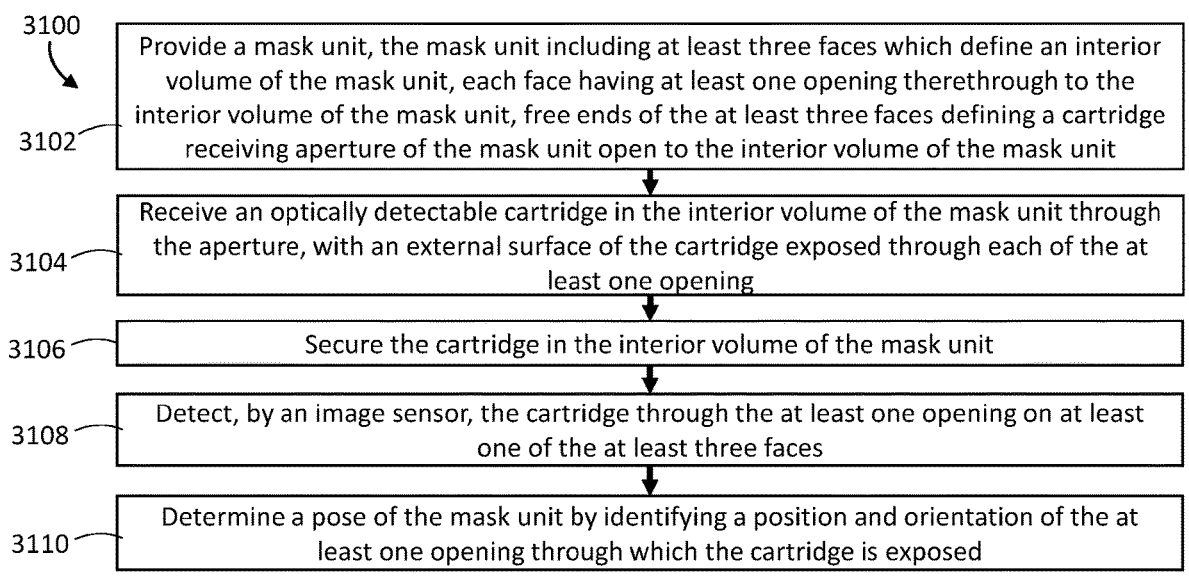
FIG. 31 is a flowchart diagram which illustrates an exemplary method for assembling and using the markers described herein.

FIG. 31 is a flowchart diagram which illustrates an exemplary method 3100 for using any of the markers described herein. Method 3100 is shown as including acts 3102, 3104, and 3106, directed towards assembling and/or setting up the marker. Method 3100 is also shown as including acts 3108 and 3110, directed towards tracking the marker. Assembling the marker and tracking the marker can be separately performed by different entities, and as such method 3100 could also be considered as a first method including acts 3102, 3104, and 3106, and a second method including acts 3108 and 3110. The acts of method 3100 could be reordered, acts could be removed, or acts could be added, as appropriate for a given application.

In act 3102, a mask unit is provided, the mask unit including at least three faces which define an interior volume of the mask unit, each face having at least one opening therethrough to the interior volume of the mask unit, free ends of the at least three faces defining a cartridge receiving aperture of the mask unit open to the interior volume of the mask unit. Such a mask unit could be any of the mask units described herein, including the mask units of markers 400, 700, 800, 1000, 1102, 1104, 1106, 1300, or 1400; mask units 2310, 2510, 2610, 2700, or 3010; or the mask units of FIGS. 29B, 29D-29F, 29H-29L, 29N, 29Q, 29S, 29U.

In act 3104, an optically detectable cartridge is received in the interior volume of the mask unit through the aperture, with an external surface of the cartridge exposed through each of the at least one openings. Such a cartridge could be any of the optically detectable cartridges described herein, including cartridges 490, 790, 890, 1090, 1191, 1192, 1193, 1194, 1390, 1600, 1700, 1800, 2100, 2390, 2490, 2590, 2690, or 3090; or the cartridges of FIG. 29A, 29C, 29G, 29M, 29P, 29R, 29T, or 29X, for example.

In act 3106, the cartridge is secured in the interior volume of the mask unit, such as by any of the mechanisms described with reference to FIGS. 23A-23H.

In markers having multiple mask units, acts 3102, 3104, and 3106 can be repeated for each mask unit. In active trackers, an additional act can be included where a light source is received in the interior volume of the mask unit as in FIG. 30A, or an additional act can be included of providing a light source, and connecting the light source to the interior volume of the mask unit by a light redirector as in FIG. 30B. Additionally, for markers having a plurality of mask units, acts where a light source is received in the interior volume of a mask unit can be repeated for each mask unit. Similarly, for markers having a plurality of mask unit, acts of connecting the light source to the interior volume of the mask unit by a light redirector can be repeated for each mask unit, such as discussed with reference to FIG. 30C.

In act 3108, an image sensor detects the cartridge through the at least one openings on at least one of the at least three faces of the mask unit. For markers having a plurality of mask units, act 3108 can include the image sensor detecting a plurality of cartridges through at least one opening on each of a subset of the mask units.

In act 3110, a tracking system, or processor of a tracking system, determines a pose of the mask unit by identifying a position and orientation of the at least one opening through which the cartridge is exposed. For markers having a plurality of mask units, act 3110 can include the tracking system determining a pose of a subset of the mask units, and determining a pose of the marker based on the poses of the subset of mask units. For example detecting the cartridge can comprise detecting, by the image sensor, at least two cartridges through openings on at least two mask units; and determining a pose can comprise determining a pose of the marker by identifying a position and orientation of the openings through which the cartridges are exposed.

Figure 32:
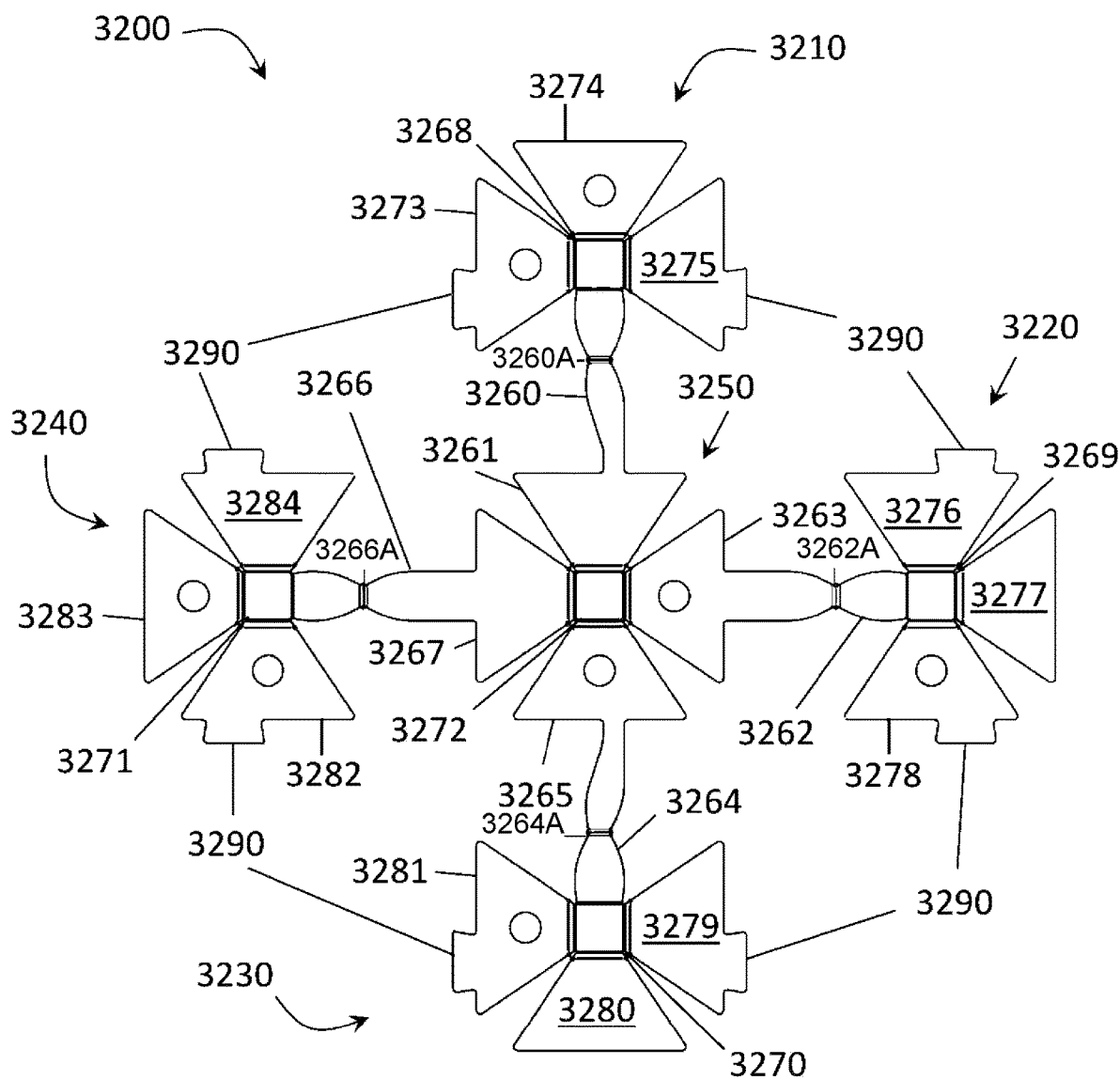
FIG. 32 illustrates a connected cartridge assembly, according to an embodiment.
Figure 33:
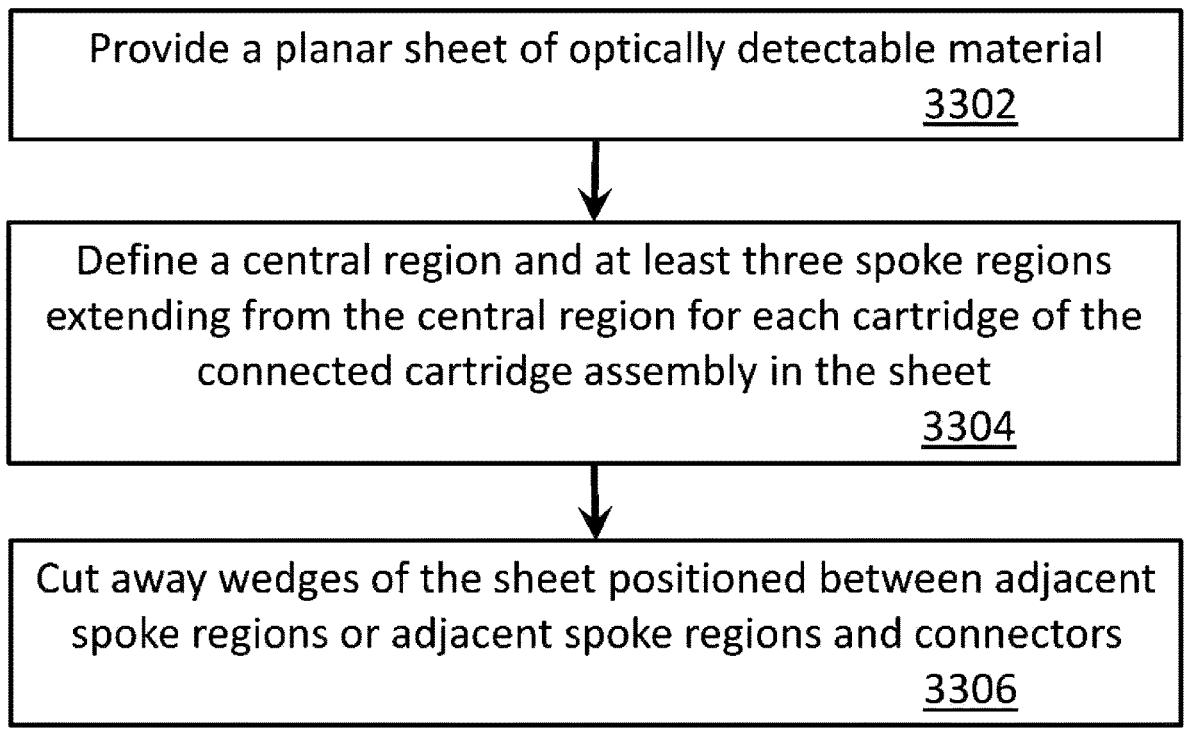
FIG. 33 is a flowchart diagram which illustrates an exemplary method for manufacturing a connected cartridge assembly.

FIG. 32 illustrates a connected cartridge assembly 3200, according to an embodiment. FIG. 33 is a flowchart which illustrates operations 3300 of an exemplary method for manufacturing a connected cartridge assembly 3200.

In reference to FIG. 32, a plurality of cartridges (e.g. 3210, 3220, 3230, 3240 and 3250) are connected together by any appropriate connecting structure. In the example of FIG. 32, four cartridge connectors 3260, 3262, 3264, and 3266 connect the cartridges 3210, 3220, 3230, 3240 and 3250 to each other to form connected cartridge assembly 3200. Four cartridges 3210, 3220, 3230 and 3240 have three spoke regions and one cartridge 3250 has four spoke regions. Cartridge 3210 comprises spoke regions 3273, 3274 and 3275. Cartridge 3220 comprises spoke regions 3276, 3277 and 3278. Cartridge 3230 comprises spoke regions 3279, 8280 and 8281. Cartridge 3240 comprises spoke regions 3282, 8283 and 8284. Cartridge 3250 comprises spoke regions 3261, 3263, 3265 and 3267.

Cartridge connector 3260 couples spoke region 3261 of cartridge 3250 to cartridge 3210, cartridge connector 3262 couples spoke region 3263 of cartridge 3250 to cartridge 3220; cartridge connector 3264 couples spoke region 3265 of cartridge 3250 to cartridge 3230; and cartridge connector 3266 couples spoke region 3267 of cartridge 3250 to cartridge 3240. In this way, the cartridges are coupled together so as to have a predictable geometry. Further, the geometry may correspond to the geometry of the mask units for ease of assembly, such as for assembly with the mask units illustrated for marker 1300, described above and illustrated in FIG. 13A-13E. In some implementations, cartridges 3210, 3220, 3230, 3240, and 3250 can be formed together with cartridge connectors 3260, 3262, 3264 and 3266 as a monolithic structure. In other implementations, cartridges 3210, 3220, 3230, 3240, and 3250 can be formed separately, and can be coupled together as an assembly with cartridge connectors 3260, 3262, 3264 and 3266.

The cartridge assembly 3200 is illustrated as comprising five cartridges, 3210, 3220, 3230, 3240, and 3250. In an embodiment, four cartridges 3210, 3220, 3230 and 3240 may be arranged in a first plane and cartridge 3250 may be positioned in a second plane parallel to but spatially separated from the first plane (configuration illustrated for similar unconnected cartridges in FIG. 13). Alternatively, five cartridges 3210, 3220, 3230, 3240 and 3250 may be positioned in the first plane. The configuration illustrated in FIG. 32 is appropriate for assembly with five mask units in a configuration similar to that illustrated in FIGS. 13A-13E. In other implementations, additional cartridges could be included for assembly with a different number of mask units. Further, a different configuration of cartridges could be included for assembly with a different configuration of mask units. Any number and configuration of cartridges can be connected together for insertion into one or more connected mask units (up to the equivalent number of mask units), provided the mask units have a suitable configuration to receive the cartridges of the connected cartridge assembly 3200. Alternatively, the cartridges 3210, 3220, 3230, 3240 and 3250 may be inserted into five unconnected individual mask units, provided the shape of the mask units is similar to that of mask units 1310, 1320, 1330, 1340, and/or 1350, and the size and configuration of the mask units are suitable for insertion of connected cartridge assembly 3200. The mask units, whether connected or unconnected, may have openings of any suitable shape, such as described above in reference to FIG. 15.

In some implementations, the connected cartridge assembly 3200 described herein is formed from folded planar sheets of material. In this way, many connected cartridge assemblies can be stored efficiently in a planar configuration, and later folded for insertion in a mask unit when needed. FIG. 32 illustrates an exemplary foldable connected cartridge assembly 3200 in this regard.

In FIG. 32, connected cartridge assembly 3200 is illustrated as a front view thereof in an unfolded state. The cartridges of connected cartridge assembly 3200 are similar to cartridges 1600 and 1700 discussed above, such that description of cartridges 1600 and 1700 applies to cartridges 3210, 3220, 3230, 3240 and 3250 of connected cartridge assembly 3200. One difference between cartridges 3210, 3220, 3230, 3240 and 3250 and cartridge 1700 is that central regions 3268, 3269, 3270, 3271 and 3272 are shown as being smaller than central region 1750 (though this is optional). Another difference is that the spoke regions, for example, regions 3273, 3274, and 3275, have a more triangular shape compared to the spoke regions 1710, 1720, 1730 and 1740 of cartridge 1700. Another difference is that cartridges 3210, 3220, 3230, and 3240 only have three spoke regions, instead of four, with the fourth spoke region replaced by the cartridge connector (e.g. 3260, 3262, 3264, and 3266) connecting respectively each of the outer cartridges (e.g. 3210, 3220, 3230 and 3240) to the central cartridge 3250. In comparison, cartridge 1700 has four faces, which is similar to the central cartridge 3250.

Similar to cartridge 1700, the spoke regions, for example, 3261, 3263, 3265 and 3267 of cartridge 3250 of connected cartridge assembly 3200, can be separated by gaps (as shown) or collapsible regions (not shown), and boundaries between the spoke regions and central region 3272 can be weakened along a fold line. FIG. 32 shows connector fold lines 3260A, 3262A, 3264A, and 3266A, in the cartridge connectors 3260, 3262, 3264, and 3266. Each of the connectors is generally formed of a strip. The width of each connector narrows at the respective fold line, which can assist with folding. The sizing (e.g. width dimension) of a strip, in an embodiment, is selected to correspond to and cooperate with a width of the respective mask unit connector with which it is associated when the cartridges are inserted into the connected mask units. FIG. 13C shows marker 1300 having mask connectors 1360-1366. When assembled, the cartridge connectors run along and adjacent to the mask connectors. When in use, the optically detectable material of any cartridge connector is generally obscured by a respective mask unit connector with which the material is adjacent.

The lengths of each cartridge connector from the central region to the fold line generally defines the distance between the plane in which the spoke regions are positioned and the plane in which the central region is positioned when the sheet is folded along the boundary and connector fold lines. In an embodiment, the spoke regions are positioned on a same plane and the central region on a different plane such as illustrated by marker 1300 in FIG. 13A. The connector fold lines facilitate insertion of the connectors, defined by the spoke regions, into the respective mask units 1310, 1320, 1330 and 1340.

It will be appreciated that any of the marker bodies and cartridges can be sold as a kit for assembly. In an embodiment, the kit may comprise a marker body comprising a plurality of mask units, and a plurality of cartridges. In an embodiment, the marker body comprises a unitary body of mask units and connectors. In an embodiment, the marker is sold for assembly and the kit comprises a plurality of mask units and mask unit connectors for assembly to make the marker body (e.g. before inserting the cartridges). In an embodiment, the cartridges comprise individual (separated) cartridges for assembly with the marker by inserting into the mask units. In an embodiment, the kit may include a plurality of support units for inserting into the mask units to secure the cartridges therein.

In an embodiment, the cartridges form a connected cartridge assembly. In an embodiment, the kit includes a plurality of cartridge connectors to assemble the plurality of cartridges into the assembly (e.g. prior to insertion of the cartridges into the mask units). In an embodiment, the plurality of cartridges are (pre-)formed from a planar sheet of optically detectable material and comprise a monolithic structure including the connectors.

In an embodiment, the kit includes instructions to assemble the marker, for example, to insert the cartridges into the mask unit and optionally, and in accordance with the components of the kit, instructions to fold the material of the cartridges to create their shape, fold a connected cartridge assembly to make its shape, connect mask units and respective mask unit connectors to assemble the marker body or connect cartridge with respective cartridge connectors to assemble a connected cartridge assembly.

The configuration of the connected cartridge assembly 3200, as depicted in FIG. 32, is suitable for use with mask units having a similar geometry (e.g. four side faces), such as marker 1300. The geometry of the cartridges 3210, 3220, 3230, 3240 and 3250 and the size of the central regions 3268, 3269, 3270, 3271 and 3272 may need to be altered in size for the cartridges to match the shape and size of the mask units in marker 1300. See for example, FIGS. 13A and 13C.

Operations 3300 of the flowchart of FIG. 33 illustrate an exemplary method for manufacturing connected cartridge assemblies, such as 3200, as discussed above. The operations includes acts 3302, 3304 and 3306, though additional acts could be added as appropriate.

In act 3302, a planar sheet of optically detectable material is provided. The optically detectable material is further discussed above.

In act 3304, a central region and at least three spoke regions extending from the central region are defined in the sheet for each cartridge in the connected cartridge assembly. Any appropriate number of spoke regions could be defined for each cartridge, including four or eight spoke regions, as non-limiting examples discussed above with reference to FIG. 32. The cartridges may have different numbers of spokes or the same number of spokes. The spoke regions of each cartridge are defined to have a size and shape approximating the interior size and shape of a side face of a mask into which each cartridge is intended to be inserted.

In act 3306, wedges of the sheet between adjacent spoke regions or adjacent spoke regions are cut away. This enables the spoke regions to be folded relative to the central regions to form a three-dimensional connected cartridge assembly for insertion into the interior volumes of three-dimensional mask units.

Optionally, operations 3300 may further include an act (not shown) to weaken each boundary between each of the spoke regions and the central regions to form a fold line at each boundary, as discussed above.

In the illustrated embodiment of FIG. 32, one or more of the mechanisms for securing a cartridge in a mask unit described above and illustrated in FIGS. 23A-23H apply to the securing the cartridges of a connected cartridge assembly 3200 in corresponding mask units. However, in other embodiments, not shown, other mechanisms may be used.

As described above, the faces of the cartridges of the connected cartridge assembly may have optically non-detectable patterns thereon and/or holes through the cartridge. By using different patterns and/or holes through the cartridge for one or more faces on a cartridge and using a different combination and arrangement of patterns and/or holes through the cartridge for two or more cartridges, unique identification of faces can be achieved. Alignment of patterns and/or holes and mask unit openings can also be useful to identify faces, as discussed above.

In order to ensure that connected cartridge assemblies are installed in mask units of a marker in the correct orientation to uniquely identify the marker and faces thereof, and/or to match patterns expected by a tracking system, alignment features can be included in the mask unit and/or cartridges, as discussed below with reference to FIG. 32.

In the illustrated embodiment of a connected cartridge assembly, the cartridges of connected cartridge assembly 3200 are similar to the cartridges shown in FIGS. 29P and 29R discussed above, such that the description of FIGS. 29P and 29R apply to cartridges 3210, 3220, 3230, 3240 and 3250 of the connected cartridge assembly 3200. The arrangement of tabs 3290 on the cartridges are positioned to correspond to recesses on the mask units, such as the recesses 2916, 2918, and 2920 discussed above and depicted in FIGS. 29Q and 29S. In an exemplary embodiment, the arrangement of tabs 3290 in the connected cartridge corresponds to the recesses in the corresponding mask units and ensures the connected cartridge assembly 3200 is installed in the mask units of a marker in the correct orientation. Although the mechanism for aligning a cartridge within a mask unit depicted in FIG. 32 are tabs, any of the exemplary techniques and mechanisms for aligning a cartridge within a mask unit, such as described above and depicted in FIGS. 29A-29Z, may be used, alone or in combination.

Thus, there is provided the following connected cartridge assembly embodiments:

Embodiment 1: A connected cartridge assembly for use in an optical marker comprising:
a planar sheet of optically detectable material forming a plurality of optically detectable cartridges connected together; wherein, each respective cartridge of the plurality of cartridges: comprises at least three regions; is foldable at boundaries between adjacent regions of the at least three regions to define respective cartridge faces; and is sized and dimensioned, when folded at the boundaries, to be inserted into an interior volume of a respective mask unit of a plurality of mask units defining the optical marker, one respective cartridge per one respective mask unit, each respective mask unit defining an cartridge receiving aperture and each respective mask unit having at least three mask faces and at least three of the mask faces having at least one opening therethrough to the interior volume for exposing cartridge faces when inserted.

Embodiment 2: The connected cartridge assembly of embodiment 1, wherein the plurality of cartridges comprises four cartridges and three of the four cartridges are positioned spatially separated from each other in a first plane, and the fourth cartridge is positioned in a second plane spatially separated from the first plane.

Embodiment 3: The connected cartridge assembly of embodiment 2, wherein: the planar sheet forms a plurality of cartridge connectors to connect the plurality of cartridges together in a monolithic body; the plurality of cartridge connectors comprise connector fold lines and the boundaries comprise boundary fold lines; and the three of the four cartridges are positioned spatially separated from each other when the sheet is folded along the boundary fold lines and the connector fold lines.

Embodiment 4: The connected cartridge assembly of embodiment 1, wherein the plurality of cartridges comprises five cartridges and four of the five cartridges are positioned spatially separated from each other in a first plane, and the fifth cartridge is positioned in a second plane spatially separated from the first plane.

Embodiment 5: The connected cartridge assembly of embodiment 4, wherein: the planar sheet forms a plurality of cartridge connectors to connect the plurality of cartridges together in a monolithic body; the plurality of cartridge connectors comprise connector fold lines and the boundaries comprise boundary fold lines; and the four of the five cartridges are positioned spatially separated from each other when the sheet is folded along the boundary fold lines and the connector fold lines.

Embodiment 6: The connected cartridge assembly of embodiment 1, wherein the planar sheet forms a plurality of cartridge connectors to connect the plurality of cartridges together in a monolithic body.

Embodiment 7: The connected cartridge assembly of embodiment 6, wherein the planar sheet forms the plurality of cartridge connectors as respective strips of the sheet to connect the plurality of cartridges together in the monolithic body, the strips sized to correspond and cooperate with a size of respective mask unit connectors connecting the plurality of mask units in the optical marker when the plurality of cartridges are inserted in the plurality of mask units.

Embodiment 8: The connected cartridge assembly of embodiment 6, wherein the planar sheet is formed to provide separation between the spoke regions by gaps in the planar sheet.

Embodiment 9: The connected cartridge assembly of embodiment 6, wherein: the at least three regions for each respective cartridge define a central region and a plurality of spoke regions, wherein each respective spoke region is adjacent to and extending from the central region; and the boundaries between adjacent regions are weakened along respective fold lines.

Embodiment 10: The connected cartridge assembly of embodiment 9, wherein the plurality of spoke regions provides either a) one spoke region for each face of the mask unit into which the respective cartridge is to be inserted; or one fewer spoke regions than the number of faces of the mask unit into which the respective cartridge is to be inserted.

Embodiment 11: The connected cartridge assembly of embodiment 9, wherein the planar sheet forms a plurality of connectors to connect each of the spoke regions directly to the central region by a respective single connector.

Embodiment 12: The connected cartridge assembly of embodiment 11, wherein: the boundaries comprise respective boundary fold lines; the cartridge connectors comprise respective connector fold lines; and when the connected cartridge assembly is folded along the respective boundary fold lines and the respective connector fold lines, at least three of the plurality of cartridges are positioned spatially separated from each other in a first plane, and at least another of the plurality of cartridges is positioned in a second plane spatially separated from the at least three cartridges of the first plane.

Embodiment 13: The connected cartridge assembly of embodiment 1, wherein, in at least one respective cartridge, there is defined either a hole in one of the at least three regions or an optically non-detectable pattern on one of the at least three regions to align with a respective opening of the respective mask unit into which the at least one respective cartridge is to be inserted.

Embodiment 14: The connected cartridge assembly of embodiment 1, wherein the respective cartridge comprises at least one alignment feature to align with a respective alignment feature of the mask unit into which the respective cartridge is inserted.

There is provided the following connected cartridge assembly method embodiments, carrying the embodiment numbering consecutively for convenience:

Embodiment 15: A method of manufacturing a connected cartridge assembly comprising: providing a sheet of optically detectable material; forming in the sheet a plurality of optically detectable cartridges connected together, wherein each respective cartridge of the plurality of optically detectable cartridges comprises at least three regions; and wherein each respective cartridge is sized and dimensioned, when folded at the boundaries, to insert into an interior volume of a respective mask unit of a plurality of mask units defining the optical marker, each mask unit defining an aperture to receive one of the plurality of optically detectable cartridges and each mask unit having at least three faces with at least three of the faces having at least one opening therethrough to the interior volume for exposing the one of the plurality of optically detectable cartridges as inserted.

Embodiment 16: The method of claim 15 comprising, in each respective cartridge, weakening each of the boundaries between adjacent regions of the at least three regions to produce boundary fold lines.

Embodiment 17: The embodiment of claim 15 comprising forming cartridge connectors in the sheet between the respective cartridges.

Embodiment 18: The embodiment of claim 15, wherein, for each respective cartridge: the at least three regions are formed as a central region and a plurality of spoke regions each connected to and extending from the central region; and the boundaries between adjacent regions are between the central region and each respective spoke region.

Embodiment 19: The method of embodiment 18 comprising forming cartridge connectors in the sheet between the respective cartridges; cutting away wedges of the sheet between adjacent spoke regions or adjacent spoke regions and cartridge connectors; and weakening each boundary between each respective spoke region and the central region; and weakening each of the cartridge connectors to produce connector fold lines.

Embodiment 20: The method of embodiment 17 comprising either a) forming four cartridges, wherein when the sheet is folded, three of the four cartridges are positioned spatially separated from each other in a first plane, and the fourth cartridge is positioned in a second plane spatially separated from the first plane; or b) forming five cartridges, wherein, when the sheet is folded, four of the five cartridges are positioned spatially separated from each other in a first plane, and the fifth cartridge is positioned in a second plane spatially separated from the first plane.

The various computing devices shown herein can comprise a processing unit (for example a microprocessor, FPGA, ASIC, logic controller, or any other appropriate processing hardware), a storage device (e.g. non-transitory processor-readable storage medium, such as memory, RAM, ROM, magnetic-disk, solid state storage, or any other appropriate storage hardware) storing instructions which when and executed by the processing unit configure the computing device to perform operations for example to provide the functionality and features described herein. Computer program code for carrying out operations may be written in any combination of one or more programming languages, e.g., an object oriented programming language such as Java, Smalltalk, C++ or the like, or a conventional procedural programming language, such as the "C" programming language or similar programming languages.

Any of the computing devices may have communication subsystems to communicate via a network. Any may have a display device and other input and/or output devices.

In any of the components indicating as having a hole, the component has a surface that defines a hole through the surface.

Practical implementation may include any or all of the features described herein. These and other aspects, features and various combinations may be expressed as methods, apparatus, systems, means for performing functions, program products, and in other ways, combining the features described herein. A number of embodiments have been described. Nevertheless, it will be understood that various modifications can be made without departing from the spirit and scope of the processes and techniques described herein. In addition, other steps can be provided, or steps can be eliminated, from the described process, and other components can be added to, or removed from, the described systems. Accordingly, other embodiments are within the scope of the following claims.

Throughout the description and claims of this specification, the word "comprise", "contain" and variations of them mean "including but not limited to" and they are not intended to (and do not) exclude other components, integers or steps. Throughout this specification, the singular encompasses the plural unless the context requires otherwise. In particular, where the indefinite article is used, the specification is to be understood as contemplating plurality as well as singularity, unless the context requires otherwise.

Features, integers, characteristics, or groups described in conjunction with a particular aspect, embodiment or example of the invention are to be understood to be applicable to any other aspect, embodiment or example unless incompatible therewith. All of the features disclosed herein (including any accompanying claims, abstract and drawings), and/or all of the steps of any method or process so disclosed, may be combined in any combination, except combinations where at least some of such features and/or steps are mutually exclusive. The invention is not restricted to the details of any foregoing examples or embodiments. The invention extends to any novel one, or any novel combination, of the features disclosed in this specification (including any accompanying claims, abstract and drawings) or to any novel one, or any novel combination, of the steps of any method or process disclosed.

The invention claimed is:

1. An optical marker kit comprising:
 a marker body comprising a plurality of mask units spaced from one another and connected by mask unit connectors, each mask unit including at least three faces defining an interior volume of the respective mask unit, at least one face of each mask unit having at least one opening therethrough to the interior volume of the respective mask unit, free ends of the at least three faces of the respective mask unit defining a cartridge receiving aperture to the interior volume of the mask unit; and
 a connected cartridge assembly comprising a plurality of cartridges spaced from one another and connected by cartridge connectors, each cartridge insertable into the interior volume of one of the mask units through the aperture therein, a surface of a respective cartridge exposed through each of the at least one openings in a respective mask unit into which the respective cartridge is inserted, each cartridge being optically detectable relative to the plurality of mask units.

2. The marker kit of claim 1, wherein the at least three faces of each mask unit include at least four faces.

3. The marker kit of claim 1, wherein the plurality of mask units includes four mask units;
 and wherein three of the four mask units are positioned spatially separated from each other in a first plane, and the fourth mask unit is positioned in a second plane spatially separated from the first plane.

4. The marker kit of claim 1, wherein the plurality of mask units includes five mask units;
 and wherein four of the five mask units are positioned spatially separated from each other in a first plane, and the fifth mask unit is positioned in a second plane spatially separated from the first plane.

5. The marker kit of claim 1, wherein each mask unit of a first subset of the plurality of mask units has an optically detectable identifier positioned thereon.

6. The marker kit of claim 5, wherein each mask unit of a second subset of the plurality of mask units has an optically non-detectable identifier positioned thereon, the first and second subsets being non-overlapping subsets.

7. The marker kit of claim 6, wherein each optically detectable identifier and each optically non-detectable identifier are positioned on the respective mask unit adjacent each face of the at least three faces of the mask unit.

8. The marker kit of claim 5, wherein a second subset of the plurality of mask units has no optically detectable identifier positioned thereon, the first and second subsets being non-overlapping subsets which together include the entire plurality of mask units.

9. The marker kit of claim 1, wherein each of the cartridges comprises a foldable planar sheet which includes at least three regions, the sheet foldable at boundaries between adjacent regions to define cartridge faces for each of at least three of the faces of each mask unit and to fit in the interior volume of the respective mask unit and be exposed through the at least one opening on the at least three faces of the respective mask unit.

10. The marker kit of claim 9, wherein the plurality of cartridges and the cartridge connectors are formed from a single foldable planar sheet to provide the connected cartridge assembly as a monolithic body.

11. The marker kit of claim 9, wherein:
 the at least three regions for each of the cartridges define a central region and a plurality of spoke regions, wherein each respective spoke region is adjacent to and extending from the central region; and
 the boundaries between adjacent regions are weakened along respective fold lines.

12. The marker kit of claim 11, wherein either a) the plurality of spoke regions provides one spoke region for each face of the mask unit into which the respective cartridge is to be inserted; or b) the plurality of spoke regions provided is one fewer than the number of faces of the mask unit into which the respective cartridge is to be inserted.

13. The marker kit of claim 11, wherein the sheet is formed to provide separation between the spoke regions by gaps in the sheet.

14. The marker kit of claim 11, wherein each of the cartridges comprises at least one alignment feature to align with respective alignment features of the respective mask units into which the cartridges are to be inserted.

15. The marker kit of claim 11, wherein the plurality of cartridges and the cartridge connectors are formed from a single foldable planar sheet to provide the connected cartridge assembly as a monolithic body, and wherein the cartridge connectors comprise respective connector fold lines, and wherein, when the connected cartridge assembly is folded along the boundary fold lines and the connector fold lines, at least three of the plurality of cartridges are positioned spatially separated from each other in a first plane, and at least one other cartridge of the plurality of cartridges is positioned in a second plane spatially separated from the at least three cartridges of the first plane.

16. The marker kit of claim 11, wherein the plurality of mask units comprises either four mask units or five mask units.

17. The marker kit of claim 1, wherein the cartridges are secured in the interior volume of respective mask units by one or more of magnets, clips, adhesive, or friction fit.

18. The marker kit of claim 1, wherein each of the cartridges has a shape which matches a shape of the interior volume of each mask unit.

19. The marker kit of claim 1, wherein one of a) the exposed surface of each of the cartridges is reflective of light, and an exterior surface of each mask unit is non-reflective of light; or b) the exposed surface of each cartridge is non-reflective of light, and an exterior surface of each mask unit is reflective of light.

20. The marker kit of claim 1, wherein each of the cartridges has an optically non-detectable pattern or provides a hole therethrough to align with and be exposed through a respective opening of the at least one opening of a respective mask unit.

* * * * *